United States Patent
Orimoto et al.

(10) Patent No.: US 11,149,027 B2
(45) Date of Patent: Oct. 19, 2021

(54) HETEROCYCLIC COMPOUND

(71) Applicant: Sumitomo Chemical Company, Limited, Tokyo (JP)

(72) Inventors: Kohei Orimoto, Takarazuka (JP); Takamasa Tanabe, Takarazuka (JP); Ryota Maehata, Takarazuka (JP); Yuji Nakajima, Takarazuka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 220 days.

(21) Appl. No.: 16/086,715

(22) PCT Filed: Mar. 17, 2017

(86) PCT No.: PCT/JP2017/010883
§ 371 (c)(1),
(2) Date: Sep. 20, 2018

(87) PCT Pub. No.: WO2017/169894
PCT Pub. Date: Oct. 5, 2017

(65) Prior Publication Data
US 2019/0106411 A1    Apr. 11, 2019

(30) Foreign Application Priority Data
Mar. 31, 2016 (JP) .............. JP2016-070632

(51) Int. Cl.
*C07D 403/14* (2006.01)
*C07D 401/14* (2006.01)
*A01N 43/58* (2006.01)
*A01N 43/60* (2006.01)
*A01N 43/653* (2006.01)
*C07D 403/04* (2006.01)
(Continued)

(52) U.S. Cl.
CPC .......... *C07D 403/14* (2013.01); *A01N 43/58* (2013.01); *A01N 43/60* (2013.01); *A01N 43/653* (2013.01); *A01P 7/02* (2021.08); *A01P 7/04* (2021.08); *C07D 401/14* (2013.01); *C07D 403/04* (2013.01)

(58) Field of Classification Search
None
See application file for complete search history.

(56) References Cited

U.S. PATENT DOCUMENTS 7,238,697 B2   7/2007  Bretschneider et al.
8,318,702 B2   11/2012 Kondoh et al.
(Continued)

FOREIGN PATENT DOCUMENTS

CN  1684960 A     10/2005
JP  200026421 A    1/2000
(Continued)

OTHER PUBLICATIONS

Office Action dated May 4, 2020 in IN Application No. 201847036090.
Extended European Search Report dated Oct. 21, 2019 in EP Application No. 17774435.6.
Hearing Notice issued Nov. 23, 2020 in IN Application No. 201847036090.
(Continued)

*Primary Examiner* — John Pak
*Assistant Examiner* — Daniel L Branson
(74) *Attorney, Agent, or Firm* — Panitch Schwarze Belisario & Nadel LLP

(57) ABSTRACT

Provided is a compound of formula (I) or an N-oxide thereof, wherein $Het^1$ represents $Het^1$-1, $Het^1$-2, $Het^1$-3, $Het^1$-4 or $Het^1$-5, and the remaining variable groups are as defined in the specification. The compound of formula (I) or N-oxide compound thereof has an excellent control effect against arthropod pests.

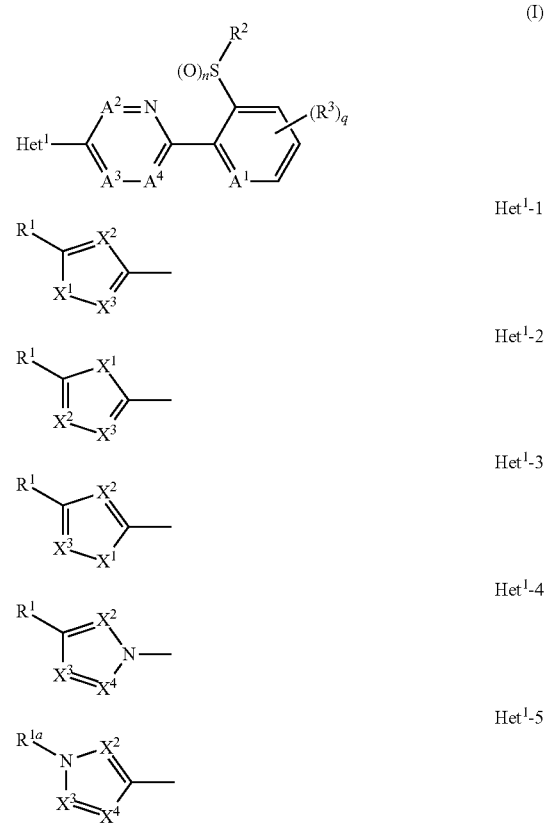

17 Claims, No Drawings

(51) Int. Cl.
    *A01P 7/02*     (2006.01)
    *A01P 7/04*     (2006.01)

(56) References Cited

U.S. PATENT DOCUMENTS

| 9,221,780 | B2 | 12/2015 | Toscano et al. |
| 2004/0077641 | A1 | 4/2004 | Bretschneider et al. |

FOREIGN PATENT DOCUMENTS

| JP | 2004524310 A | 8/2004 |
| WO | 9206085 A1 | 4/1992 |
| WO | 2004031176 A2 | 4/2004 |
| WO | 2005040100 A1 | 5/2005 |
| WO | 2005040110 A1 | 5/2005 |
| WO | 2007123855 A2 | 11/2007 |
| WO | 2012086848 A1 | 6/2012 |
| WO | 2013018928 A1 | 2/2013 |
| WO | 2015177109 A1 | 11/2015 |
| WO | 2016005263 A1 | 1/2016 |
| WO | 2016030229 A1 | 3/2016 |

OTHER PUBLICATIONS

Office Action dated Jul. 20, 2020 in EP Application No. 17774435.6.
Int'l Search Report dated Jun. 13, 2017 in Int'l Application No. PCT/JP2017/010883 (1 page).
Int'l Preliminary Reporton Patentability dated Oct. 2, 2018 in Int'l Application No. PCT/JP2017/010883.
Office Action dated Mar. 4, 2020 in CN Application No. 201780021162.5.

HETEROCYCLIC COMPOUND

CROSS-REFERENCE TO RELATED APPLICATION

This application is a Section 371 of International Application No. PCT/JP2017/010883, filed Mar. 17, 2017, which was published in the Japanese language on Oct. 5, 2017, under International Publication No. WO 2017/169894 A1, which claims priority under 35 U.S.C. § 119(b) to Japanese Application No. 2016-070632, filed Mar. 31, 2016, the disclosures of which are incorporated herein by reference in their entirety.

TECHNICAL FIELD

The present invention relates to a heterocyclic compound and an agent for controlling harmful arthropods comprising said compound.

BACKGROUND ART

To date, some compounds for controlling harmful arthropods have been developed and come into practical use (see, for example, Patent Document 1).
Further, it is known that a certain type of compounds has an efficacy for controlling harmful arthropods.

CITATION LIST

Patent Document

Patent Document 1: WO 92/06085

SUMMARY OF THE INVENTION

Problems to be Solved by Invention

An object of the present invention is to provide a compound that has an excellent efficacy for controlling harmful arthropods.

Means to Solve Problems

The present invention is as follows.
[1] A compound represented by formula (I):

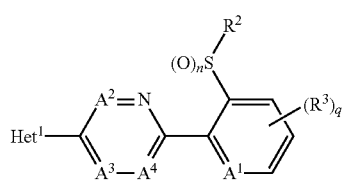

wherein,
$Het^1$ represents $Het^1$-1, $Het^1$-2, $Het^1$-3, $Het^1$-4 or $Het^1$-5:

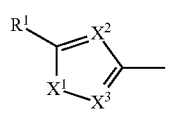
Het¹-1

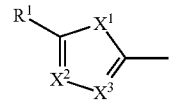
Het¹-2

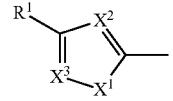
Het¹-3

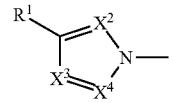
Het¹-4

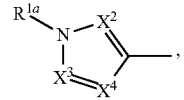
Het¹-5

$R^1$ represents $OR^4$, $OS(O)_2R^4$, $S(O)_mR^4$, $NR^5S(O)_2R^4$, a cyano group, a C1-C4 chain hydrocarbon group having one or more halogen atoms, or a halogen atom, $R^{1a}$ and $R^4$ each independently represents a C1-C4 chain hydrocarbon group having one or more halogen atoms, $R^5$ represents a hydrogen atom, or a C1-C6 chain hydrocarbon group optionally having one or more halogen atoms, $X^1$ represents $NR^{30}$, an oxygen atom, or a sulfur atom,
$X^2$ represents a nitrogen atom or $CR^{31}$,
$X^3$ represents a nitrogen atom or $CR^{32}$,
$X^4$ represents a nitrogen atom or $CR^{33}$, $R^{30}$, $R^{31}$, $R^{32}$, and $R^{33}$ each independently represents a hydrogen atom, a C1-C6 chain hydrocarbon group optionally having one or more halogen atoms, a C3-C6 alicyclic hydrocarbon group optionally having one or more halogen atoms, or a halogen atom, $A^1$ represents a nitrogen atom or $CR^9$,
A combination of $A^2$, $A^3$, and $A^4$ represents
a combination in which $A^2$ is $CR^6$, $A^3$ is $CR^7$, and $A^4$ is $CR^8$,
a combination in which $A^2$ is a nitrogen atom, $A^3$ is $CR^7$, and $A^4$ is $CR^8$,
a combination in which $A^2$ is $CR^6$, $A^3$ is a nitrogen atom, and $A^4$ is $CR^8$, or
a combination in which $A^2$ is $CR^6$, $A^3$ is $CR^7$, and $A^4$ is a nitrogen atom, $R^9$ represents a hydrogen atom or a halogen atom,
$R^6$, $R^7$, and $R^8$ each independently represents a hydrogen atom, a C1-C6 chain hydrocarbon group optionally having one or more halogen atoms, a nitro group, $OR^{18}$, $NR^{18}R^{19}$, a cyano group, or a halogen atom, n represents 0, 1, or 2,
$R^2$ represents a cyclopropyl group, a cyclopropylmethyl group, or a C1-C6 alkyl group optionally having one or more halogen atoms, q represents 0, 1, 2, or 3,
$R^3$ represents a C1-C6 chain hydrocarbon group optionally having one or more substituents selected from Group B; a phenyl group optionally having one or more substituents selected from Group D; a 5 or 6 membered aromatic heterocyclic group optionally having one or more substituents selected from Group D; a nitro group; $OR^{12}$; $NR^{11}R^{12}$; $NR^{11a}R^{12a}$; $NR^{24}NR^{11}R^{12}$; $NR^{24}OR^{11}$; $NR^{11}C(O)R^{13}$; $NR^{24}NR^{11}C(O)R^{13}$; $NR^{11}C(O)OR^{14}$; $NR^{24}NR^{11}C(O)OR^{14}$; $NR^{11}C(O)NR^{15}R^{16}$; $NRR^{24}NR^{11}C(O)NR^{15}R^{16}$; $N=CHNR^{15}R^{16}$; $N=S(O)_xR^{15}R^{16}$; $S(O)_yR^{15}$; $C(O)OR^{17}$;

C(O)NR$^{11}$R$^{12}$; a cyano group; or a halogen atom, and when q is 2 or 3, two or more R$^3$ may be identical to or different from each other, R$^{11}$, R$^{17}$, R$^{18}$, R$^{19}$, and R$^{24}$ each independently represents a hydrogen atom, or a C1-C6 chain hydrocarbon group optionally having one or more halogen atoms, R$^{12}$ represents a hydrogen atom, S(O)$_2$R$^{23}$, a C1-C6 chain hydrocarbon group optionally having one or more halogen atoms, or a C1-C6 alkyl group having one substituent selected from Group F, R$^{23}$ represents a C1-C6 chain hydrocarbon group optionally having one or more halogen atoms, or a phenyl group optionally having one or more substituents selected from Group D, R$^{11a}$ and R$^{12a}$ are taken together with the nitrogen atom to which they are attached to form a 3-7 membered nonaromatic heterocyclic group optionally having one or more substituents selected from Group E wherein the 3-7 membered nonaromatic heterocycle represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiadinane ring, a thiomorpholine ring, or a 1,4-thiazepane ring, R$^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a 5 or 6 membered aromatic heterocyclic group optionally having one or more substituents selected from Group D, R$^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group wherein the phenyl moiety in the phenyl C1-C3 alkyl group may optionally have one or more substituents selected from Group D, R$^{15}$ and R$^{16}$ each independently represents a C1-C6 alkyl group optionally having one or more halogen atoms, m represents 0, 1, or 2, x represents 0 or 1, y represents 0, 1, or 2, Group B: the group consisting of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom, Group C: the group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom, Group D: the group consisting of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, NHR$^{21}$, NR$^{21}$R$^{22}$, C(O)R$^{21}$, OC(O)R$^{21}$, C(O)OR$^{21}$, a cyano group, a nitro group, and a halogen atom, wherein R$^{21}$ and R$^{22}$ each independently represents a C1-C6 alkyl group optionally having one or more halogen atoms, Group E: the group consisting of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group, Group F: the group consisting of a C1-C6 alkoxy group optionally having one or more halogen atoms, an amino group, NHR$^{21}$, NR$^{21}$R$^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3-7 membered nonaromatic heterocyclic group optionally having one or more substituents selected from Group C wherein the 3-7 membered nonaromatic heterocycle represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiadinane ring, a thiomorpholine ring, or a 1,4-thiazepane ring, or its N-oxide compound (hereinafter, a compound represented by formula (1) and its N-oxide compound are referred to as "present compound").

[2] The compound according to [1], wherein the combination of A$^2$, A$^3$, and A$^4$ represents a combination in which A$^2$ is CR$^6$, A$^3$ is CR$^7$, and A$^4$ is CR$^8$, a combination in which A$^2$ is a nitrogen atom, A$^3$ is CR$^7$, and A$^4$ is CR$^8$, or a combination in which A$^2$ is CR$^6$, A$^3$ is a nitrogen atom, and A$^4$ is CR$^8$.

[3] The compound according to [1], wherein the combination of A$^2$, A$^3$, and A$^4$ represents a combination in which A$^2$ is CR$^6$, A$^3$ is CR$^7$, and A$^4$ is CR$^8$.

[4] The compound according to [1], wherein the combination of A$^2$, A$^3$, and A$^4$ represents a combination in which A$^2$ is a nitrogen atom, A$^3$ is CR$^7$, and A$^4$ is CR$^8$.

[5] The compound according to [1], wherein the combination of A$^2$, A$^3$, and A$^4$ represents a combination in which A$^2$ is CR$^6$, A$^3$ is a nitrogen atom, and A$^4$ is CR$^8$.

[6] The compound according to any one of [1] to [5], wherein Het$^1$ represents Het$^1$-1, Het$^1$-2, Het$^1$-3, or Het$^1$-4.

[7] The compound according to any one of [1] to [5], wherein Het$^1$ represents Het$^1$-2 or Het$^1$-4.

[8] The compound according to any one of [1] to [5], wherein Het$^1$ represents Het$^1$-4.

[9] The compound according to any one of [1] to [8], wherein R$^3$ represents a C1-C6 alkyl group optionally having one or more halogen atoms, a phenyl group optionally having one or more substituents selected from Group G, a 5 membered aromatic heterocyclic group having one to four nitrogen atoms, a 6 membered aromatic heterocyclic group having one or two nitrogen atoms, $NR^{11}R^{12}$, $NR^{24}NR^{11}R^{12}$, or a halogen atom, Group G: the group consisting of a halogen atom and a C1-C6 haloalkyl group.

[10] The compound according to any one of [1] to [8], wherein $R^3$ represents a C1-C6 alkyl group optionally having one or more halogen atoms, or a halogen atom.

[11] The compound according to any one of [1] to [10], wherein $R^2$ represents an ethyl group.

[12] The compound according to [1], wherein $A^1$ represents a nitrogen atom or CH, the combination of $A^2$, $A^3$, and $A^4$ represents a combination in which $A^2$ is $CR^6$, $A^3$ is $CR^7$, and $A^4$ is $CR^8$, a combination in which $A^2$ is a nitrogen atom, $A^3$ is $CR^7$, and $A^4$ is $CR^8$, or a combination in which $A^2$ is $CR^6$, $A^3$ is a nitrogen atom, and $A^4$ is $CR^8$, $R^1$ represents a C1-C4 chain hydrocarbon group having one or more halogen atoms, or a halogen atom, $R^2$ represents a methyl group or an ethyl group, $R^3$ represents a C1-C6 alkyl group optionally having one or more halogen atoms; a phenyl group optionally having one or more substituents selected from Group G; a 5 membered aromatic heterocyclic group having one to four nitrogen atoms wherein the 5 membered aromatic heterocyclic group may optionally have one or more substituents selected from Group G; a 6 membered aromatic heterocyclic group having one or two nitrogen atoms wherein the 6 membered aromatic heterocyclic group may optionally have one or more substituents selected from Group G; $NR^{11}R^{12}$; $NR^{24}NR^{11}R^{12}$; or a halogen atom, $R^{11}$, $R^{12}$, and $R^{24}$ each independently represents a hydrogen atom, or a C1-C3 alkyl group optionally having one or more halogen atoms, $R^6$ represents a C1-C6 alkyl group optionally having one or more halogen atoms, or a halogen atom, $Het^1$ represents $Het^1$-2 or $Het^1$-4, and q represents 0 or 1, Group G: the group consisting of a halogen atom and a C1-C6 haloalkyl group.

[13] The compound according to [1], wherein. $A^1$ represents a nitrogen atom or CH, the combination of $A^2$, $A^3$, and $A^4$ represents a combination in which $A^2$ is $CR^6$, $A^3$ is $CR^7$, and $A^4$ is $CR^8$, a combination in which $A^2$ is a nitrogen atom, $A^3$ is $CR^7$, and $A^4$ is $CR^8$, or a combination in which $A^2$ is $CR^6$, $A^3$ is a nitrogen atom, and $A^4$ is $CR^8$, $R^1$ represents a C1-C4 chain hydrocarbon group having one or more halogen atoms, or a halogen atom, $R^2$ represents a methyl group or an ethyl group, $R^3$ represents a C1-C6 alkyl group optionally having one or more halogen atoms; a phenyl group optionally having one or more substituents selected from Group G; a 5 membered aromatic heterocyclic group having one to four nitrogen atoms wherein the 5 membered aromatic heterocyclic group may optionally have one or more substituents selected from Group G; a 6 membered aromatic heterocyclic group having one or two nitrogen atoms wherein the 6 membered aromatic heterocyclic group may optionally have one or more substituents selected from Group G; $NR^{11}R^{12}$; $NR^{24}NR^{11}R^{12}$; or a halogen atom, $R^{11}$, $R^{12}$, and $R^{24}$ each independently represents a hydrogen atom, or a C1-C3 alkyl group optionally having one or more halogen atoms, $R^6$, $R^7$, and $R^8$ each independently represents a hydrogen atom, a C1-C6 alkyl group optionally having one or more halogen atoms, or a halogen atom, $Het^1$ represents $Het^1$-2 or $Het^1$-4, and q represents 0 or 1.

[14] The compound according to [1], wherein $A^1$ represents a nitrogen atom or CH, the combination of $A^2$, $A^3$, and $A^4$ represents a combination in which $A^2$ is CH, $A^3$ is CH, and $A^4$ is CH, a combination in which $A^2$ is a nitrogen atom, $A^3$ is CH, and $A^4$ is CH, or a combination in which $A^2$ is CH, $A^3$ is a nitrogen atom, and $A^4$ is CH, $R^1$ represents a C1-C4 chain hydrocarbon group having one or more halogen atoms, or a halogen atom, $R^2$ represents an ethyl group, q represents 0 or 1, $R^3$ represents a C1-C6 alkyl group optionally having one or more halogen atoms, or a halogen atom, and $Het^1$ represents $Het^1$-4.

[15] A composition for controlling a harmful arthropod, comprising the compound according to any one of [1] to [14], and an inert carrier.

[16] A method for controlling a harmful arthropod, which comprises applying an effective amount of the compound according to any one of [1] to [14] to a harmful arthropod or a habitat where the harmful arthropod lives.

[17] A composition, comprising the compound according to any one of [1] to [14], and one or more ingredients selected from the group consisting of Group (a), Group (b), Group (c), and Group (d), Group (a): the group consisting of an insecticidal ingredient, a miticidal ingredient, and a nematicidal ingredient, Group (b): a fungicidal ingredient, Group (c): a plant growth modulating ingredient, Group (d): a phytotoxicity-reducing ingredient.

Effect of Invention

The present compound has an excellent control efficacy against harmful arthropods and hence is useful as an active ingredient in the agent for controlling harmful arthropods.

MODE FOR CARRYING OUT THE INVENTION

The groups as used herein are explained as follows.

The "optionally having one or more halogen atoms" as used herein represents that when two or more halogen atoms are present, the halogen atoms may be identical to or different from each other.

The expression "CX-CY" as used herein represents that the number of carbon atoms is from X to Y. For example, the expression "C1-C6" represents that the number of carbon atoms is from 1 to 6.

The term "halogen atom" represents a fluorine atom, a chlorine atom, a bromine atom, or an iodine atom.

The term "chain hydrocarbon group" represents an alkyl group, an alkenyl group, or an alkynyl group.

Examples of the "alkyl group" include methyl group, ethyl group, propyl group, isopropyl group, 1,1-dimethylpropyl group, 1,2-dimethylpropyl group, 1-ethylpropyl group, butyl group, tert-butyl group, pentyl group, and hexyl group.

Examples of the "alkenyl group" include vinyl group, 1-propenyl group, 2-propenyl group, 1-methyl-1-propenyl group, 1-methyl-2-propenyl group, 1,2-dimethyl-1-propenyl group, 1,1-dimethyl-2-propenyl group, 3-butenyl group, 4-pentenyl group, and 5-hexenyl group.

Examples of the "alkynyl group" include ethynyl group, 1-propynyl group, 2-propynyl group, 1-methyl-2-propynyl group, 1,1-dimethyl-2-propynyl group, 4-pentynyl group, and 5-hexynyl group.

The term "C1-C6 haloalkyl group" represents a group wherein hydrogen atoms in the C1-C6 alkyl group are substituted by halogen atoms, and includes, for example, C1-C6 fluoroalkyl group.

Examples of the "C1-C6 haloalkyl group" include chloroethyl group, 2,2,2-trifluoroethyl group, 2-bromo-1,1,2,2-tetrafluoroethyl group, 2,2,3,3-tetrafluoropropyl group, 1-methyl-2,2,3,3-tetrafluoropropyl group, and perfluorohexyl group.

Examples of the "C1-C6 fluoroalkyl group" include 2,2,2-trifluoroethyl group, 2,2,3,3-tetrafluoropropyl group, 1-methyl-2,2,3,3-tetrafluoropropyl group, and perfluorohexyl group.

Examples of the "cycloalkyl group" include cyclopropyl group, cyclobutyl group, cyclopentyl group, cyclohexyl group, and cycloheptyl group.

The term "3-7 membered nonaromatic heterocyclic group" represents aziridine ring, azetidine ring, pyrrolidine ring, imidazoline ring, imidazolidine ring, piperidine ring, tetrahydropyrimidine ring, hexahydropyrimidine ring, piperazine ring, azepane ring, oxazolidine ring, isoxazolidine ring, 1,3-oxazinane ring, morpholine ring, 1,4-oxazepane ring, thiazolidine ring, isothiazolidine ring, 1,3-thiadinane ring, thiomorpholine ring, or 1,4-thiazepane ring, and examples of the 3-7 membered nonaromatic heterocyclic group optionally having one or more substituents selected from Group E include the following groups.

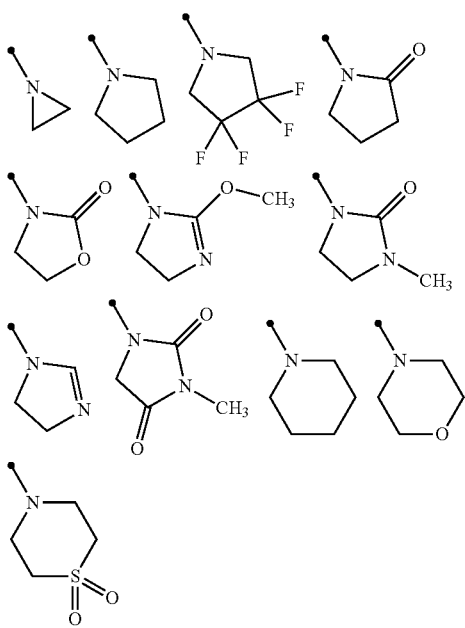

Examples of the "phenyl C1-C3 alkyl group wherein the phenyl moiety in the phenyl C1-C3 alkyl group may optionally have one or more substituents selected from Group D" include benzyl group, 2-fluorobenzyl group, 4-chlorobenzyl group, 4-(trifluoromethyl)benzyl group, and 2-[4-(trifluoromethyl)phenyl]ethyl group.

The "(C3-C6 cycloalkyl)C1-C3 alkyl group optionally having one or more halogen atoms" represents a group wherein the (C3-C6 cycloalkyl) moiety and/or the (C1-C3 alkyl) moiety may optionally have one or more halogen atoms, and includes, for example, (2,2-difluorocyclopropyl)methyl group, 2-cyclopropyl-1,1,2,2-tetrafluoroethyl group, and 2-(2,2-difluorocyclopropyl)-1,1,2,2-tetrafluoroethyl group.

The term "5 or 6 membered aromatic heterocyclic group" represents a 5 membered aromatic heterocyclic group or a 6 membered aromatic heterocyclic group. The 5 membered aromatic heterocyclic group includes pyrrolyl group, furyl group, thienyl group, pyrazolyl group, imidazolyl group, triazolyl group, tetrazolyl group, oxazolyl group, isoxazolyl group, triazolyl group, oxadiazolyl group, or thiadiazolyl group. The 5 membered aromatic heterocyclic group is preferably a 5 membered aromatic heterocyclic group having one to four nitrogen atoms, i.e. pyrrolyl group, pyrazolyl group, imidazolyl group, 1,2,4-triazolyl group, 1,2,3-triazolyl group, or tetrazolyl group. The 6 membered aromatic heterocyclic group includes pyridyl group, pyridazinyl group, pyrimidinyl group, or pyrazinyl group. The 6 membered aromatic heterocyclic group is preferably a 6 membered aromatic heterocyclic group having one or two nitrogen atoms, i.e. pyridyl group, pyridazinyl group, pyrimidinyl group, or pyrazinyl group.

In the present compound, the structure represented by the following formula:

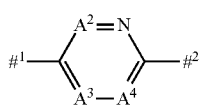

(hereinafter, referred to as "Het²"), wherein #¹ represents a position of attachment to Het¹, and #² represents a position of attachment to

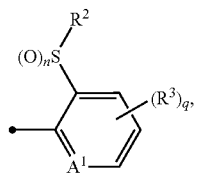

represents the following Het²-1, Het²-2, Het²-3, or Het²-4:

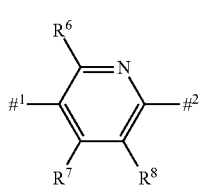

Het²-1

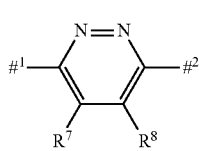

Het²-2

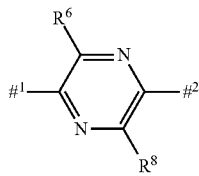

Het²-3

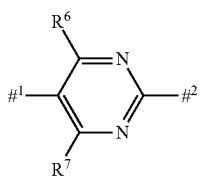

wherein the symbols are the same as defined above.

The "N-oxide compound" represents a compound represented by formula (N-1), a compound represented by formula (N-2), a compound represented by formula (N-3), a compound represented by formula (N-4), a compound represented by formula (N-5), or a compound represented by formula (N-6).

(N-1)

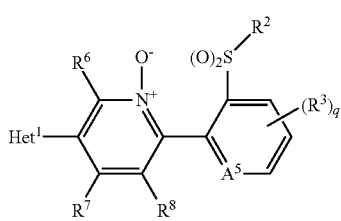

(N-2)

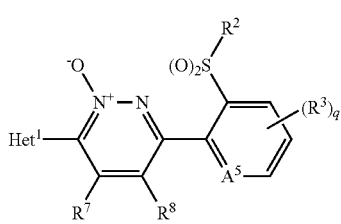

(N-3)

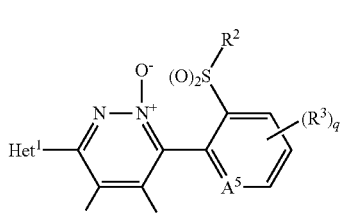

(N-4)

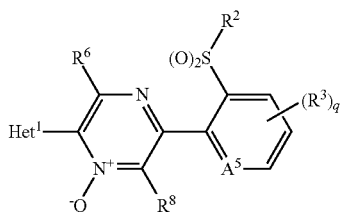

(N-5)

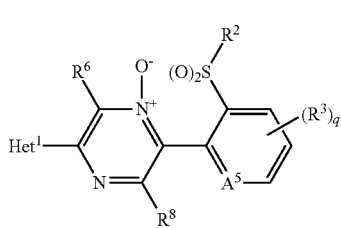

(N-6)

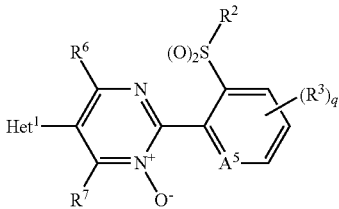

wherein $A^5$ represents a nitrogen atom, $N^+O^-$, or $CR^9$, and the other symbols are the same as defined above.

Embodiments of the present compound include the following compounds.

Embodiment 1

A present compound wherein $R^1$ represents a C1-C4 chain hydrocarbon group having one or more halogen atoms, or a halogen atom;

Embodiment 2

A present compound wherein $R^1$ and $R^{1a}$ each independently represents a C1-C4 alkyl group having three or more fluorine atoms;

Embodiment 3

A present compound wherein $R^2$ represents a C1-C3 alkyl group optionally having one or more halogen atoms, a cyclopropyl group, or a cyclopropylmethyl group;

Embodiment 4

A present compound wherein $R^2$ represents a methyl group, an ethyl group, a cyclopropyl group, or a cyclopropylmethyl group;

Embodiment 5

A present compound wherein $R^2$ represents a methyl group or an ethyl group;

Embodiment 6

A present compound wherein $R^2$ represents an ethyl group;

Embodiment 7

A present compound wherein $R^3$ represents a C1-C6 chain hydrocarbon group optionally having one or more substituents selected from Group B; a phenyl group optionally having one or more substituents selected from Group D; a 6 membered aromatic heterocyclic group selected from Group V wherein the 6 membered aromatic heterocyclic group may optionally have one or more substituents selected from Group D; a 5 membered aromatic heterocyclic group selected from Group W wherein the 5 membered aromatic heterocyclic group may optionally have one or more substituents selected from Group D; $OR^{12}$; $NR^{11}R^{12}$; $NR^{11a}R^{12a}$; $NR^{24}NR^{11}R^{12}$; or a halogen atom;

Group V:
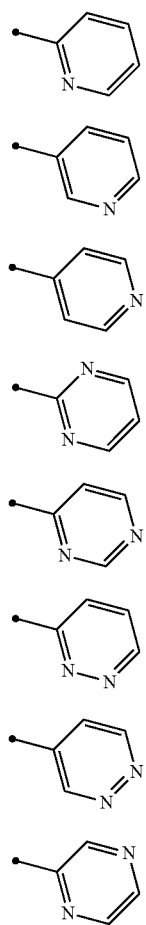
Group W:
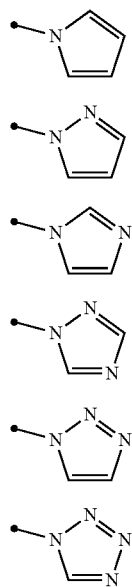
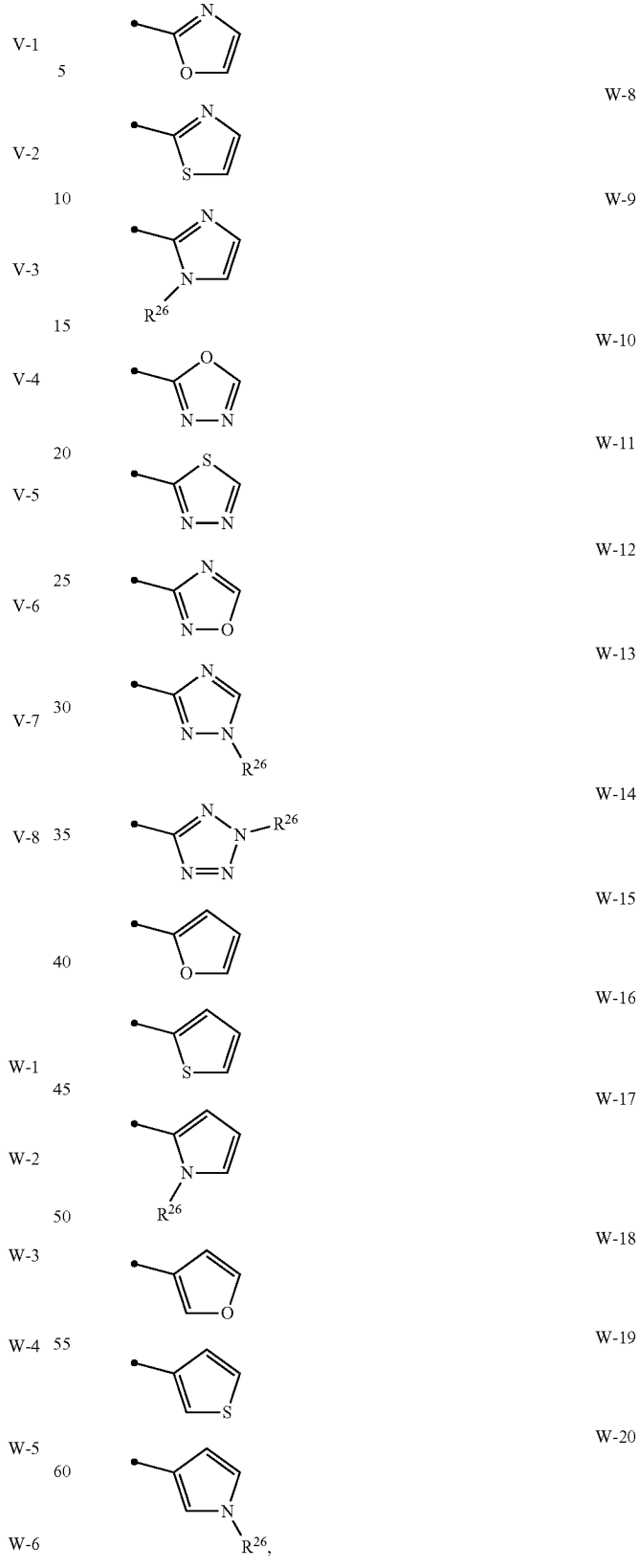
wherein $R^{26}$ represents a C1-C6 alkyl group optionally having one or more halogen atoms;

Embodiment 8

A present compound wherein $R^3$ represents a C1-C6 alkyl group optionally having one or more halogen atoms; a phenyl group optionally having one or more substituents selected from Group G; a 6 membered aromatic heterocyclic group selected from Group V wherein the 6 membered aromatic heterocyclic group may optionally have one or more substituents selected from Group G; a 5 membered aromatic heterocyclic group selected from W-1 to W-6 wherein the 5 membered aromatic heterocyclic group may optionally have one or more substituents selected from Group G; $NR^{11}R^{12}$; $NR^{24}NR^{11}R^{12}$; or a halogen atom, and $R^{11}$, $R^{12}$, and $R^{24}$ each independently represents a hydrogen atom, or a C1-C3 alkyl group optionally having one or more halogen atoms;

Embodiment 9

A present compound wherein $R^3$ represents a C1-C6 chain hydrocarbon group optionally having one or more halogen atoms, or a halogen atom;

Embodiment 10

A present compound wherein $R^3$ represents a C1-C6 alkyl group having one or more halogen atoms, or a halogen atom;

Embodiment 11

A present compound wherein $R^6$ represents a hydrogen atom, a C1-C6 alkyl group optionally having one or more halogen atoms, or a halogen atom;

Embodiment 12

A present compound wherein q represents 0 or 1;

Embodiment 13

A present compound wherein q represents 0;

Embodiment 14

A present compound wherein $A^1$ represents a nitrogen atom or $CR^9$, and $R^4$ represents a hydrogen atom or a halogen atom;

Embodiment 15

A present compound wherein $A^1$ represents a nitrogen atom or CH;

Embodiment 16

A present compound wherein $A^1$ represents a nitrogen atom;

Embodiment 17

A present compound wherein $Het^1$ represents $Het^1$-1, $Het^1$-2, $Het^1$-3, or $Het^1$-4;

Embodiment 18

A present compound wherein $Het^1$ represents $Het^1$-1, $Het^1$-2, or $Het^1$-3;

Embodiment 19

A present compound wherein $Het^1$ represents $Het^1$-2 or $Het^1$-4;

Embodiment 20

A present compound wherein $Het^1$ represents $Het^1$-4;

Embodiment 21

A present compound wherein $Het^2$ represents $Het^2$-1, $Het^2$-2, or $Het^2$-3;

Embodiment 22

A present compound wherein $Het^2$ represents $Het^2$-1;

Embodiment 23

A present compound wherein $Het^2$ represents $Het^2$-2;

Embodiment 24

A present compound wherein $Het^2$ represents $Het^2$-3;

Embodiment 25

A present compound wherein $Het^2$ represents $Het^2$-4;

Embodiment 26

A present compound wherein $A^1$ represents a nitrogen atom or CH, $R^1$ represents a C1-C4 chain hydrocarbon group having one or more halogen atoms, or a halogen atom, $R^2$ represents a C1-C3 alkyl group optionally having one or more halogen atoms, a cyclopropyl group, or a cyclopropylmethyl group, $R^3$ represents a C1-C6 chain hydrocarbon group optionally having one or more substituents selected from Group B; a phenyl group optionally having one or more substituents selected from Group D; a 6 membered aromatic heterocyclic group selected from Group V wherein the 6 membered aromatic heterocyclic group may optionally have one or more substituents selected from Group D; a 5 membered aromatic heterocyclic group selected from Group W wherein the 5 membered aromatic heterocyclic group may optionally have one or more substituents selected from Group D; $OR^{12}$; $NR^{11}R^{12}$; $NR^{11a}R^{12a}$; $NR^{24}NR^{11}R^{12}$; or a halogen atom, and $R^6$ represents a hydrogen atom, a C1-C6 alkyl group optionally having one or more halogen atoms, or a halogen atom;

Embodiment 27

A present compound wherein $A^1$ represents a nitrogen atom or CH, $R^1$ and $R^{1a}$ each independently represents a C1-C4 alkyl group having three or more fluorine atoms, $R^2$ represents a C1-C3 alkyl group optionally having one or more halogen atoms, a cyclopropyl group, or a cyclopropylmethyl group, $R^3$ represents a C1-C6 chain hydrocarbon group optionally having one or more substituents selected from Group B; a phenyl group optionally having one or more substituents selected from Group D; a 6 membered aromatic heterocyclic group selected from Group V wherein the 6 membered aromatic heterocyclic group may optionally have one or more substituents selected from Group D; a 5 membered aromatic heterocyclic group selected from Group W wherein the 5 membered aromatic heterocyclic group may optionally have one or more substituents selected from Group D; $OR^{12}$; $NR^{11}R^{12}$; $NR^{11a}R^{12a}$; $NR^{24}NR^{11}R^{12}$; or a halogen atom, and $R^6$ represents a hydrogen atom, a C1-C6 alkyl group optionally having one or more halogen atoms, or a halogen atom;

Embodiment 28

A present compound wherein $A^1$ represents a nitrogen atom or CH, $R^1$ and $R^{1a}$ each independently represents a C1-C4 alkyl group having three or more fluorine atoms, $R^2$ represents a methyl group or an ethyl group, $R^3$ represents a C1-C6 alkyl group optionally having one or more halogen atoms; a phenyl group optionally having one or more substituents selected from Group G; a 6 membered aromatic heterocyclic group selected from Group V wherein the 6 membered aromatic heterocyclic group may optionally have one or more substituents selected from Group G; a 5 membered aromatic heterocyclic group selected from W-1 to W-6 wherein the 5 membered aromatic heterocyclic group may optionally have one or more substituents selected from Group G; $NR^{11}R^{12}$; $NR^{24}NR^{11}R^{12}$; or a halogen atom, $R^{11}$, $R^{12}$, and $R^{24}$ each independently represents a hydrogen atom, or a C1-C3 alkyl group optionally having one or more halogen atoms, and $R^6$ represents a hydrogen atom, a C1-C6 alkyl group optionally having one or more halogen atoms, or a halogen atom;

Embodiment 29

A present compound wherein $A^1$ represents a nitrogen atom or CH, $R^1$ and $R^{1a}$ each independently represents a C1-C4 alkyl group having three or more fluorine atoms, $R^2$ represents an ethyl group, $R^3$ represents a C1-C6 chain hydrocarbon group optionally having one or more halogen atoms, or a halogen atom, and $R^6$ represents a C1-C6 alkyl group optionally having one or more halogen atoms, or a halogen atom;

Embodiment 30

A present compound wherein $A^1$ represents a nitrogen atom, $R^1$ and $R^{1a}$ each independently represents a C1-C4 alkyl group having three or more fluorine atoms, $R^2$ represents an ethyl group, $R^3$ represents a C1-C6 chain hydrocarbon group optionally having one or more halogen atoms, or a halogen atom, and $R^6$ represents a hydrogen atom, a C1-C6 alkyl group optionally having one or more halogen atoms, or a halogen atom;

Embodiment 31

A present compound wherein $A^1$ represents a nitrogen atom or CH, $R^1$ and $R^{1a}$ each independently represents a C1-C4 alkyl group having three or more fluorine atoms, $R^2$ represents an ethyl group, $R^3$ represents a C1-C6 chain hydrocarbon group optionally having one or more substituents selected from Group B; a phenyl group optionally having one or more substituents selected from Group D; a 6 membered aromatic heterocyclic group selected from Group V wherein the 6 membered aromatic heterocyclic group may optionally have one or more substituents selected from Group D; a 5 membered aromatic heterocyclic group selected from Group W wherein the 5 membered aromatic heterocyclic group may optionally have one or more substituents selected from Group D; $OR^{12}$; $NR^{11}R^{12}$; $NR^{11a}R^{12a}$; $NR^{24}NR^{11}R^{12}$; or a halogen atom, and $R^6$ represents a hydrogen atom, a C1-C6 alkyl group optionally having one or more halogen atoms, or a halogen atom;

Embodiment 32

A present compound wherein $A^1$ represents a nitrogen atom or CH, $R^1$ and $R^{1a}$ each independently represents a C1-C4 alkyl group having three or more fluorine atoms, $R^2$ represents an ethyl group, $R^3$ represents a C1-C6 alkyl group optionally having one or more halogen atoms; a phenyl group optionally having one or more substituents selected from Group G; a 6 membered aromatic heterocyclic group selected from Group V wherein the 6 membered aromatic heterocyclic group may optionally have one or more substituents selected from Group G; a 5 membered aromatic heterocyclic group selected from W-1 to W-6 wherein the 5 membered aromatic heterocyclic group may optionally have one or more substituents selected from Group G; $NR^{11}R^{12}$; $NR^{24}NR^{11}R^{12}$; or a halogen atom, $R^{11}$, $R^{12}$, and $R^{24}$ each independently represents a hydrogen atom, or a C1-C3 alkyl group optionally having one or more halogen atoms, and $R^6$ represents a hydrogen atom, a C1-C6 alkyl group optionally having one or more halogen atoms, or a halogen atom;

Embodiment 33

The compound according to any of [Embodiment 28] to [Embodiment 32], wherein $Het^1$ represents $Het^1$-1, $Het^1$-2, $Het^1$-3, or $Het^1$-4, and $Het^2$ represents $Het^2$-1, $Het^2$-2, or $Het^2$-3;

Embodiment 34

The compound according to any of [Embodiment 28] to [Embodiment 32], wherein $Het^1$ represents $Het^1$-1, $Het^1$-2, $Het^1$-3, or $Het^1$-4, and $Het^2$ represents $Het^2$-1;

Embodiment 35

The compound according to any of [Embodiment 28] to [Embodiment 32], wherein $Het^1$ represents $Het^1$-1, $Het^1$-2, $Het^1$-3, or $Het^1$-4, and $Het^2$ represents $Het^2$-2;

Embodiment 36

The compound according to any of [Embodiment 28] to [Embodiment 32], wherein $Het^1$ represents $Het^1$-1, $Het^1$-2, $Het^1$-3, or $Het^1$-4, and $Het^2$ represents $Het^2$-3;

Embodiment 37

The compound according to any of [Embodiment 28] to [Embodiment 32], wherein $Het^1$ represents $Het^1$-1, $Het^1$-2, $Het^1$-3, or $Het^1$-4, and $Het^2$ represents $Het^2$-4;

Embodiment 38

The compound according to any of [Embodiment 28] to [Embodiment 32], wherein $Het^1$ represents $Het^1$-4, and $Het^2$ represents $Het^2$-1, $Het^2$-2, or $Het^2$-3;

Embodiment 39

The compound according to any of [Embodiment 28] to [Embodiment 32], wherein $Het^1$ represents $Het^1$-4, and $Het^2$ represents $Het^2$-1;

Embodiment 40

The compound according to any of [Embodiment 28] to [Embodiment 32], wherein Het$^1$ represents Het$^1$-4, and Het$^2$ represents Het$^2$-2;

Embodiment 41

The compound according to any of [Embodiment 28] to [Embodiment 32], wherein Het$^1$ represents Het$^1$-4, and Het$^2$ represents Het$^2$-3;

Embodiment 42

The compound according to any of [Embodiment 28] to [Embodiment 32], wherein Het$^1$ represents Het$^1$-4, and Het$^2$ represents Het$^2$-4;

Embodiment 43

A present compound wherein A$^1$ represents a nitrogen atom, R$^1$ represents a C1-C4 chain hydrocarbon group having one or more halogen atoms, or a halogen atom, R$^2$ represents an ethyl group, R$^3$ represents a C1-C6 alkyl group optionally having one or more halogen atoms, or a halogen atom, Het$^1$ represents Het$^1$-4, Het$^2$ represents Het$^2$-1, Het$^2$-2, or Het$^2$-3, R$^6$, R$^7$, and R$^8$ represent a hydrogen atom, and q represents 0 or 1;

Embodiment 44

The compound according to [Embodiment 43], wherein Het$^2$ represents Het$^2$-1;

Embodiment 45

The compound according to [Embodiment 43], wherein Het$^2$ represents Het$^2$-2;

Embodiment 46

The compound according to [Embodiment 43], wherein Het$^2$ represents Het$^2$-3;

Embodiment 47

The compound according to [Embodiment 44], wherein X$^2$ represents a nitrogen atom, X$^3$ represents CH, and X$^4$ represents CH;

Embodiment 48

The compound according to [Embodiment 44], wherein X$^2$ represents CH;

Embodiment 49

The compound according to [Embodiment 45], wherein X$^2$ represents a nitrogen atom, and X$^4$ represents CH;

Embodiment 50

The compound according to [Embodiment 45], wherein X$^2$ represents CH; X$^3$ represents a nitrogen atom, and X$^4$ represents CH;

Embodiment 51

The compound according to [Embodiment 46], wherein X$^4$ represents CH;

Embodiment 52

The compound according to [Embodiment 46], wherein X$^2$ represents a nitrogen atom, and X$^4$ represents CH;

Embodiment 53

A present compound wherein R$^6$, R$^7$, and R$^8$ each independently represents a hydrogen atom, a C1-C6 alkyl group optionally having one or more halogen atoms, or a halogen atom;

Embodiment 54

A present compound wherein A$^1$ represents a nitrogen atom or CH, R$^1$ represents a C1-C4 chain hydrocarbon group having one or more halogen atoms, or a halogen atom, R$^2$ represents a C1-C3 alkyl group optionally having one or more halogen atoms, a cyclopropyl group, or a cyclopropylmethyl group, R$^3$ represents a C1-C6 chain hydrocarbon group optionally having one or more substituents selected from Group B; a phenyl group optionally having one or more substituents selected from Group D; a 6 membered aromatic heterocyclic group selected from Group V wherein the 6 membered aromatic heterocyclic group may optionally have one or more substituents selected from Group D; a 5 membered aromatic heterocyclic group selected from Group W wherein the 5 membered aromatic heterocyclic group may optionally have one or more substituents selected from Group D; OR$^{12}$; NR$^{11}$R$^{12}$; NR$^{11a}$R$^{12a}$; NR$^{24}$NR$^{11}$R$^{12}$; or a halogen atom, and R$^6$, R$^7$, and R$^8$ each independently represents a hydrogen atom, a C1-C6 alkyl group optionally having one or more halogen atoms, or a halogen atom;

Embodiment 55

A present compound wherein A$^1$ represents a nitrogen atom or CH, R$^1$ and R$^{1a}$ each independently represents a C1-C4 alkyl group having three or more fluorine atoms, R$^2$ represents a methyl group or an ethyl group, R$^3$ represents a C1-C6 alkyl group optionally having one or more halogen atoms; a phenyl group optionally having one or more substituents selected from Group G; a 6 membered aromatic heterocyclic group selected from Group V wherein the 6 membered aromatic heterocyclic group may optionally have one or more substituents selected from Group G; a 5 membered aromatic heterocyclic group selected from W-1 to W-6 wherein the 5 membered aromatic heterocyclic group may optionally have one or more substituents selected from Group G; NR$^{11}$R$^{12}$; NR$^{24}$NR$^{11}$R$^{12}$; or a halogen atom, R$^{11}$, R$^{12}$, and R$^{24}$ each independently represents a hydrogen atom, or a C1-C3 alkyl group optionally having one or more halogen atoms, and R$^6$, R$^7$, and R$^8$ each independently represents a hydrogen atom, a C1-C6 alkyl group optionally having one or more halogen atoms, or a halogen atom;

Embodiment 56

A present compound wherein A$^1$ represents a nitrogen atom or CH, R$^1$ and R$^{1a}$ each independently represents a C1-C4 alkyl group having three or more fluorine atoms, R$^2$ represents an ethyl group, R$^3$ represents a C1-C6 chain hydrocarbon group optionally having one or more halogen atoms, or a halogen atom, and $R^6$, $R^7$, and $R^8$ each independently represents a hydrogen atom, a C1-C6 alkyl group optionally having one or more halogen atoms, or a halogen atom;

Embodiment 57

A present compound wherein $A^1$ represents a nitrogen atom, $R^1$ and $R^{1a}$ each independently represents a C1-C4 alkyl group having three or more fluorine atoms, $R^2$ represents an ethyl group, $R^3$ represents a C1-C6 chain hydrocarbon group optionally having one or more halogen atoms, or a halogen atom, and $R^6$, $R^7$, and $R^8$ each independently represents a hydrogen atom, a C1-C6 alkyl group optionally having one or more halogen atoms, or a halogen atom;

Embodiment 58

A present compound wherein $A^1$ represents a nitrogen atom or CH, $R^1$ and $R^{1a}$ each independently represents a C1-C4 alkyl group having three or more fluorine atoms, $R^2$ represents an ethyl group, $R^3$ represents a C1-C6 chain hydrocarbon group optionally having one or more substituents selected from Group B; a phenyl group optionally having one or more substituents selected from Group D; a 6 membered aromatic heterocyclic group selected from Group V wherein the 6 membered aromatic heterocyclic group may optionally have one or more substituents selected from Group D; a 5 membered aromatic heterocyclic group selected from Group W wherein the 5 membered aromatic heterocyclic group may optionally have one or more substituents selected from Group D; $OR^{12}$; $NR^{11}R^{12}$; $NR^{11a}R^{12a}$; $NR^{24}NR^{11}R^{12}$; or a halogen atom, and $R^6$, $R^7$, and $R^8$ each independently represents a hydrogen atom, a C1-C6 alkyl group optionally having one or more halogen atoms, or a halogen atom;

Embodiment 59

A present compound wherein $A^1$ represents a nitrogen atom or CH, $R^1$ and $R^{1a}$ each independently represents a C1-C4 alkyl group having three or more fluorine atoms, $R^2$ represents an ethyl group, $R^3$ represents a C1-C6 alkyl group optionally having one or more halogen atoms; a phenyl group optionally having one or more substituents selected from Group G; a 6 membered aromatic heterocyclic group selected from Group V wherein the 6 membered aromatic heterocyclic group may optionally have one or more substituents selected from Group G; a 5 membered aromatic heterocyclic group selected from W-1 to W-6 wherein the 5 membered aromatic heterocyclic group may optionally have one or more substituents selected from Group G; $NR^{11}R^{12}$; $NR^{24}NR^{11}R^{12}$; or a halogen atom, $R^{11}$, $R^{12}$, and $R^{24}$ each independently represents a hydrogen atom, or a C1-C3 alkyl group optionally having one or more halogen atoms, and $R^6$, $R^7$, and $R^8$ each independently represents a hydrogen atom, a C1-C6 alkyl group optionally having one or more halogen atoms, or a halogen atom;

Embodiment 60

The compound according to any of [Embodiment 55] to [Embodiment 59], wherein $Het^1$ represents $Het^1$-1, $Het^1$-2, $Het^1$-3, or $Het^1$-4, and $Het^2$ represents $Het^2$-1, $Het^2$-2, or $Het^2$-3;

Embodiment 61

The compound according to any of [Embodiment 55] to [Embodiment 59], wherein $Het^1$ represents $Het^1$-1, $Het^1$-3, or $Het^1$-4, and $Het^2$ represents $Het^2$-1;

Embodiment 62

The compound according to any of [Embodiment 55] to [Embodiment 59], wherein $Het^1$ represents $Het^1$-1, $Het^1$-2, $Het^1$-3, or $Het^1$-4, and $Het^2$ represents $Het^2$-2;

Embodiment 63

The compound according to any of [Embodiment 55] to [Embodiment 59], wherein $Het^1$ represents $Het^1$-1, $Het^1$-2, $Het^1$-3, or $Het^1$-4, and $Het^2$ represents $Het^2$-3;

Embodiment 64

The compound according to any of [Embodiment 55] to [Embodiment 59], wherein $Het^1$ represents $Het^1$-1, $Het^1$-2, $Het^1$-3, or $Het^1$-4, and $Het^2$ represents $Het^2$-4;

Embodiment 65

The compound according to any of [Embodiment 55] to [Embodiment 59], wherein $Het^1$ represents $Het^1$-4, and $Het^2$ represents $Het^2$-1, $Het^2$-2, or $Het^2$-3;

Embodiment 66

The compound according to any of [Embodiment 55] to [Embodiment 59], wherein $Het^1$ represents $Het^1$-4, and $Het^2$ represents $Het^2$-1;

Embodiment 67

The compound according to any of [Embodiment 55] to [Embodiment 59], wherein $Het^1$ represents $Het^1$-4, and $Het^2$ represents $Het^2$-2;

Embodiment 68

The compound according to any of [Embodiment 55] to [Embodiment 59], wherein $Het^1$ represents $Het^1$-4, and $Het^2$ represents $Het^2$-3;

Embodiment 69

The compound according to any of [Embodiment 55] to [Embodiment 59], wherein $Het^1$ represents $Het^1$-4, and $Het^2$ represents $Het^2$-4.

Next, a process for preparing the present compound is described.

The present compounds and their intermediate compounds can be prepared according to the following processes.

Process 1

The present compound wherein n represents 1 (hereinafter, referred to as "compound (1-n1)") or the present compound wherein n represents 2 (hereinafter, referred to as "compound (1-n2)") can be prepared by oxidizing the present compound wherein n represents 0 (hereinafter, referred to as "compound (1-n0)").

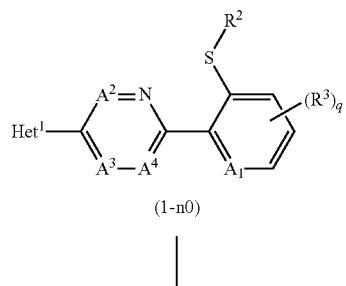 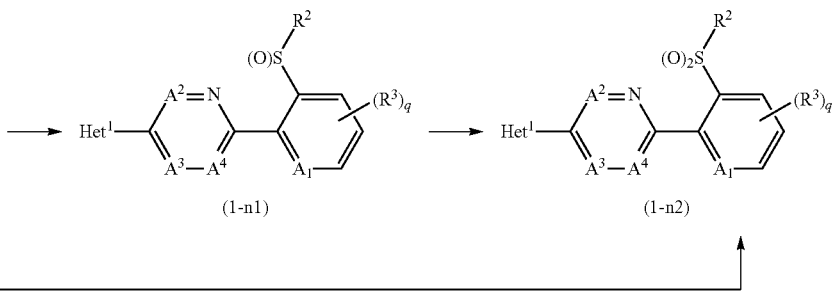

wherein the symbols are the same as those defined above.

Firstly, a process for preparing the compound (1-n1) from the compound (1-n0) is described.

The reaction is usually carried out in a solvent.

Examples of the solvent to be used in the reaction include halogenated aliphatic hydrocarbons (hereinafter, collectively referred to as "halogenated aliphatic hydrocarbons") such as dichloromethane and chloroform; nitriles (hereinafter, collectively referred to "nitriles") such as acetonitrile; alcohols (hereinafter, collectively referred to as "alcohols") such as methanol and ethanol; acetic acid; water; and mixed solvents thereof.

Examples of the oxidizing agent to be used in the reaction include sodium periodate, m-chloroperoxybenzoic acid (hereinafter, referred to as "mCPBA"), and hydrogen peroxide.

When hydrogen peroxide is used as the oxidizing agent, sodium carbonate or a catalyst may be added as needed.

Examples of the catalyst to be used in the reaction include tungstic acid and sodium tungstate.

In the reaction, the oxidizing agent is used usually within a range of 1 to 1.2 molar ratio(s), a base is used usually within a range of 0.01 to 1 molar ratio(s), and the catalyst is used usually within a range of 0.01 to 0.5 molar ratios, relative to 1 mole of the compound (1-n0).

A reaction temperature in the reaction is usually within a range of –20 to 80° C. A reaction period in the reaction is usually within a range of 0.1 to 12 hours.

When the reaction is completed, to the reaction mixture is added water, and the reaction mixture is extracted with an organic solvent. The organic layer is sequentially washed with an aqueous solution of a reducing agent such as sodium sulfite and sodium thiosulfate, and an aqueous solution of a base such as sodium hydrogen carbonate as needed. The resulting organic layer can be dried and concentrated to give the compound (1-n1).

Next, a process for preparing the compound (1-n2) from the compound (1-n1) is described.

The reaction is usually carried out in a solvent.

Examples of the solvent to be used in the reaction include halogenated aliphatic hydrocarbons, nitriles, alcohols, acetic acid, water, and mixed solvents thereof.

Examples of the oxidizing agent to be used in the reaction include mCPBA and hydrogen peroxide.

When hydrogen peroxide is used as the oxidizing agent, a base or catalyst may be added as needed.

Examples of the base to be used in the reaction include sodium carbonate.

Examples of the catalyst to be used in the reaction include sodium tungstate.

In the reaction, the oxidizing agent is used usually within a range of 1 to 2 molar ratio(s), the base is used usually within a range of 0.01 to 1 molar ratio(s), and catalyst is used usually within a range of 0.01 to 0.5 molar ratios, relative to 1 mole of the compound (1-n1).

A reaction temperature in the reaction is usually within a range of –20 to 120° C. A reaction period in the reaction is usually within a range of 0.1 to 12 hours.

When the reaction is completed, to the reaction mixture is added water, and the reaction mixture is then extracted with an organic solvent. The organic layer is washed sequentially with an aqueous solution of a reducing agent such as sodium sulfite and sodium thiosulfate, and an aqueous solution of a base such as sodium hydrogen carbonate as needed. The resulting organic layer is dried and concentrated to give the compound (1-n2).

Also, the compound (1-n2) may be prepared in one step (one-pot) by reacting the compound (1-n0) with an oxidizing agent.

The reaction may be carried out according to the process for preparing the compound (1-n2) from the compound (1-n1) using the oxidizing agent usually in 2 to 5 molar ratios relative to 1 mole of the compound (1-n0).

Process 2

The compound (1-n0) may be prepared by reacting a compound represented by formula (M-1) (hereinafter, referred to as "compound (M-1)") with a compound represented by formula (R-1) (hereinafter, referred to as "compound (R-1)") in the presence of a base.

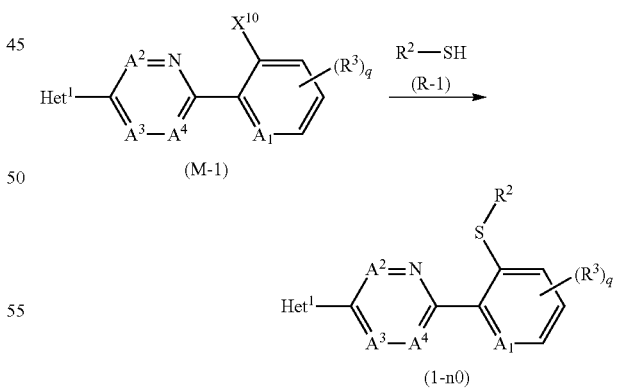

wherein $X^{10}$ represents a halogen atom, and the other symbols are the same as those defined above.

The reaction is usually carried out in a solvent.

Examples of the solvent to be used in the reaction include ethers (hereinafter, collectively referred to as "ethers") such as tetrahydrofuran (hereinafter, referred to as "THF"), ethyleneglycol dimethyl ether (hereinafter, referred to as "DME"), methyl tert-butyl ether (hereinafter, referred to as "MTBE") and 1,4-dioxane; aromatic hydrocarbons (hereinafter, collectively referred to as "aromatic hydrocarbons") such as toluene and xylene; nitriles; polar aprotic solvents (hereinafter, collectively referred to as "polar aprotic solvents") such as dimethylformamide (hereinafter, referred to as "DMF"), N-methyl pyrrolidone (hereinafter, referred to as "NMP") and dimethyl sulfoxide; and mixed solvents thereof.

Examples of the base to be used in the reaction include alkali metal carbonates (hereinafter, correctively referred to as "alkali metal carbonates") such as sodium carbonate and potassium carbonate; and alkali metal hydrides (hereinafter, collectively referred to as "alkali metal hydrides") such as sodium hydride.

In the reaction, the compound (R-1) is used usually within a range of 1 to 10 molar ratio(s), and the base is used usually within a range of 1 to 10 molar ratio(s), relative to 1 mole of the compound (M-1).

A reaction temperature in the reaction is usually within a range of −20 to 150° C. A reaction period in the reaction is usually within a range of 0.5 to 24 hours.

When the reaction is completed, to the reaction mixture is added water, and the reaction mixture is extracted with an organic solvent. The organic layer can be worked up (for example, drying and concentration) to give the compound (1-n0).

In the reaction, $X^{10}$ is preferably a fluorine atom or a chlorine atom.

Process 3

A compound represented by formula (1a) (hereinafter, referred to as "compound (1a)") may be prepared by reacting a compound represented by formula (M-3) (hereinafter, referred to as "compound (M-3)") with a compound represented by formula (R-2) (hereinafter, referred to as "compound (R-2)") in the presence of a metal catalyst.

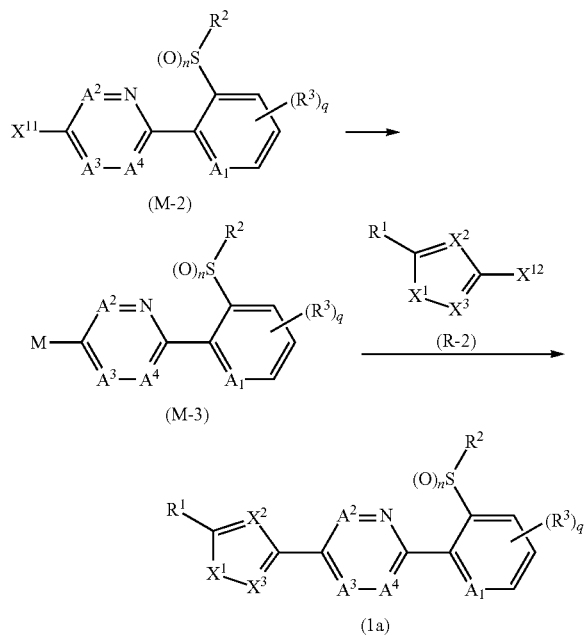

wherein $X^{11}$ represents a bromine atom or an iodine atom, $X^{12}$ represents a chlorine atom, a bromine atom, or an iodine atom, M represents 9-borabicyclo[3.3.1]nonane-9-yl group, —B(OH)$_2$, 4,4,5,5-tetramethyl-1,3,2-dioxaborolan-2-yl group, Sn(n-C$_4$H$_9$)$_3$, ZnCl, MgCl, or MgBr, and the other symbols are the same as those defined above.

Firstly, a process for preparing the compound (1a) from the compound (M-3) and the compound (R-2) is described.

The reaction is usually carried out in a solvent.

Examples of the solvent to be used in the reaction include ethers, aromatic hydrocarbons, polar aprotic solvents, water, and mixed solvents thereof.

Examples of the metal catalyst to be used in the reaction include palladium catalysts such as tetrakis(triphenylphosphine)palladium(0), [1,1'-bis(diphenylphosphino)ferrocene]palladium(II) dichloride, tris(dibenzylideneacetone)dipalladium(0) and palladium(II) acetate; nickel catalysts such as bis(cyclooctadiene)nickel(0) and nickel(II) chloride; and copper catalysts such as copper(I) iodide and copper(I) chloride.

A ligand, a base, or an inorganic halide may be added in the reaction as needed.

Examples of the ligand to be used in the reaction include triphenylphosphine, xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline.

Examples of the base to be used in the reaction include alkali metal hydrides, alkali metal carbonates, and organic bases.

Examples of the inorganic halides to be used in the reaction include alkali metal fluorides such as potassium fluoride and sodium fluoride; and alkali metal chlorides such as lithium chloride and sodium chloride.

In the reaction, the compound (M-3) is used usually within a range of 1 to 10 molar ratio(s), the metal catalyst is used usually within a range of 0.01 to 0.5 molar ratios, the ligand is used usually within a range of 0.01 to 1 molar ratio(s), and the base is used usually within a range of 0.1 to 5 molar ratios, relative to 1 mole of the compound (R-2).

A reaction temperature in the reaction is usually within a range of −20 to 200° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (1a).

The compound (R-2) is commercially available, or can be prepared according to a known method.

The compound (M-3) may be prepared according to a similar method to that described in International Publication No. WO06/097691, or The Journal Of Organic Chemistry, 1995, 60, 7508-7510 using a compound represented by formula (M-2).

Process 4

A compound represented by formula (1b) may be prepared by reacting the compound (M-3) with a compound represented by formula (R-3) (hereinafter, referred to as "compound (R-3)").

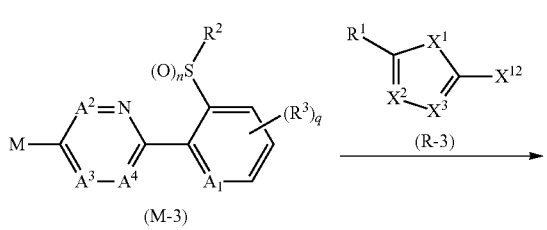

-continued

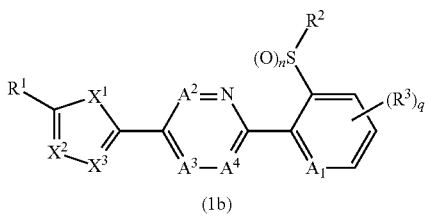

(1b)

wherein the symbols are the same as those defined above.

The reaction may be carried out according to a similar method to that described in Process 3 using the compound (R-3) instead of the compound (R-2).

Process 5

A compound represented by formula (1c) may be prepared by reacting the compound (M-3) with a compound represented by formula (R-4) (hereinafter, referred to as "compound (R-4)").

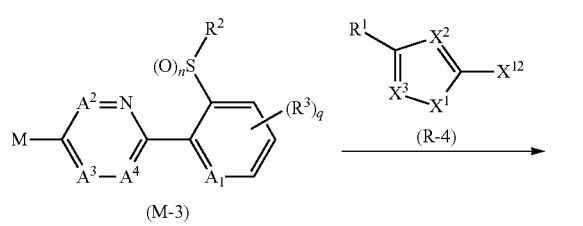

(1c)

wherein the symbols are the same as those defined above.

The reaction may be carried out according to a similar method to that described in Process 3 using the compound (R-4) instead of the compound (R-2).

Process 6

A compound represented by formula (1d) may be prepared by reacting the compound (M-3) with a compound represented by formula (R-5) (hereinafter, referred to as "compound (R-5)").

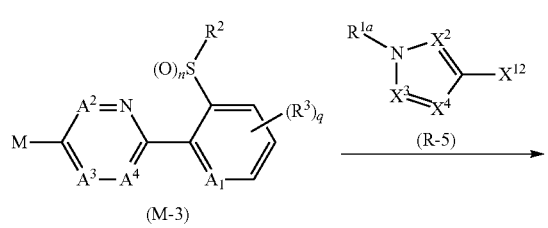

-continued

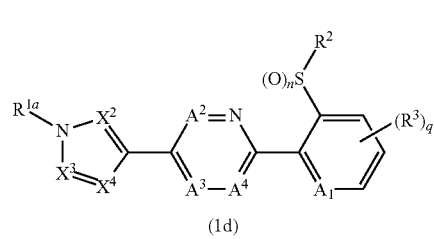

(1d)

wherein the symbols are the same as those defined above.

The reaction may be carried out according to a similar method to that described in Process 3 using the compound (R-5) instead of the compound (R-2).

Process 7

A compound represented by formula (1e) (hereinafter, referred to as "compound (1e)") may be prepared by reacting a compound represented by formula (M-4) (hereinafter, referred to as "compound (M-4)") with a compound represented by formula (R-6) (hereinafter, referred to as "compound (R-6)") in the presence of a base.

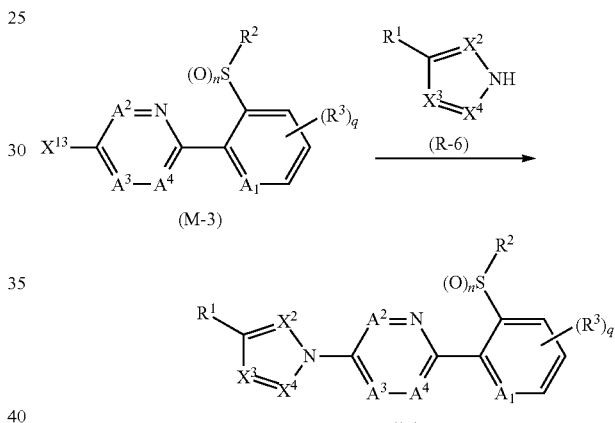

(1e)

wherein $X^{13}$ represents a chlorine atom or a fluorine atom, and the other symbols are the same as those defined above.

The reaction is usually carried out in a solvent.

Examples of the solvent to be used in the reaction include ethers, aromatic hydrocarbons, nitriles, polar aprotic solvents, and mixed solvents thereof.

Examples of the base to be used in the reaction include alkali metal carbonates and alkali metal hydrides.

In the reaction, the compound (R-6) is used usually within a range of 1 to 10 molar ratio(s), and the base is used usually within a range of 1 to 10 molar ratio(s), relative to 1 mole of the compound (M-4).

A reaction temperature in the reaction is usually within a range of −20 to 150° C. A reaction period in the reaction is usually within a range of 0.5 to 24 hours.

When the reaction is completed, to the reaction mixture is added water, and the reaction mixture is extracted with an organic solvent. The organic layer can be worked up (for example, drying and concentration) to give the compound (1e).

A process for preparing an intermediate compound is described as follows.

Reference Process 1

The compound (M-2) and the compound (M-4) may be prepared as a compound represented by formula (M-6)

(hereinafter, referred to as "compound (M-6)") or a compound represented by formula (M-7) (hereinafter, referred to as "compound (M-7)") according to the following scheme.

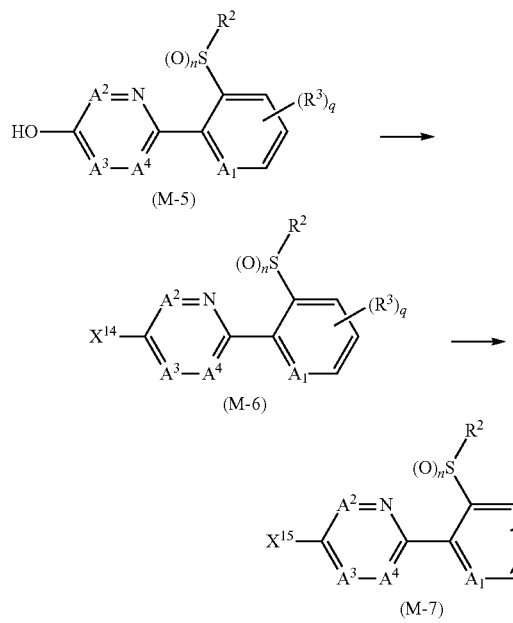

(M-5)

(M-6)

(M-7)

wherein $X^{14}$ represents a chlorine atom or a bromine atom, $X^{15}$ represents a fluorine atom or an iodine atom, and the other symbols are the same as those defined above.

Firstly, a process for preparing the compound (M-6) from the compound (M-5) is described.

The compound (M-6) may be prepared by reacting the compound (M-5) with phosphorus oxychloride or phosphorus oxybromide.

The reaction is usually carried out in a solvent.

Examples of the solvent to be used in the reaction include aromatic hydrocarbons.

When phosphorus oxychloride is used, phosphorus oxychloride can be used as the solvent.

In the reaction, phosphorus oxychloride or phosphorus oxybromide is used usually within a range of 1 to 10 molar ratio(s) relative to 1 mole of the compound (M-5).

A reaction temperature in the reaction is usually within a range of 0 to 150° C. A reaction period in the reaction is usually within a range of 0.5 to 24 hours.

When the reaction is completed, to the reaction mixture is added water, and the reaction mixture is extracted with an organic solvent. The organic layer can be worked up (for example, drying and concentration) to give the compound (M-6).

Next, a process for preparing the compound (M-7) from the compound (M-6) is described.

The compound (M-7) may be prepared by reacting the compound (M-6) with an inorganic fluoride or an inorganic iodide.

The reaction is usually carried out in a solvent.

Examples of the solvent to be used in the reaction include nitriles, polar aprotic solvents, nitrogen-containing aromatic compounds, and mixed solvents thereof.

Examples of the inorganic fluoride to be used in the reaction include potassium fluoride, sodium fluoride and cesium fluoride. Examples of the inorganic iodide to be used in the reaction include potassium iodide and sodium iodide.

In the reaction, the inorganic fluoride or inorganic iodide is used usually within a range of 1 to 10 molar ratio(s) relative to 1 mole of the compound (M-6).

A reaction temperature in the reaction is usually within a range of 0 to 250° C. A reaction period in the reaction is usually within a range of 0.5 to 24 hours.

When the reaction is completed, to the reaction mixture is added water, and the reaction mixture is extracted with an organic solvent. The organic layer can be worked up (for example, drying and concentration) to give the compound (M-7).

Reference Process 2

The compound (M-5) can be prepared by dealkylating a compound represented by formula (M-8) (hereinafter, referred to as "compound (M-8)") in the presence of an acid.

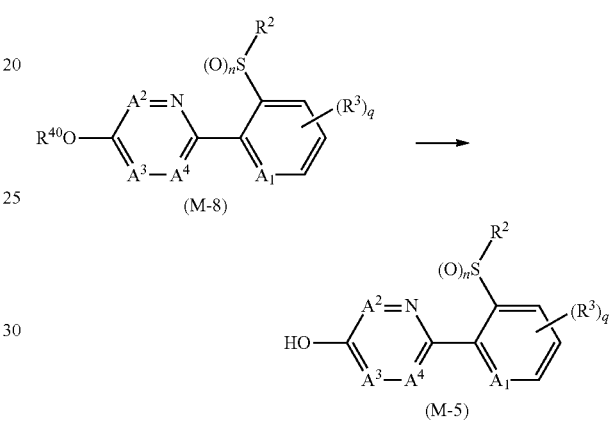

(M-8)

(M-5)

wherein $R^{40}$ represents a methyl group or an ethyl group, and the other symbols are the same as those defined above.

The reaction is usually carried out in a solvent.

Examples of the solvent to be used in the reaction include halogenated aliphatic hydrocarbons, aromatic hydrocarbons, nitriles, alcohols, acetic acid, water, and mixed solvents thereof.

Examples of the acid to be used in the reaction include mineral acids such as hydrochloric acid; boron halides such as boron trichloride and boron tribromide; titanium chloride; and aluminium chloride.

In the reaction, the acid is used usually within a range of 0.1 to 10 molar ratios relative to 1 mole of the compound (M-8).

When the mineral acid such as hydrochloric acid is used as an acid in the reaction, the mineral acid can be also used as a solvent.

A reaction temperature in the reaction is usually within a range of −20 to 150° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (M-5).

Reference Process 3

The compound (M-8) wherein n represents 0 (hereinafter, referred to as "compound (M-8a)"), the compound (M-8) wherein n represents 1 (hereinafter, referred to as "compound (M-8b)"), and the compound (M-8) wherein n represents 2 (hereinafter, referred to as "compound (M-8c)") may be prepared according to the following process.

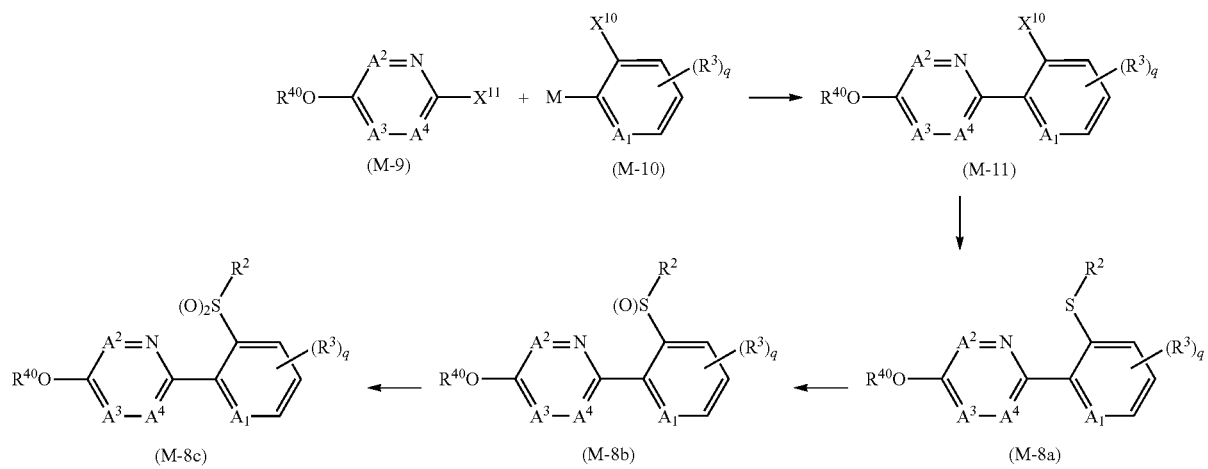

wherein the symbols are the same as those defined above.

Firstly, a process for preparing a compound represented by formula (M-11) (hereinafter, referred to as "compound (M-11)") is described.

The compound (M-11) may be prepared by reacting a compound represented by formula (M-9) (hereinafter, referred to as "compound (M-9)") with a compound represented by formula (M-10) (hereinafter, referred to as "compound (M-10)") in the presence of a metal catalyst.

The compound (M-10) may be prepared according to a similar method to that described in International Publication No. WO06/097691, or The Journal Of Organic Chemistry, 1995, 60, 7508-7510.

The reaction is usually carried out in a solvent.

Examples of the solvent to be used in the reaction include ethers, aromatic hydrocarbons, polar aprotic solvents, water, and mixed solvents thereof.

Examples of the metal catalyst to be used in the reaction include palladium catalysts such as tetrakis(triphenylphosphine)palladium(0), [1,1'-bis(diphenylphosphino)ferrocene]palladium(II) dichloride, tris(dibenzylideneacetone)dipalladium(0) and palladium(II) acetate; nickel catalysts such as bis(cyclooctadiene)nickel(0) and nickel(II) chloride; and copper catalysts such as copper(I) iodide and copper(I) chloride.

A ligand, a base, or an inorganic halide may be added in the reaction as needed.

Examples of the ligand to be used in the reaction include triphenylphosphine, xantphos, 2,2'-bis(diphenylphosphino)-1,1'-binaphthyl, 1,1'-bis(diphenylphosphino)ferrocene, 2-dicyclohexylphosphino-2',4',6'-triisopropylbiphenyl, 2-dicyclohexylphosphino-2',6'-dimethoxybiphenyl, 1,2-bis(diphenylphosphino)ethane, 2,2'-bipyridine, 2-aminoethanol, 8-hydroxyquinoline, and 1,10-phenanthroline.

Examples of the base to be used in the reaction include alkali metal hydrides, alkali metal carbonates, and organic bases.

Examples of the inorganic halides to be used in the reaction include alkali metal fluorides such as potassium fluoride and sodium fluoride; and alkali metal chlorides such as lithium chloride and sodium chloride.

In the reaction, the compound (M-10) is used usually within a range of 1 to 10 molar ratio(s), the metal catalyst is used usually within a range of 0.01 to 0.5 molar ratios, the ligand is used usually within a range of 0.01 to 1 molar ratio(s), and the base is used usually within a range of 0.1 to 5 molar ratios, relative to 1 mole of the compound (M-9).

A reaction temperature in the reaction is usually within a range of −20 to 200° C. A reaction period in the reaction is usually within a range of 0.1 to 24 hours.

When the reaction is completed, to the reaction mixture is added water, and the reaction mixture is extracted with an organic solvent. The organic layer can be worked up (for example, drying and concentration) to give the compound (M-11).

The compound (M-8a) may be prepared according to a similar method to that described in Process 2 using the compound (M-11) instead of the compound (M-1).

The compound (M-8b) and the compound (M-8c) may be prepared according to a similar method to that described in Process 1 using the compound (M-8a) instead of the compound (1-n0).

Reference Process 4

The compound (M-9) may be prepared by reacting a compound represented by formula (M-12) (hereinafter, referred to as "compound (M-12)") with a compound represented by formula (R-7) (hereinafter, referred to as "compound (R-7)") in the presence of a base.

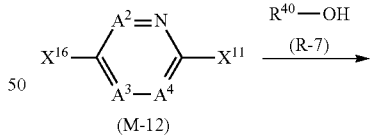

wherein $X^{16}$ represents a fluorine atom, a chlorine atom, or bromine atom, and the other symbols are the same as those defined above.

The reaction is usually carried out in a solvent.

Examples of the solvent to be used in the reaction include ethers, aromatic hydrocarbons, nitriles, polar aprotic solvents, and mixed solvents thereof.

Examples of the base to be used in the reaction include alkali metal carbonates and alkali metal hydrides.

In the reaction, the compound (R-7) is used usually within a range of 1 to 10 molar ratio(s), and the base is used usually within a range of 1 to 10 molar ratio(s), relative to 1 mole of the compound (M-12).

A reaction temperature in the reaction is usually within a range of −20 to 150° C. A reaction period in the reaction is usually within a range of 0.5 to 24 hours.

When the reaction is completed, the reaction mixture is extracted with an organic solvent, and the organic layer can be worked up (for example, drying and concentration) to give the compound (M-9).

The compound (M-12) and the compound (R-7) are commercially available, or can be prepared according to a known method.

Reference Process 5

The compound (M-1) can be prepared by reacting a compound represented by formula (M-13) (hereinafter, referred to as "compound (M-13)") with the compound (M-10) in the presence of a metal catalyst.

wherein the other symbols are the same as those defined above.

The compound (M-1) can be prepared according to the method for preparing the compound (M-11) as described in Reference Process 3 using the compound (M-13) instead of the compound (M-9).

The compound (M-13) may be prepared according to a known method.

Next, specific examples of the present compound are recited as follows.

In formula (I), specific examples of $Het^1$ are shown as follows.

-continued

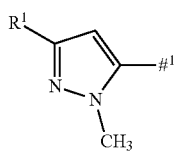 (H-17)

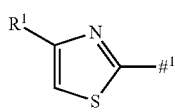 (H-18)

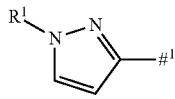 (H-19)

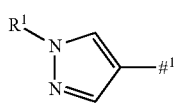 (H-20)

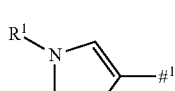 (H-21)

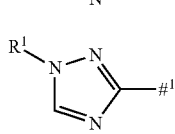 (H-22)

A compound represented by formula (L-1):

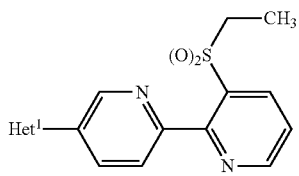 (L-1)

(hereinafter, referred to as "compound (L-1)"), wherein Het¹ represents H-1, and R¹ represents a substituent indicated in any of [Table 1] to [Table 3] (hereinafter, referred to as "compound group SX1").

TABLE 1

| R¹ |
| --- |
| $CF_3$ |
| $CF_2CF_3$ |
| $CF_2CF_2H$ |
| $CF_2CF_2CF_3$ |
| $CF_2CFHCF_3$ |

TABLE 2

| R¹ |
| --- |
| $CH_2CF_3$ |
| $CH_2CF_2CF_3$ |
| $CH_2CF_2CF_2H$ |
| $CH_2CF_2CF_2CF_3$ |
| $CH_2CF_2CFHCF_3$ |

TABLE 3

| R¹ |
| --- |
| $SCF_3$ |
| $S(O)CF_3$ |
| $S(O)_2CF_3$ |
| $SCF_2CF_3$ |
| $S(O)CF_2CF_3$ |
| $S(O)_2CF_2CF_3$ |

The compound (L-1), wherein Het¹ represents H-2, and R¹ represents a substituent indicated in any of [Table 1] to [Table 3] (hereinafter, referred to as "compound group SX2").

The compound (L-1), wherein Het¹ represents H-3, and R¹ represents a substituent indicated in any of [Table 1] to [Table 3] (hereinafter, referred to as "compound group SX3").

The compound (L-1), wherein Het¹ represents H-4, and R¹ represents a substituent indicated in any of [Table 1] to [Table 3] (hereinafter, referred to as "compound group SX4").

The compound (L-1), wherein Het¹ represents H-5, and R¹ represents a substituent indicated in any of [Table 1] to [Table 3] (hereinafter, referred to as "compound group SX5").

The compound (L-1), wherein Het¹ represents H-6, and R¹ represents a substituent indicated in [Table 1] (hereinafter, referred to as "compound group SX6").

The compound (L-1), wherein Het¹ represents H-7, and R¹ represents a substituent indicated in [Table 1] (hereinafter, referred to as "compound group SX7").

The compound (L-1), wherein Het¹ represents H-8, and R¹ represents a substituent indicated in [Table 1] (hereinafter, referred to as "compound group SX8").

The compound (L-1), wherein Het¹ represents H-9, and R¹ represents a substituent indicated in [Table 1] (hereinafter, referred to as "compound group SX9").

The compound (L-1), wherein Het¹ represents H-10, and R¹ represents a substituent indicated in [Table 1] (hereinafter, referred to as "compound group SX10").

The compound (L-1), wherein Het¹ represents H-11, and R¹ represents a substituent indicated in [Table 1] (hereinafter, referred to as "compound group SX11").

The compound (L-1), wherein Het¹ represents H-12, and R¹ represents a substituent indicated in [Table 1] (hereinafter, referred to as "compound group SX12").

The compound (L-1), wherein Het¹ represents H-13, and R¹ represents a substituent indicated in [Table 1] (hereinafter, referred to as "compound group SX13").

The compound (L-1), wherein Het¹ represents H-14, and R¹ represents a substituent indicated in [Table 1] (hereinafter, referred to as "compound group SX14").

The compound (L-1), wherein Het¹ represents H-15, and R¹ represents a substituent indicated in [Table 1] (hereinafter, referred to as "compound group SX15").

The compound (L-1), wherein Het¹ represents H-16, and R¹ represents a substituent indicated in [Table 1] (hereinafter, referred to as "compound group SX16").

The compound (L-1), wherein Het¹ represents H-17, and R¹ represents a substituent indicated in [Table 1] (hereinafter, referred to as "compound group SX17").

The compound (L-1), wherein Het¹ represents H-18, and R¹ represents a substituent indicated in [Table 1] (hereinafter, referred to as "compound group SX18").

The compound (L-1), wherein Het¹ represents H-19, and R¹ represents a substituent indicated in [Table 2] (hereinafter, referred to as "compound group SX19").

The compound (L-1), wherein Het$^1$ represents H-20, and R$^1$ represents a substituent indicated in [Table 2] (hereinafter, referred to as "compound group SX20").

The compound (L-1), wherein Het$^1$ represents H-21, and R$^1$ represents a substituent indicated in [Table 2] (hereinafter, referred to as "compound group SX21").

The compound (L-1), wherein Het$^1$ represents H-22, and R$^1$ represents a substituent indicated in [Table 2] (hereinafter, referred to as "compound group SX22").

A compound represented by formula (L-2):

(L-2)

(hereinafter, referred to as "compound (L-2)"),
wherein Het$^1$ represents H-1, and R$^1$ represents a substituent indicated in any of [Table 1] to [Table 3] (hereinafter, referred to as "compound group SX23").

The compound (L-2), wherein Het$^1$ represents H-2, and R$^1$ represents a substituent indicated in any of [Table 1] to [Table 3] (hereinafter, referred to as "compound group SX24").

The compound (L-2), wherein Het$^1$ represents H-3, and R$^1$ represents a substituent indicated in any of [Table 1] to [Table 3] (hereinafter, referred to as "compound group SX25").

The compound (L-2), wherein Het$^1$ represents H-4, and R$^1$ represents a substituent indicated in any of [Table 1] to [Table 3] (hereinafter, referred to as "compound group SX26").

The compound (L-2), wherein Het$^1$ represents H-5, and R$^1$ represents a substituent indicated in any of [Table 1] to [Table 3] (hereinafter, referred to as "compound group SX27").

The compound (L-2), wherein Het$^1$ represents H-6, and R$^1$ represents a substituent indicated in any of [Table 1] (hereinafter, referred to as "compound group SX28").

The compound (L-2), wherein Het$^1$ represents H-7, and R$^1$ represents a substituent indicated in any of [Table 1] (hereinafter, referred to as "compound group SX29").

The compound (L-2), wherein Het$^1$ represents H-8, and R$^1$ represents a substituent indicated in any of [Table 1] (hereinafter, referred to as "compound group SX30").

The compound (L-2), wherein Het$^1$ represents H-9, and R$^1$ represents a substituent indicated in any of [Table 1] (hereinafter, referred to as "compound group SX31").

The compound (L-2), wherein Het$^1$ represents H-10, and R$^1$ represents a substituent indicated in any of [Table 1] (hereinafter, referred to as "compound group SX32").

The compound (L-2), wherein Het$^1$ represents H-11, and R$^1$ represents a substituent indicated in any of [Table 1] (hereinafter, referred to as "compound group SX33").

The compound (L-2), wherein Het$^1$ represents H-12, and R$^1$ represents a substituent indicated in any of [Table 1] (hereinafter, referred to as "compound group SX34").

The compound (L-2), wherein Het$^1$ represents H-13, and R$^1$ represents a substituent indicated in any of [Table 1] (hereinafter, referred to as "compound group SX35").

The compound (L-2), wherein Het$^1$ represents H-14, and R$^1$ represents a substituent indicated in any of [Table 1] (hereinafter, referred to as "compound group SX36").

The compound (L-2), wherein Het$^1$ represents H-15, and R$^1$ represents a substituent indicated in any of [Table 1] (hereinafter, referred to as "compound group SX37").

The compound (L-2), wherein Het$^1$ represents H-16, and R$^1$ represents a substituent indicated in any of [Table 1] (hereinafter, referred to as "compound group SX38").

The compound (L-2), wherein Het$^1$ represents H-17, and R$^1$ represents a substituent indicated in any of [Table 1] (hereinafter, referred to as "compound group SX39").

The compound (L-2), wherein Het$^1$ represents H-18, and R$^1$ represents a substituent indicated in any of [Table 1] (hereinafter, referred to as "compound group SX40").

The compound (L-2), wherein Het$^1$ represents H-19, and R$^1$ represents a substituent indicated in any of [Table 2] (hereinafter, referred to as "compound group SX41").

The compound (L-2), wherein Het$^1$ represents H-20, and R$^1$ represents a substituent indicated in any of [Table 2] (hereinafter, referred to as "compound group SX42").

The compound (L-2), wherein Het$^1$ represents H-21, and R$^1$ represents a substituent indicated in any of [Table 2] (hereinafter, referred to as "compound group SX43").

The compound (L-2), wherein Het$^1$ represents H-22, and R$^1$ represents a substituent indicated in any of [Table 2] (hereinafter, referred to as "compound group SX44").

A compound represented by formula (L-3):

(L-3)

(hereinafter, referred to as "compound (L-3)"),
wherein Het$^1$ represents H-1, and R$^1$ represents a substituent indicated in any of [Table 1] to [Table 3] (hereinafter, referred to as "compound group SX45").

The compound (L-3), wherein Het$^1$ represents H-2, and R$^1$ represents a substituent indicated in any of [Table 1] to [Table 3] (hereinafter, referred to as "compound group SX46").

The compound (L-3), wherein Het$^1$ represents H-3, and R$^1$ represents a substituent indicated in any of [Table 1] to [Table 3] (hereinafter, referred to as "compound group SX47").

The compound (L-3), wherein Het$^1$ represents H-4, and R$^1$ represents a substituent indicated in any of [Table 1] to [Table 3] (hereinafter, referred to as "compound group SX48").

The compound (L-3), wherein Het$^1$ represents H-5, and R$^1$ represents a substituent indicated in any of [Table 1] to [Table 3] (hereinafter, referred to as "compound group SX49").

The compound (L-3), wherein Het$^1$ represents H-6, and R$^1$ represents a substituent indicated in any of [Table 1] (hereinafter, referred to as "compound group SX50").

The compound (L-3), wherein Het$^1$ represents H-7, and R$^1$ represents a substituent indicated in any of [Table 1] (hereinafter, referred to as "compound group SX51").

The compound (L-3), wherein Het$^1$ represents H-8; and R$^1$ represents a substituent indicated in any of [Table 1] (hereinafter, referred to as "compound group SX52").

The compound (L-3), wherein Het¹ represents H-9, and R¹ represents a substituent indicated in any of [Table 1] (hereinafter, referred to as "compound group SX53").

The compound (L-3), wherein Het¹ represents H-10, and R¹ represents a substituent indicated in any of [Table 1] (hereinafter, referred to as "compound group SX54").

The compound (L-3), wherein Het¹ represents H-11, and R¹ represents a substituent indicated in any of [Table 1] (hereinafter, referred to as "compound group SX55").

The compound (L-3), wherein Het¹ represents H-12, and R¹ represents a substituent indicated in any of [Table 1] (hereinafter, referred to as "compound group SX56").

The compound (L-3), wherein Het¹ represents H-13, and R¹ represents a substituent indicated in any of [Table 1] (hereinafter, referred to as "compound group SX57").

The compound (L-3), wherein Het¹ represents H-14, and R¹ represents a substituent indicated in any of [Table 1] (hereinafter, referred to as "compound group SX58").

The compound (L-3), wherein Het¹ represents H-15, and R¹ represents a substituent indicated in any of [Table 1] (hereinafter, referred to as "compound group SX59").

The compound (L-3), wherein Het¹ represents H-16, and R¹ represents a substituent indicated in any of [Table 1] (hereinafter, referred to as "compound group SX60").

The compound (L-3), wherein Het¹ represents H-17, and R¹ represents a substituent indicated in any of [Table 1] (hereinafter, referred to as "compound group SX61").

The compound (L-3), wherein Het¹ represents H-18, and R¹ represents a substituent indicated in any of [Table 1] (hereinafter, referred to as "compound group SX62").

The compound (L-3), wherein Het¹ represents H-19, and R¹ represents a substituent indicated in any of [Table 2] (hereinafter, referred to as "compound group SX63").

The compound (L-3), wherein Het¹ represents H-20, and R¹ represents a substituent indicated in any of [Table 2] (hereinafter, referred to as "compound group SX64").

The compound (L-3), wherein Het¹ represents H-21, and R¹ represents a substituent indicated in any of [Table 2] (hereinafter, referred to as "compound group SX65").

The compound (L-3), wherein Het¹ represents H-22, and R¹ represents a substituent indicated in any of [Table 2] (hereinafter, referred to as "compound group SX66").

A compound represented by formula (L-4):

(L-4)

(hereinafter, referred to as "compound (L-4)"),
wherein Het¹ represents H-1, and R¹ represents a substituent indicated in any of [Table 1] to [Table 3] (hereinafter, referred to as "compound group SX67").

The compound (L-4), wherein Het¹ represents H-2, and R¹ represents a substituent indicated in any of [Table 1] to [Table 3] (hereinafter, referred to as "compound group SX68").

The compound (L-4), wherein Het¹ represents H-3, and R¹ represents a substituent indicated in any of [Table 1] to [Table 3] (hereinafter, referred to as "compound group SX69").

The compound (L-4), wherein Het¹ represents H-4, and R¹ represents a substituent indicated in any of [Table 1] to [Table 3] (hereinafter, referred to as "compound group SX70").

The compound (L-4), wherein Het¹ represents H-5, and R¹ represents a substituent indicated in any of [Table 1] to [Table 3] (hereinafter, referred to as "compound group SX71").

The compound (L-4), wherein Het¹ represents H-6, and R¹ represents a substituent indicated in any of [Table 1] (hereinafter, referred to as "compound group SX72").

The compound (L-4), wherein Het¹ represents H-7, and R¹ represents a substituent indicated in any of [Table 1] (hereinafter, referred to as "compound group SX73").

The compound (L-4), wherein Het¹ represents H-8, and R¹ represents a substituent indicated in any of [Table 1] (hereinafter, referred to as "compound group SX74").

The compound (L-4), wherein Het¹ represents H-9, and R¹ represents a substituent indicated in any of [Table 1] (hereinafter, referred to as "compound group SX75").

The compound (L-4), wherein Het¹ represents H-10, and R¹ represents a substituent indicated in any of [Table 1] (hereinafter, referred to as "compound group SX76").

The compound (L-4), wherein Het¹ represents H-11, and R¹ represents a substituent indicated in any of [Table 1] (hereinafter, referred to as "compound group SX77").

The compound (L-4), wherein Het¹ represents H-12, and R¹ represents a substituent indicated in any of [Table 1] (hereinafter, referred to as "compound group SX78").

The compound (L-4), wherein Het¹ represents H-13, and R¹ represents a substituent indicated in any of [Table 1] (hereinafter, referred to as "compound group SX79").

The compound (L-4), wherein Het¹ represents H-14, and R¹ represents a substituent indicated in any of [Table 1] (hereinafter, referred to as "compound group SX80").

The compound (L-4), wherein Het¹ represents H-15, and R¹ represents a substituent indicated in any of [Table 1] (hereinafter, referred to as "compound group SX81").

The compound (L-4), wherein Het¹ represents H-16, and R¹ represents a substituent indicated in any of [Table 1] (hereinafter, referred to as "compound group SX82").

The compound (L-4), wherein Het¹ represents H-17, and R¹ represents a substituent indicated in any of [Table 1] (hereinafter, referred to as "compound group SX83").

The compound (L-4), wherein Het¹ represents H-18, and R¹ represents a substituent indicated in any of [Table 1] (hereinafter, referred to as "compound group SX84").

The compound (L-4), wherein Het¹ represents H-19, and R¹ represents a substituent indicated in any of [Table 2] (hereinafter, referred to as "compound group SX85").

The compound (L-4), wherein Het¹ represents H-20, and R¹ represents a substituent indicated in any of [Table 2] (hereinafter, referred to as "compound group SX86").

The compound (L-4), wherein Het¹ represents H-21, and R¹ represents a substituent indicated in any of [Table 2] (hereinafter, referred to as "compound group SX87").

The compound (L-4), wherein Het¹ represents H-22, and R¹ represents a substituent indicated in any of [Table 2] (hereinafter, referred to as "compound group SX88").

A compound represented by formula (L-5):

$$\text{Het}^1-\underset{\substack{\|\\N-N}}{\bigcirc}-\underset{\substack{\|\\N}}{\bigcirc}(O)_2S-CH_3 \quad CF_3 \quad (L\text{-}5)$$

(hereinafter, referred to as "compound (L-5)"),
wherein Het¹ represents H-1, and R¹ represents a substituent indicated in any of [Table 1] to [Table 3] (hereinafter, referred to as "compound group SX89").

The compound (L-5), wherein Het¹ represents H-2, and R¹ represents a substituent indicated in any of [Table 1] to [Table 3] (hereinafter, referred to as "compound group SX90").

The compound (L-5), wherein Het¹ represents H-3, and R¹ represents a substituent indicated in any of [Table 1] to [Table 3] (hereinafter, referred to as "compound group SX91").

The compound (L-5), wherein Het¹ represents H-4, and R¹ represents a substituent indicated in any of [Table 1] to [Table 3] (hereinafter, referred to as "compound group SX92").

The compound (L-5), wherein Het¹ represents H-5, and R¹ represents a substituent indicated in any of [Table 1] to [Table 3] (hereinafter, referred to as "compound group SX93").

The compound (L-5), wherein Het¹ represents H-6, and R¹ represents a substituent indicated in any of [Table 1] (hereinafter, referred to as "compound group SX94").

The compound (L-5), wherein Het¹ represents H-7, and R¹ represents a substituent indicated in any of [Table 1] (hereinafter, referred to as "compound group SX95").

The compound (L-5), wherein Het¹ represents H-8, and R¹ represents a substituent indicated in any of [Table 1] (hereinafter, referred to as "compound group SX96").

The compound (L-5), wherein Het¹ represents H-9, and R¹ represents a substituent indicated in any of [Table 1] (hereinafter, referred to as "compound group SX97").

The compound (L-5), wherein Het¹ represents H-10, and R¹ represents a substituent indicated in any of [Table 1] (hereinafter, referred to as "compound group SX98").

The compound (L-5), wherein Het¹ represents H-11, and R¹ represents a substituent indicated in any of [Table 1] (hereinafter, referred to as "compound group SX99").

The compound (L-5), wherein Het¹ represents H-12, and R¹ represents a substituent indicated in any of [Table 1] (hereinafter, referred to as "compound group SX100").

The compound (L-5), wherein Het¹ represents H-13, and R¹ represents a substituent indicated in any of [Table 1] (hereinafter, referred to as "compound group SX101").

The compound (L-5), wherein Het¹ represents H-14, and R¹ represents a substituent indicated in any of [Table 1] (hereinafter, referred to as "compound group SX102").

The compound (L-5), wherein Het¹ represents H-15, and R¹ represents a substituent indicated in any of [Table 1] (hereinafter, referred to as "compound group SX103").

The compound (L-5), wherein Het¹ represents H-16, and R¹ represents a substituent indicated in any of [Table 1] (hereinafter, referred to as "compound group SX104").

The compound (L-5), wherein Het¹ represents H-17, and R¹ represents a substituent indicated in any of [Table 1] (hereinafter, referred to as "compound group SX105").

The compound (L-5), wherein Het¹ represents H-18, and R¹ represents a substituent indicated in any of [Table 1] (hereinafter, referred to as "compound group SX106").

The compound (L-5), wherein Het¹ represents H-19, and R¹ represents a substituent indicated in any of [Table 2] (hereinafter, referred to as "compound group SX107").

The compound (L-5), wherein Het¹ represents H-20, and R¹ represents a substituent indicated in any of [Table 2] (hereinafter, referred to as "compound group SX108").

The compound (L-5), wherein Het¹ represents H-21, and R¹ represents a substituent indicated in any of [Table 2] (hereinafter, referred to as "compound group SX109").

The compound (L-5), wherein Het¹ represents H-22, and R¹ represents a substituent indicated in any of [Table 2] (hereinafter, referred to as "compound group SX110").

A compound represented by formula (L-6):

$$\text{Het}^1-\underset{\substack{\|\\N-N}}{\bigcirc}-\bigcirc(O)_2S-CH_3 \quad CF_3 \quad (L\text{-}6)$$

(hereinafter, referred to as "compound (L-6)"),
wherein Het¹ represents H-1, and R¹ represents a substituent indicated in any of [Table 1] to [Table 3] (hereinafter, referred to as "compound group SX111").

The compound (L-6), wherein Het¹ represents H-2, and R¹ represents a substituent indicated in any of [Table 1] to [Table 3] (hereinafter, referred to as "compound group SX112").

The compound (L-6), wherein Het¹ represents H-3, and R¹ represents a substituent indicated in any of [Table 1] to [Table 3] (hereinafter, referred to as "compound group SX113").

The compound (L-6), wherein Het¹ represents H-4, and R¹ represents a substituent indicated in any of [Table 1] to [Table 3] (hereinafter, referred to as "compound group SX114").

The compound (L-6), wherein Het¹ represents H-5, and R¹ represents a substituent indicated in any of [Table 1] to [Table 3] (hereinafter, referred to as "compound group SX115").

The compound (L-6), wherein Het¹ represents H-6, and R¹ represents a substituent indicated in any of [Table 1] (hereinafter, referred to as "compound group SX116").

The compound (L-6), wherein Het¹ represents H-7, and R¹ represents a substituent indicated in, any of [Table 1] (hereinafter, referred to as "compound group SX117").

The compound (L-6), wherein Het¹ represents H-8, and R¹ represents a substituent indicated in any of [Table 1] (hereinafter, referred to as "compound group SX118").

The compound (L-6), wherein Het¹ represents H-9, and R¹ represents a substituent indicated in any of [Table 1] (hereinafter, referred to as "compound group SX119").

The compound (L-6), wherein Het¹ represents H-10, and R¹ represents a substituent indicated in any of [Table 1] (hereinafter, referred to as "compound group SX120").

The compound (L-6), wherein Het¹ represents H-11, and R¹ represents a substituent indicated in any of [Table 1] (hereinafter, referred to as "compound group SX121").

The compound (L-6), wherein Het¹ represents H-12, and R¹ represents a substituent indicated in any of [Table 1] (hereinafter, referred to as "compound group SX122").

The compound (L-6), wherein Het¹ represents H-13, and R¹ represents a substituent indicated in any of [Table 1] (hereinafter, referred to as "compound group SX123").

The compound (L-6), wherein Het¹ represents H-14, and R¹ represents a substituent indicated in any of [Table 1] (hereinafter, referred to as "compound group SX124").

The compound (L-6), wherein Het¹ represents H-15, and R¹ represents a substituent indicated in any of [Table 1] (hereinafter, referred to as "compound group SX125").

The compound (L-6), wherein Het¹ represents H-16, and R¹ represents a substituent indicated in any of [Table 1] (hereinafter, referred to as "compound group SX126").

The compound (L-6), wherein Het¹ represents H-17, and R¹ represents a substituent indicated in any of [Table 1] (hereinafter, referred to as "compound group SX127").

The compound (L-6), wherein Het¹ represents H-18, and R¹ represents a substituent indicated in any of [Table 1] (hereinafter, referred to as "compound group SX128").

The compound (L-6), wherein Het¹ represents H-19, and R¹ represents a substituent indicated in any of [Table 2] (hereinafter, referred to as "compound group SX129").

The compound (L-6), wherein Het¹ represents H-20, and R¹ represents a substituent indicated in any of [Table 2] (hereinafter, referred to as "compound group SX130").

The compound (L-6), wherein Het¹ represents H-21, and R¹ represents a substituent indicated in any of [Table 2] (hereinafter, referred to as "compound group SX131").

The compound (L-6), wherein Het¹ represents H-22, and R¹ represents a substituent indicated in any of [Table 2] (hereinafter, referred to as "compound group SX132").

A compound represented by formula (L-7):

(L-7)

(hereinafter, referred to as "compound (L-7)"),
wherein Het¹ represents H-1, and R¹ represents a substituent indicated in any of [Table 1] to [Table 3] (hereinafter, referred to as "compound group SX133").

The compound (L-7), wherein Het¹ represents H-2, and R¹ represents a substituent indicated in any of [Table 1] to [Table 3] (hereinafter, referred to as "compound group SX134").

The compound (L-7), wherein Het¹ represents H-3, and R¹ represents a substituent indicated in any of [Table 1] to [Table 3] (hereinafter, referred to as "compound group SX135").

The compound (L-7), wherein Het¹ represents H-4, and R¹ represents a substituent indicated in any of [Table 1] to [Table 3] (hereinafter, referred to as "compound group SX136").

The compound (L-7), wherein Het¹ represents H-5, and R¹ represents a substituent indicated in any of [Table 1] to [Table 3] (hereinafter, referred to as "compound group SX137").

The compound (L-7), wherein Het¹ represents H-6, and R¹ represents a substituent indicated in any of [Table 1] (hereinafter, referred to as "compound group SX138").

The compound (L-7), wherein Het¹ represents H-7, and R¹ represents a substituent indicated in any of [Table 1] (hereinafter, referred to as "compound group SX139").

The compound (L-7), wherein Het¹ represents H-8, and R¹ represents a substituent indicated in any of [Table 1] (hereinafter, referred to as "compound group SX140").

The compound (L-7), wherein Het¹ represents H-9, and R¹ represents a substituent indicated in any of [Table 1] (hereinafter, referred to as "compound group SX141").

The compound (L-7), wherein Het¹ represents H-10, and R¹ represents a substituent indicated in any of [Table 1] (hereinafter, referred to as "compound group SX142").

The compound (L-7), wherein Het¹ represents H-11, and R¹ represents a substituent indicated in any of [Table 1] (hereinafter, referred to as "compound group SX143").

The compound (L-7), wherein Het¹ represents H-12, and R¹ represents a substituent indicated in any of [Table 1] (hereinafter, referred to as "compound group SX144").

The compound (L-7), wherein Het¹ represents H-13, and R¹ represents a substituent indicated in any of [Table 1] (hereinafter, referred to as "compound group SX145").

The compound (L-7), wherein Het¹ represents H-14, and R¹ represents a substituent indicated in any of [Table 1] (hereinafter, referred to as "compound group SX146").

The compound (L-7), wherein Het¹ represents H-15, and R¹ represents a substituent indicated in any of [Table 1] (hereinafter, referred to as "compound group SX147").

The compound (L-7), wherein Het¹ represents H-16, and R¹ represents a substituent indicated in any of [Table 1] (hereinafter, referred to as "compound group SX148").

The compound (L-7), wherein Het¹ represents H-17, and R¹ represents a substituent indicated in any of [Table 1] (hereinafter, referred to as "compound group SX149").

The compound (L-7), wherein Het¹ represents H-18, and R¹ represents a substituent indicated in any of [Table 1] (hereinafter, referred to as "compound group SX150").

The compound (L-7), wherein Het¹ represents H-19, and R¹ represents a substituent indicated in any of [Table 2] (hereinafter, referred to as "compound group SX151").

The compound (L-7), wherein Het¹ represents H-20, and R¹ represents a substituent indicated in any of [Table 2] (hereinafter, referred to as "compound group SX152").

The compound (L-7), wherein Het¹ represents H-21, and R¹ represents a substituent indicated in any of [Table 2] (hereinafter, referred to as "compound group SX153").

The compound (L-7), wherein Het¹ represents H-22, and R¹ represents a substituent indicated in any of [Table 2] (hereinafter, referred to as "compound group SX154").

A compound represented by formula (L-8):

(L-8)

(hereinafter, referred to as "compound (L-8)"),
wherein Het¹ represents H-1, and R¹ represents a substituent indicated in any of [Table 1] to [Table 3] (hereinafter, referred to as "compound group SX155").

The compound (L-8), wherein Het¹ represents H-2, and R¹ represents a substituent indicated in any of [Table 1] to [Table 3] (hereinafter, referred to as "compound group SX156").

The compound (L-8), wherein Het¹ represents H-3, and R¹ represents a substituent indicated in any of [Table 1] to [Table 3] (hereinafter, referred to as "compound group SX157").

The compound (L-8), wherein Het¹ represents H-4, and R¹ represents a substituent indicated in any of [Table 1] to [Table 3] (hereinafter, referred to as "compound group SX158").

The compound (L-8), wherein Het¹ represents H-5, and R¹ represents a substituent indicated in any of [Table 1] to [Table 3] (hereinafter, referred to as "compound group SX159").

The compound (L-8), wherein Het¹ represents H-6, and R¹ represents a substituent indicated in any of [Table 1] (hereinafter, referred to as "compound group SX160").

The compound (L-8), wherein Het¹ represents H-7, and R¹ represents a substituent indicated in any of [Table 1] (hereinafter, referred to as "compound group SX161").

The compound (L-8), wherein Het¹ represents H-8, and R¹ represents a substituent indicated in any of [Table 1] (hereinafter, referred to as "compound group SX162").

The compound (L-8), wherein Het¹ represents H-9, and R¹ represents a substituent indicated in any of [Table 1] (hereinafter, referred to as "compound group SX163").

The compound (L-8), wherein Het¹ represents H-10, and R¹ represents a substituent indicated in any of [Table 1] (hereinafter, referred to as "compound group SX164").

The compound (L-8), wherein Het¹ represents H-11, and R¹ represents a substituent indicated in any of [Table 1] (hereinafter, referred to as "compound group SX165").

The compound (L-8), wherein Het¹ represents H-12, and R¹ represents a substituent indicated in any of [Table 1] (hereinafter, referred to as "compound group SX166").

The compound (L-8), wherein Het¹ represents H-13, and R¹ represents a substituent indicated in any of [Table 1] (hereinafter, referred to as "compound group SX167").

The compound (L-8), wherein Het¹ represents H-14, and R¹ represents a substituent indicated in any of [Table 1] (hereinafter, referred to as "compound group SX168").

The compound (L-8), wherein Het¹ represents H-15, and R¹ represents a substituent indicated in any of [Table 1] (hereinafter, referred to as "compound group SX169").

The compound (L-8), wherein Het¹ represents H-16, and R¹ represents a substituent indicated in any of [Table 1] (hereinafter, referred to as "compound group SX170").

The compound (L-8), wherein Het¹ represents H-17, and R¹ represents a substituent indicated in any of [Table 1] (hereinafter, referred to as "compound group SX171").

The compound (L-8), wherein Het¹ represents H-18, and R¹ represents a substituent indicated in any of [Table 1] (hereinafter, referred to as "compound group SX172").

The compound (L-8), wherein Het¹ represents H-19, and R¹ represents a substituent indicated in any of [Table 2] (hereinafter, referred to as "compound group SX173").

The compound (L-8), wherein Het¹ represents H-20, and R¹ represents a substituent indicated in any of [Table 2] (hereinafter, referred to as "compound group SX174").

The compound (L-8), wherein Het¹ represents H-21, and R¹ represents a substituent indicated in any of [Table 2] (hereinafter, referred to as "compound group SX175").

The compound (L-8), wherein Het¹ represents H-22, and R¹ represents a substituent indicated in any of [Table 2] (hereinafter, referred to as "compound group SX176").

A compound represented by formula (L-9):

(L-9)

(hereinafter, referred to as "compound (L-9)"),
wherein Het¹ represents H-1, and R¹ represents a substituent indicated in any of [Table 1] to [Table 3] (hereinafter, referred to as "compound group SX177").

The compound (L-9), wherein Het¹ represents H-2, and R¹ represents a substituent indicated in any of [Table 1] to [Table 3] (hereinafter, referred to as "compound group SX178").

The compound (L-9), wherein Het¹ represents H-3, and R¹ represents a substituent indicated in any of [Table 1] to [Table 3] (hereinafter, referred to as "compound group SX179").

The compound (L-9), wherein Het¹ represents H-4, and R¹ represents a substituent indicated in any of [Table 1] to [Table 3] (hereinafter, referred to as "compound group SX180").

The compound (L-9), wherein Het¹ represents H-5, and R¹ represents a substituent indicated in any of [Table 1] to [Table 3] (hereinafter, referred to as "compound group SX181").

The compound (L-9), wherein Het¹ represents H-6, and R¹ represents a substituent indicated in any of [Table 1] (hereinafter, referred to as "compound group SX182").

The compound (L-9), wherein Het¹ represents H-7, and R¹ represents a substituent indicated in any of [Table 1] (hereinafter, referred to as "compound group SX183").

The compound (L-9), wherein Het¹ represents H-8, and R¹ represents a substituent indicated in any of [Table 1] (hereinafter, referred to as "compound group SX184").

The compound (L-9), wherein Het¹ represents H-9, and R¹ represents a substituent indicated in any of [Table 1] (hereinafter, referred to as "compound group SX185").

The compound (L-9), wherein Het¹ represents H-10, and R¹ represents a substituent indicated in any of [Table 1] (hereinafter, referred to as "compound group SX186").

The compound (L-9), wherein Het¹ represents H-11, and R¹ represents a substituent indicated in any of [Table 1] (hereinafter, referred to as "compound group SX187").

The compound (L-9), wherein Het¹ represents H-12, and R¹ represents a substituent indicated in any of [Table 1] (hereinafter, referred to as "compound group SX188").

The compound (L-9), wherein Het¹ represents H-13, and R¹ represents a substituent indicated in any of [Table 1] (hereinafter, referred to as "compound group SX189").

The compound (L-9), wherein Het¹ represents H-14, and R¹ represents a substituent indicated in any of [Table 1] (hereinafter, referred to as "compound group SX190").

The compound (L-9), wherein Het¹ represents H-15, and R¹ represents a substituent indicated in any of [Table 1] (hereinafter, referred to as "compound group SX191").

The compound (L-9), wherein Het¹ represents H-16, and R¹ represents a substituent indicated in any of [Table 1] (hereinafter, referred to as "compound group SX192").

The compound (L-9), wherein Het$^1$ represents H-17, and R$^1$ represents a substituent indicated in any of [Table 1] (hereinafter, referred to as "compound group SX193").

The compound (L-9), wherein Het$^1$ represents H-18, and R$^1$ represents a substituent indicated in any of [Table 1] (hereinafter, referred to as "compound group SX194").

The compound (L-9), wherein Het$^1$ represents H-19, and R$^1$ represents a substituent indicated in any of [Table 2] (hereinafter, referred to as "compound group SX195").

The compound (L-9), wherein Het$^1$ represents H-20, and R$^1$ represents a substituent indicated in any of [Table 2] (hereinafter, referred to as "compound group SX196").

The compound (L-9), wherein Het$^1$ represents H-21, and R$^1$ represents a substituent indicated in any of [Table 2] (hereinafter, referred to as "compound group SX197").

The compound (L-9), wherein Het$^1$ represents H-22, and R$^1$ represents a substituent indicated in any of [Table 2] (hereinafter, referred to as "compound group SX198").

A compound represented by formula (L-10):

(L-10)

(hereinafter, referred to as "compound (L-10)"),
wherein Het$^1$ represents H-1, and R$^1$ represents a substituent indicated in any of [Table 1] to [Table 3] (hereinafter, referred to as "compound group SX199").

The compound (L-10), wherein Het$^1$ represents H-2, and R$^1$ represents a substituent indicated in any of [Table 1] to [Table 3] (hereinafter, referred to as "compound group SX200").

The compound (L-10), wherein Het$^1$ represents H-3, and R$^1$ represents a substituent indicated in any of [Table 1] to [Table 3] (hereinafter, referred to as "compound group SX201").

The compound (L-10), wherein Het$^1$ represents H-4, and R$^1$ represents a substituent indicated in any of [Table 1] to [Table 3] (hereinafter, referred to as "compound group SX202").

The compound (L-10), wherein Het$^1$ represents H-5, and R$^1$ represents a substituent indicated in any of [Table 1] to [Table 3] (hereinafter, referred to as "compound group SX203").

The compound (L-10), wherein Het$^1$ represents H-6, and R$^1$ represents a substituent indicated in any of [Table 1] (hereinafter, referred to as "compound group SX204").

The compound (L-10), wherein Het$^1$ represents H-7, and R$^1$ represents a substituent indicated in any of [Table 1] (hereinafter, referred to as "compound group SX205").

The compound (L-10), wherein Het$^1$ represents H-8, and R$^1$ represents a substituent indicated in any of [Table 1] (hereinafter, referred to as "compound group SX206").

The compound (L-10), wherein Het$^1$ represents H-9, and R$^1$ represents a substituent indicated in any of [Table 1] (hereinafter, referred to as "compound group SX207").

The compound (L-10), wherein Het$^1$ represents H-10, and R$^1$ represents a substituent indicated in any of [Table 1] (hereinafter, referred to as "compound group SX208").

The compound (L-10), wherein Het$^1$ represents H-11, and R$^1$ represents a substituent indicated in any of [Table 1] (hereinafter, referred to as "compound group SX209").

The compound (L-10), wherein Het$^1$ represents H-12, and R$^1$ represents a substituent indicated in any of [Table 1] (hereinafter, referred to as "compound group SX210").

The compound (L-10), wherein Het$^1$ represents H-13, and R$^1$ represents a substituent indicated in any of [Table 1] (hereinafter, referred to as "compound group SX211").

The compound (L-10), wherein Het$^1$ represents H-14, and R$^1$ represents a substituent indicated in any of [Table 1] (hereinafter, referred to as "compound group SX212").

The compound (L-10), wherein Het$^1$ represents H-15, and R$^1$ represents a substituent indicated in any of [Table 1] (hereinafter, referred to as "compound group SX213").

The compound (L-10), wherein Het$^1$ represents H-16, and R$^1$ represents a substituent indicated in any of [Table 1] (hereinafter, referred to as "compound group SX214").

The compound (L-10), wherein Het$^1$ represents H-17, and R$^1$ represents a substituent indicated in any of [Table 1] (hereinafter, referred to as "compound group SX215").

The compound (L-10), wherein Het$^1$ represents H-18, and R$^1$ represents a substituent indicated in any of [Table 1] (hereinafter, referred to as "compound group SX216").

The compound (L-10), wherein Het$^1$ represents H-19, and R$^1$ represents a substituent indicated in any of [Table 2] (hereinafter, referred to as "compound group SX217").

The compound (L-10), wherein Het$^1$ represents H-20, and R$^1$ represents a substituent indicated in any of [Table 2] (hereinafter, referred to as "compound group SX218").

The compound (L-10), wherein Het$^1$ represents H-21, and R$^1$ represents a substituent indicated in any of [Table 2] (hereinafter, referred to as "compound group SX219").

The compound (L-10), wherein Het$^1$ represents H-22, and R$^1$ represents a substituent indicated in any of [Table 2] (hereinafter, referred to as "compound group SX220").

A compound represented by formula (L-11):

(L-11)

(hereinafter, referred to as "compound (L-11)"),
wherein Het$^1$ represents H-1, and R$^1$ represents a substituent indicated in any of [Table 1] to [Table 3] (hereinafter, referred to as "compound group SX221").

The compound (L-11), wherein Het$^1$ represents H-2, and R$^1$ represents a substituent indicated in any of [Table 1] to [Table 3] (hereinafter, referred to as "compound group SX222").

The compound (L-11), wherein Het$^1$ represents H-3, and R$^1$ represents a substituent indicated in any of [Table 1] to [Table 3] (hereinafter, referred to as "compound group SX223").

The compound (L-11), wherein Het$^1$ represents H-4, and R$^1$ represents a substituent indicated in any of [Table 1] to [Table 3] (hereinafter, referred to as "compound group SX224").

The compound (L-11), wherein Het$^1$ represents H-5, and R$^1$ represents a substituent indicated in any of [Table 1] to [Table 3] (hereinafter, referred to as "compound group SX225").

The compound (L-11), wherein Het¹ represents H-6, and R¹ represents a substituent indicated in any of [Table 1] (hereinafter, referred to as "compound group SX226").

The compound (L-11), wherein Het¹ represents H-7, and R¹ represents a substituent indicated in any of [Table 1] (hereinafter, referred to as "compound group SX227").

The compound (L-11), wherein Het¹ represents H-8, and R¹ represents a substituent indicated in any of [Table 1] (hereinafter, referred to as "compound group SX228").

The compound (L-11), wherein Het¹ represents H-9, and R¹ represents a substituent indicated in any of [Table 1] (hereinafter, referred to as "compound group SX229").

The compound (L-11), wherein Het¹ represents H-10, and R¹ represents a substituent indicated in any of [Table 1] (hereinafter, referred to as "compound group SX230").

The compound (L-11), wherein Het¹ represents H-11, and R¹ represents a substituent indicated in any of [Table 1] (hereinafter, referred to as "compound group SX231").

The compound (L-11), wherein Het¹ represents H-12, and R¹ represents a substituent indicated in any of [Table 1] (hereinafter, referred to as "compound group SX232").

The compound (L-11), wherein Het¹ represents H-13, and R¹ represents a substituent indicated in any of [Table 1] (hereinafter, referred to as "compound group SX233").

The compound (L-11), wherein Het¹ represents H-14, and R¹ represents a substituent indicated in any of [Table 1] (hereinafter, referred to as "compound group SX234").

The compound (L-11), wherein Het¹ represents H-15, and R¹ represents a substituent indicated in any of [Table 1] (hereinafter, referred to as "compound group SX235").

The compound (L-11), wherein Het¹ represents H-16, and R¹ represents a substituent indicated in any of [Table 1] (hereinafter, referred to as "compound group SX236").

The compound (L-11), wherein Het¹ represents H-17, and R¹ represents a substituent indicated in any of [Table 1] (hereinafter, referred to as "compound group SX237").

The compound (L-11), wherein Het¹ represents H-18, and R¹ represents a substituent indicated in any of [Table 1] (hereinafter, referred to as "compound group SX238").

The compound (L-11), wherein Het¹ represents H-19, and R¹ represents a substituent indicated in any of [Table 2] (hereinafter, referred to as "compound group SX239").

The compound (L-11), wherein Het¹ represents H-20, and R¹ represents a substituent indicated in any of [Table 2] (hereinafter, referred to as "compound group SX240").

The compound (L-11), wherein Het¹ represents H-21, and R¹ represents a substituent indicated in any of [Table 2] (hereinafter, referred to as "compound group SX241").

The compound (L-11), wherein Het¹ represents H-22, and R¹ represents a substituent indicated in any of [Table 2] (hereinafter, referred to as "compound group SX242").

A compound represented by formula (L-12):

(L-12)

(hereinafter, referred to as "compound (L-12)"),
wherein Het¹ represents H-1, and R¹ represents a substituent indicated in any of [Table 1] to [Table 3] (hereinafter, referred to as "compound group SX243").

The compound (L-12), wherein Het¹ represents H-2, and R¹ represents a substituent indicated in any of [Table 1] to [Table 3] (hereinafter, referred to as "compound group SX244").

The compound (L-12), wherein Het¹ represents H-3, and R¹ represents a substituent indicated in any of [Table 1] to [Table 3] (hereinafter, referred to as "compound group SX245").

The compound (L-12), wherein Het¹ represents H-4, and R¹ represents a substituent indicated in any of [Table 1] to [Table 3] (hereinafter, referred to as "compound group SX246").

The compound (L-12), wherein Het¹ represents H-5, and R¹ represents a substituent indicated in any of [Table 1] to [Table 3] (hereinafter, referred to as "compound group SX247").

The compound (L-12), wherein Het¹ represents H-6, and R¹ represents a substituent indicated in any of [Table 1] (hereinafter, referred to as "compound group SX248").

The compound (L-12), wherein Het¹ represents H-7, and R¹ represents a substituent indicated in any of [Table 1] (hereinafter, referred to as "compound group SX249").

The compound (L-12), wherein Het¹ represents H-8, and R¹ represents a substituent indicated in any of [Table 1] (hereinafter, referred to as "compound group SX250").

The compound (L-12), wherein Het¹ represents H-9, and R¹ represents a substituent indicated in any of [Table 1] (hereinafter, referred to as "compound group SX251").

The compound (L-12), wherein Het¹ represents H-10, and R¹ represents a substituent indicated in any of [Table 1] (hereinafter, referred to as "compound group SX252").

The compound (L-12), wherein Het¹ represents H-11, and R¹ represents a substituent indicated in any of [Table 1] (hereinafter, referred to as "compound group SX253").

The compound (L-12), wherein Het¹ represents H-12, and R¹ represents a substituent indicated in any of [Table 1] (hereinafter, referred to as "compound group SX254").

The compound (L-12), wherein Het¹ represents H-13, and R¹ represents a substituent indicated in any of [Table 1] (hereinafter, referred to as "compound group SX255").

The compound (L-12), wherein Het¹ represents H-14, and R¹ represents a substituent indicated in any of [Table 1] (hereinafter, referred to as "compound group SX256").

The compound (L-12), wherein Het¹ represents H-15, and R¹ represents a substituent indicated in any of [Table 1] (hereinafter, referred to as "compound group SX257").

The compound (L-12), wherein Het¹ represents H-16, and R¹ represents a substituent indicated in any of [Table 1] (hereinafter, referred to as "compound group SX258").

The compound (L-12), wherein Het¹ represents H-17, and R¹ represents a substituent indicated in any of [Table 1] (hereinafter, referred to as "compound group SX259").

The compound (L-12), wherein Het¹ represents H-18, and R¹ represents a substituent indicated in any of [Table 1] (hereinafter, referred to as "compound group SX260").

The compound (L-12), wherein Het¹ represents H-19, and R¹ represents a substituent indicated in any of [Table 2] (hereinafter, referred to as "compound group SX261").

The compound (L-12), wherein Het¹ represents H-20, and R¹ represents a substituent indicated in any of [Table 2] (hereinafter, referred to as "compound group SX262").

The compound (L-12), wherein Het¹ represents H-21, and R¹ represents a substituent indicated in any of [Table 2] (hereinafter, referred to as "compound group SX263").

The compound (L-12), wherein Het¹ represents H-22, and R¹ represents a substituent indicated in any of [Table 2] (hereinafter, referred to as "compound group SX264").

The present compound can be mixed or combined with an insecticide, a miticide, a nematicide, a fungicide, a plant growth modulator, and a synergist as recited below. Examples of combinations of compounds which can be mixed or combined with the present compound are recited. The abbreviation "SX" means to "any one of the present compounds selected from the compound groups SX1 to SX264". The number in parentheses represents CAS register number.

Clothianidin (205510-53-8)+SX, thiamethoxam (153719-23-4)+SX, imidacloprid (138261-41-3)+SX, thiacloprid (111988-49-9)+SX, flupyradifurone (951659-40-8)+SX, sulfoxaflor (946578-00-3)+SX, triflumezopyrim (1263133-33-0)+SX, dicloromezotiaz (1263629-39-5)+SX, beta-cyfluthrin (68359-37-5)+SX, tefluthrin (79538-32-2)+SX, fipronil (120068-37-3)+SX, chlorantraniliprole (500008-45-7)+SX, cyantraniliprole (736994-63-1)+SX, tetraniliprole (1229654-66-3)+SX, cyclaniliprole (1031756-98-5)+SX, thiodicarb (59669-26-0)+SX, carbofuran (1563-66-2)+SX, fluxametamide (928783-29-3)+SX, afoxolaner (1093861-60-9)+SX, fluralaner (864731-61-3)+SX, broflanilide (1207727-04-5)+SX, tebuconazole (107534-96-3)+SX, prothioconazole (178928-70-6)+SX, metconazole (125116-23-6)+SX, ipconazole (125225-28-7)+SX, triticonazole (131983-72-7)+SX, difenoconazole (119446-68-3)+SX, imazalil (35554-44-0)+SX, triadimenol (55219-65-3)+SX, tetraconazole (112281-77-3)+SX, flutriafol (76674-21-0)+SX, mandestrobin (173662-97-0)+SX, azoxystrobin (131860-33-8)+SX, pyraclostrobin (175013-18-0)+SX, trifloxystrobin (141517-21-7)+SX, fluoxastrobin (193740-76-0)+SX, picoxystrobin (117428-22-5)+SX, fenamidone (161326-34-7)+SX, metalaxyl (57837-19-1)+SX, metalaxyl-M (70630-17-0)+SX, fludioxonil (131341-86-1)+SX, sedaxane (874967-67-6)+SX, penflufen (494793-67-8)+SX, fluxapyroxad (907204-31-3)+SX, fluopyram (658066-35-4)+SX, benzovindiflupyr (1072957-71-1)+SX, boscalid (188425-85-6)+SX, carboxin (5234-68-4)+SX, penthiopyrad (183675-82-3)+SX, flutolanil (66332-96-5)+SX, captan (133-06-2)+SX, thiram (137-26-8)+SX, tolclofos-methyl (57018-04-9)+SX, thiabendazole (148-79-8)+SX, ethaboxam (162650-77-3)+SX, mancozeb (8018-01-7)+SX, picarbutrazox (500207-04-5)+SX, oxathiapiprolin (1003318-67-9)+SX, silthiofam (175217-20-6)+SX, abamectin (71751-41-2)+SX, fluensulfone (318290-98-1)+SX, fluazaindolizine (1254304-22-7)+SX, tioxazafen (330459-31-9)+SX, 3-difluoromethyl-1-methyl-N-(1,1,3-trimethylindan-4-yl)pyrazole-4-carboxamide (141573-94-6)+SX, 3-difluoromethyl-1-methyl-N-[(3R)-1,1,3-trimethylindan-4-yl]pyrazole-4-carboxamide (1352994-67-2)+SX, the compound represented by the following formula:

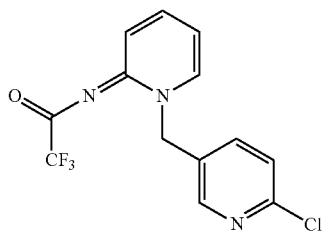 [SMILES: O=C(N=c1ccccn1Cc1ccc(Cl)nc1)C(F)(F)F]

(1689566-03-7)+SX, *Mycorrhiza Fungi*+SX, *Bacillus firmus*+SX, *Bacillus amyloliquefaciens*+SX, *Pasteuria nishizawae*+SX, *Pasteuria penetrans*+SX.

Examples of the harmful arthropod on which the present compound has a control efficacy include harmful insects and harmful mites. Specific examples of such harmful arthropod are recited as follows.

Hemiptera Pests:

Delphacidae (for example, *Laodelphax striatellus, Nilaparvata lugens, Sogatella furcifera, Peregrinus maidis, Javesella pellucida, Perkinsiella saccharicida,* and *Tagosodes orizicolus*);

Cicadellidae (for example, *Nephotettix cincticeps, Nephotettix virescens, Nephotettix nigropictus, Recilia dorsalis, Empoasca onukii, Empoasca fabae, Dalbulus maidis,* and *Cofana spectra*);

Cercopidae (for example, *Mahanarva posticata,* and *Mahanarva fimbriolata*);

Aphididae (for example, *Aphis fabae, Aphis glycines, Aphis gossypii, Aphis pomi, Aphis spiraecola, Myzus persicae, Brachycaudus helichrysi, Brevicoryne brassicae, Dysaphis plantaginea* (Rosy apple aphid), *Lipaphis erysimi, Macrosiphum euphorbiae, Aulacorthum solani, Nasonovia ribisnigri, Rhopalosiphum padi, Rhopalosiphum maidis, Toxoptera citricidus, Hyalopterus pruni, Melanaphis sacchari, Tetraneura nigriabdominalis, Ceratovacuna lanigera,* and *Eriosoma lanigerum*);

Phylloxeridae (for example, *Daktulosphaira vitifoliae, Phylloxera devastatrix* (Pecan *phylloxera*), *Phylloxera notabilis* (Pecan leaf *phylloxera*), and *Phylloxera russellae* (Southern pecan leaf *phylloxera*));

Adelgidae (for example, *Adelges tsugae, Adelges piceae,* and *Aphrastasia pectinatae*);

Pentatomidae (for example, *Scotinophara lurida, Scotinophara coarctata* (Malayan rice black bug), *Nezara antennata, Eysarcoris aeneus, Eysarcoris lewisi, Eysarcoris ventralis, Eysarcoris annamita, Halyomorpha halys, Nezara viridula, Euschistus heros* (Brown stink bug), *Piezodorus guildinii* (Red banded stink bug), *Oebalus pugnax,* and *Dichelops melacanthus*);

Cydnidae (for example, *Scaptocoris castanea* (Burrower brown bug);

Alydidae (for example, *Riptortus pedestris, Leptocorisa chinensis,* and *Leptocorisa acuta*);

Coreidae (for example, *Cletus punctiger,* and *Leptoglossus australis*);

Lygaeidae (for example, *Caverelius saccharivorus, Togo hemipterus,* and *Blissus leucopterus*);

Miridae (for example, *Trigonotylus caelestialium, Stenotus rubrovittatus, Stenodema calcarata,* and *Lygus lineolaris*);

Aleyrodidae (for example, *Trialeurodes vaporariorum, Bemisia tabaci, Dialeurodes citri, Aleurocanthus spiniferus, Aleurocanthus camelliae,* and *Pealius euryae*);

Diaspididae (for example, *Abgrallaspis cyanophylli, Aonidiella aurantii, Diaspidiotus perniciosus, Pseudaulacaspis pentagona, Unaspis yanonensis,* and *Unaspis citri;*

Coccidae (for example, *Ceroplastes rubens*);

Margarodidae (for example, *Icerya purchasi,* and *Icerya seychellarum*);

Pseudococcidae (for example, *Phenacoccus solani, Phenacoccus solenopsis, Planococcus kraunhiae, Planococcus comstocki, Planococcus citri, Pseudococcus calceolariae, Pseudococcus longispinus,* and *Brevennia rehi*);

Psyllidae (for example, *Diaphorina citri, Trioza erytreae, Cacopsylla pyrisuga, Cacopsylla chinensis, Bactericera cockerelli,* and *Cacopsylla pyricola* (Pear *psylla*));

Tingidae (for example, *Corythucha ciliata, Corythucha marmorata, Stephanitis nashi,* and *Stephanitis pyrioides*);

Cimicidae (for example, *Cimex lectularius*); and

Cicadidae (for example, *Quesada gigas* (Giant Cicada)); and others.

Lepidoptera Pests:

Crambidae (for example, *Chilo suppressalis*, *Chilo polychrysus* (Darkheaded stem borer), *Scirpophaga innotata* (White stem borer), *Scirpophaga incertulas*, *Rupela albina*, *Cnaphalocrocis medinalis*, *Marasmia patnalis*, *Marasmia exigua*, *Notarcha derogata*, *Ostrinia furnacalis*, *Ostrinia nubilalis* (European corn borer), *Hellula undalis*, *Herpetogramma luctuosale*, *Pediasia teterrellus*, *Nymphula depunctalis*, and *Diatraea saccharalis* (Sugarcane borer));

Pyralidae (for example, *Elasmopalpus lignosellus*, and *Plodia interpunctella*);

Noctuidae (for example, *Spodoptera litura*, *Spodoptera exigua*, *Mythimna separata*, *Mamestra brassicae*, *Sesamia inferens*, *Spodoptera mauritia*, *Naranga aenescens*, *Spodoptera frugiperda*, *Spodoptera exempta*, *Agrotis Autographa nigrisigna*, *Plusia festucae*, *Chrysodeixis includens* (Soybean looper), *Trichoplusia* spp., *Heliothis* spp. such as *Heliothis virescens*, *Helicoverpa armigera*, *Helicoverpa* spp. such as *Helicoverpa zea*, *Anticarsia gemmatalis* (Velvetbean caterpillar), *Alabama argillacea* (Cotton leafworm), and *Hydraecia immanis* (Hop vine borer));

Pieridae (for example, *Pieris rapae*);

Tortricidae (for example, *Grapholita molesta*, *Grapholita dimorpha*, *Leguminivora glycinivorella*, *Matsumuraeses azukivora*, *Adoxophyes orana fasciata*, *Adoxophyes honmai*, *Homona magnanima*, *Archips fuscocupreanus*, *Cydia pomonella*, *Tetramoera schistaceana*, *Epinotia aporema* (Bean Shoot Borer), and *Ecdytolopha aurantiana* (Citrus fruit borer));

Gracillariidae (for example, *Caloptilia theivora*, and *Phyllonorycter ringoniella*);

Carposinidae (for example, *Carposina sasakii*);

Lyonetiidae (for example, *Leucoptera coffeela* (Coffee Leaf miner), *Lyonetia clerkella*, and *Lyonetia prunifoliella*);

Lymantriidae (for example, *Lymantria* spp. such as *Lymantria dispar*, and *Euproctis* spp. such as *Euproctis pseudoconspersa*);

Pluteliidae (for example, *Plutella xylostella*);

Gelechiidae (for example, *Anarsia lineatella*, *Helcystogramma triannulellum*, *Pectinophora gossypiella*, *Phthorimaea operculella*, and *Tuta absoluta*);

Arctiidae (for example, *Hyphantria cunea*);

Castniidae (for example, *Telchin licus* (Giant Sugarcane borer));

Cossidae (for example, *Cosus insularis*);

Geometridae (for example, *Ascotis selenaria*);

Limacodidae (for example, *Parasa lepida*);

Stathmopodidae (for example, *Stathmopoda masinissa*);

Sphingidae (for example, *Acherontia lachesis*);

Sesiidae (for example, *Nokona feralis*);

Hesperiidae (for example, *Parnara guttata*); and others.

Thysanoptera Pests:

Thripidae (for example, *Frankliniella occidentalis*, *Thrips palmi*, *Scirtothrips dorsalis*, *Thrips tabaci*, *Frankliniella intonsa*, *Stenchaetothrips biformis*, and *Echinothrips americanus*;

Phlaeothripidae (for example, *Haplothrips aculeatus*); and others.

Diptera Pests:

Anthomyiidae (for example, *Delia platura*, and *Delia antiqua*);

Ulidiidae (for example, *Tetanops myopaeformis*);

Agromyzidae (for example, *Agromyza oryzae*, *Liriomyza sativae*, *Liriomyza trifolii*, and *Chromatomyia horticola*);

Chloropidae (for example, *Chlorops oryzae*);

Tephritidae (for example, *Bactrocera cucurbitae*, *Bactrocera dorsalis*, *Bactrocera latifrons*, *Bactrocera oleae*, *Bactrocera tryoni*, and *Ceratitis capitata*);

Ephydridae (for example, *Hydrellia griseola*, *Hydrellia philippina*, and *Hydrellia sasakii*);

Drosophilidae (for example, *Drosophila suzukii*);

Phoridae (for example, *Megaselia spiracularis*);

Psychodidae (for example, *Clogmia albipunctata*);

Sciaridae (for example, *Bradysia difformis*);

Cecidomyiidae (for example, *Mayetiola destructor*, and *Orseolia oryzae*;

Diopsidae (for example, *Diopsis macrophthalma*);

Tipulidae (for example, *Tipula aino*, *Tipula oleracea* (Common cranefly), and *Tipula paludosa* (European cranefly)); and others.

Coleoptera Pests:

Chrysomelidae (for example, *Diabrotica virgifera virgifera*, *Diabrotica undecimpunctata howardi*, *Diabrotica barberi*, *Diabrotica virgifera zeae*, *Diabrotica balteata*, *Diabrotica speciosa* (Cucurbit Beetle), *Cerotoma trifurcata*, *Oulema melanopus*, *Aulacophora femoralis*, *Phyllotreta striolata*, *Leptinotarsa decemlineata*, *Oulema oryzae*, *Colaspis brunnea*, *Chaetocnema pulicaria*, *Chaetocnema confi*, *Epitrix cucumeris*, *Dicladispa armigera*, *Colaspis brunnea* (Grape *Colaspis*), *Myochrous denticollis* (southern corn leaf beetle), *Laccoptera quadrimacu*, and *Epitrix hirtipennis*;

Carabidae (for example, *Stenolophus lecontei* (Seedcorn beetle), and *Clivina impressifrons* (Slender seedcorn beetle));

Scarabaeidae (for example, *Anomala cuprea*, *Anomala rufocuprea*, *Anomala albopilosa*, *Popillia japonica*, *Heptophylla picea*, *Rhizotrogus majalis* (European Chafer), *Tomarus gibbosus*, *Holotrichia* spp., and *Phyllophaga* spp. such as *Phyllophaga crinita*);

Curculionidae (for example, *Araecerus coffeae*, *Cylas formicarius*, *Euscepes postfasciatus*, *Hypera postica*, *Sitophilus zeamais*, *Echinocnemus squameus*, *Lissorhoptrus oryzophilus*, *Rhabdoscelus lineatocollis*, *Anthonomus grandis*, *Sphenophorus venatus*, *Sphenophorus callosus* (Southern Corn Billbug), *Sternechus subsignatus* (Soybean stalk weevil), *Sphenophorus levis* (Sugarcane wiivil), *Scepticus griseus*, *Scepticus uniformis*, *Zabrotes subfasciatus*, *Tomicus piniperda*, and *Hypothenemus hampei* (Coffee Berry Borer));

Tenebrionidae (for example, *Tribolium castaneum*, and *Tribolium confusum*);

Coccinellidae (for example, *Epilachna vigintioctopunctata*);

Bostrychidae (for example, *Lyctus brunneus*);

Ptinidae;

Cerambycidae (for example, *Anoplophora malasiaca*, and *Migdolus fryanus*);

Elateridae (*Agriotes* sp., *Aelous* sp., *Anchastus* sp., *Melanotus* sp., *Limonius* sp., *Conoderus* sp., *Ctenicera* sp.) (for example, *Melanotus okinawensis*, *Agriotes fuscicollis*, and *Melanotus legatus*);

Staphylinidae (for example, *Paederus fuscipes*); and others.

Orthoptera Pests:

Acrididae (for example, *Locusta migratoria*, *Dociostaurus maroccanus*, *Chortoicetes terminifera*, *Nomadacris septemfasciata*, *Locustana pardalina* (Brown Locust), *Anacridium melanorhodon* (Tree Locust), *Calliptamus italicus* (Italian Locust), *Melanoplus differentialis* (Differential grasshopper), *Melanoplus bivittatus* (Two striped grasshopper), *Melanoplus sanguinipes* (Migratory grasshopper),

*Melanoplus femurrubrum* (Red-Legged grasshopper), *Camnula pellucida* (Clearwinged grasshopper), *Schistocerca gregaria, Gastrimargus musicus* (Yellow-winged locust), *Austracris guttulosa* (Spur-throated locust), *Oxya yezoensis, Oxya japonica*, and *Patanga succincta*);

Gryllotalpidae (for example, *Gryllotalpa africana*);

Gryllidae (for example, *Acheta domesticus*, and *Teleogryllus emma*);

Tettigoniidae (for example, *Anabrus simplex* (Mormon cricket)); and others.

Hymenoptera Pests:

Tenthredinidae (for example, *Athalia rosae*, and *Athalia japonica*);

Formicidae (for example, *Solenopsis* spp. and *Atta capiguara* (Brown leaf-cutting ant)); and others.

Blattodea Pests:

Blattellidae (for example, *Blattella germanica*);

Blattidae (for example, *Periplaneta fuliginosa, Periplaneta americana, Periplaneta brunnea*, and *Blatta orientalis*);

Termitidae (for example, *Reticulitermes speratus, Coptotermes formosanus, Incisitermes minor, Cryptotermes domesticus, Odontotermes formosanus, Neotermes koshunensis, Glyptotermes satsumensis, Glyptotermes nakajimai, Glyptotermes fuscus, Hodotermopsis sjostedti, Coptotermes guangzhouensis, Reticulitermes amamianus, Reticulitermes miyatakei, Reticulitermes kanmonensis, Nasutitermes takasagoensis, Pericapritermes nitobei, Sinocapritermes mushae*, and *Cornitermes cumulans*); and others.

Acari Pests:

Tetranychidae (for example, *Tetranychus urticae, Tetranychus kanzawai, Tetranychus evansi, Panonychus citri, Panonychus ulmi*, and *Oligonychus* spp.);

Eriophyidae (for example, *Aculops pelekassi, Phyllocoptruta citri, Aculops lycopersici, Calacarus carinatus, Acaphylla theavagrans, Eriophyes chibaensis, Aculus schlechtendali, Aceria diospyri, Aceria tosichella*, and *Shevtchenkella* sp.);

Tarsonemidae (for example, *Polyphagotarsonemus latus*);

Tenuipalpidae (for example, *Brevipalpus phoenicis*);

Tuckerellidae;

Ixodidae (for example, *Haemaphysalis longicornis, Haemaphysalis flava, Dermacentor taiwanensis, Dermacentor variabilis, Ixodes ovatus, Ixodes persulcatus, Ixodes scapularis, Amblyomma americanum, Boophilus microplus*, and *Rhipicephalus sanguineus*);

Acaridae (for example, *Tyrophagus putrescentiae*, and *Tyrophagus similis*);

Pyroglyphidae (for example, *Dermatophagoides farinae*, and *Dermatophagoides pteronyssinus*);

Cheyletidae (for example, *Cheyletus eruditus, Cheyletus malaccensis, Cheyletus moorei*, and *Cheyletiella yasguri*);

Sarcoptidae (for example, *Otodectes cynotis*, and *Sarcoptes scabiei*);

Demodicidae (for example, *Demodex canis*);

Listrophoridae;

Haplochthoniidae;

Macronyssidae (for example, *Ornithonyssus bacoti*, and *Ornithonyssus sylviarum*);

Dermanyssidae (for example, *Dermanyssus gallinae*);

Trombiculidae (for example, *Leptotrombidium akamushi*); and others.

An agent for controlling harmful arthropods of the present invention comprises the present compound and an inert carrier. The agent for controlling harmful arthropods is usually prepared by mixing the present compound with an inert carrier such as solid carrier, liquid carrier and gaseous carrier, and if necessary, adding surfactants and other auxiliary agents for formulation to formulate them into emulsifiable concentrates, oil solutions, powders, granules, wettable powders, flowables, microcapsules, aerosols, smoking agents, poison baits, resin formulations, shampoo formulations, paste-like formulations, foams, carbon dioxide formulations, tablets, and the others. Such formulations may be processed into mosquito repellent coils, electric mosquito repellent mats, liquid mosquito formulations, smoking agents, fumigants, sheet formulations, spot-on formulations or formulations for oral treatment to use. Also, the agent for controlling harmful arthropods of the present invention may be mixed with other insecticides, miticides, nematicides, fungicides, plant growth modulators, herbicides, and synergists.

The agent for controlling harmful arthropods of the present invention comprises usually 0.01 to 95% by weight of the present compound.

Examples of the solid carrier to be used in the formulation include fine powders or granules such as clays (for example, kaolin clay, diatomaceous earth, bentonite, Fubasami clay, or acid white clay), synthetic hydrous silicon oxides, talcs, ceramics, other inorganic minerals (for example, sericite, quartz, sulfur, active carbon, calcium carbonate, or hydrated silica) and chemical fertilizers (for example, ammonium sulfate, ammonium phosphate, ammonium nitrate, urea, or ammonium chloride); as well as synthetic resins (for example, polyester resins such as polypropylene, polyacrylonitrile, polymethyl methacrylate and polyethylene terephthalate; nylon resins such as nylon-6, nylon-11 and nylon-66; polyamide resins; polyvinyl chloride, polyvinylidene chloride, vinyl chloride-propylene copolymers, and the others).

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile, or isobutyronitrile); ethers (for example, diisopropyl ether, 1,4-dioxane, DME, diethylene glycol dimethyl ether, diethylene glycol monomethyl ether, propylene glycol monomethyl ether, dipropylene glycol monomethyl ether, or 3-methoxy-3-methyl-1-butanol); acid amides (for example, DMF, or dimethylacetamide); halogenated hydrocarbons (for example, dichloromethane, trichloroethane, or carbon tetrachloride); sulfoxides (for example, DMSO); propylene carbonate; and vegetable oils (for example, soybean oil, or cottonseed oil).

Examples of the gaseous carrier include fluorocarbon, butane gas, LPG (liquefied petroleum gas), dimethyl ether, and carbon dioxide gas.

Examples of the surfactant include nonionic surfactants such as polyoxyethylenated alkyl ethers, polyoxyethylenated alkyl aryl ethers and polyethylene glycol fatty acid esters; and anionic surfactants such as alkyl sulfonates, alkylbenzene sulfonates and alkyl sulfates.

Examples of other auxiliary agent for formulation include a binder, a dispersant, a colorant, and a stabilizer. Specific examples include casein, gelatin, polysaccharides (for example, starch, gum arabic, cellulose derivatives, and alginic acid), lignin derivatives, bentonite, water-soluble synthetic polymers (for example, polyvinyl alcohol, polyvinyl pyrrolidone, and polyacrylic acids), PAP (acidic isopropyl phosphate), BHT (2,6-di-tert-butyl-4-methylphenol), and BHA (a mixture of 2-tert-butyl-4-methoxyphenol and 3-tert-butyl-4-methoxyphenol).

Examples of a base material of the resin formulation include polyvinyl chloride polymers, polyurethane, and the others, and a plasticizer such as phthalate esters (for example, dimethyl phthalate, and dioctyl phthalate), adipic acid esters and stearic acid may be added to the base material, if necessary. The resin formulation can be prepared by kneading the present compound in the base material with a conventional kneading machine, and then molding it by injection molding, extrusion molding or pressure molding and the like. The resultant resin formulation can be subjected to further molding or cutting procedure, if necessary, to be processed into shapes such as a plate, film, tape, net and string shape. The resin formulation can be processed into animal collars, animal ear tags, sheet products, trap strings, gardening supports, and other products.

Examples of a base material for the poison bait include bait ingredients such as grain powder, vegetable oil, saccharide and crystalline cellulose, and if necessary, with an addition of antioxidants such as dibutylhydroxytoluene and nordihydroguaiaretic acid, preservatives such as dehydroacetic acid, accidental ingestion inhibitors for children and pets such as a chili powder, and insect attraction fragrances such as cheese flavor, onion flavor and peanut oil.

The method for controlling harmful arthropods of the present invention is conducted by applying an effective amount of the present compound to a harmful arthropod directly and/or a habitat where the harmful arthropod lives (for example, plant bodies, soil, an interior of a house, and animal bodies). In the method for controlling harmful arthropods of the present invention, the present compound is usually used in the form of a harmful arthropod controlling agent.

When the agent for controlling harmful arthropods of the present invention is used for controlling harmful arthropods in an agricultural field, an applied dose as an amount of the present compound is usually within a range from 1 to 10,000 g per 10,000 m$^2$. The emulsifiable concentrate, the wettable powder, or the flowable formulation etc. of the agent for controlling harmful arthropods of the present invention is usually applied by diluting it with water in such a way that a concentration of the active ingredient of the present invention is within a range from 0.01 to 10,000 ppm. The granular formulation, or the powder formulation etc., is usually applied as itself without diluting it.

These formulations and diluents of the formulations with water may be directly sprayed to a harmful arthropod or a plant such as a crop to be protected from the harmful arthropod, or applied to a soil in a cultivated area to control the harmful arthropod that inhabits the soil.

Also, the resin formulation processed into a sheet shape or string shape may be wrapped around a crop, stretched near a crop, spread on a foot soil of a plant, or the like.

When the agent for controlling harmful arthropods of the present invention is used to control harmful arthropods that live inside a house, an applied dose as an amount of the present compound is usually within a range from 0.01 to 1,000 mg per 1 m$^2$ of an area to be treated, in the case of using it on a planar area. In the case of using it spatially, the applied dose as an amount of the present compound is usually within a range from 0.01 to 500 mg per 1 m$^3$ of the space to be treated. When the agent for controlling harmful arthropods of the present invention is formulated into emulsifiable concentrates, wettable powders, flowables or the others, the formulation is usually applied after diluting it with water in such a way that a concentration of the active ingredient is within a range from 0.1 to 10,000 ppm, and then sparging it. In the case of being formulated into oil solutions, aerosols, smoking agents, poison baits and the others, the formulation is used as itself without diluting it.

When the agent for controlling harmful arthropods of the present invention is used for controlling external parasites of livestock such as cows, horses, pigs, sheep, goats and chickens, and small animals such as dogs, cats, rats and mice, the pest control agent of the present invention can be applied to the animal by a known method in the veterinary field. Specifically, when systemic control is intended, the pest control agent of the present invention is administered to the animal as a tablet, a mixture with feed or a suppository, or by injection (including intramuscular, subcutaneous, intravenous and intraperitoneal injections). On the other hand, when non-systemic control is intended, the pest control agent of the present invention is applied to the animal by means of spraying of the oil solution or aqueous solution, pour-on or spot-on treatment, or washing of the animal with a shampoo formulation, or by putting a collar or ear tag made of the resin formulation to the animal. In the case of administering to an animal body, the dose of the present compound is usually within a range from 0.1 to 1,000 mg per 1 kg of a body weight of the animal.

EXAMPLES

The following examples including Preparation examples, Formulation examples and Test examples serve to describe the present invention in more detail, which should not intend to limit the present invention.

Firstly, for the preparation of the present compound, Preparation examples are shown as follows.

Reference Preparation Example 1

To a mixture of 3-chloropyridine-2-carbonitrile 54 g and THF 300 mL, 1M methylmagnesium bromide in THF solution 500 mL was added dropwise under ice-cooling. The reaction mixture was stirred under ice-cooling for 2 hours. The obtained mixture was added to 2N hydrochloric acid under ice-cooling and stirred for 30 minutes. To the mixture was added 1N sodium hydroxide solution, and then the mixture was adjusted to pH 8 and extracted with ethyl acetate. The resulting organic layer was washed with saturated brine, and then the organic layer was dried over anhydrous sodium sulfate. The organic layer was concentrated under reduced pressure to give the intermediate compound 1 shown below 58 g.

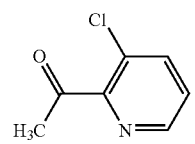

The intermediate compound 1: $^1$H-NMR (CDCl$_3$) δ: 8.55 (1H, dd), 7.80 (1H, dd), 7.38 (1H, dd), 2.70 (3H, s).

Reference Preparation Example 2

To a mixture of sodium hydride (oily, 60%) 57 g and DMF 560 mL, ethanethiol 100 mL was added dropwise under ice-cooling. To the obtained mixture, a mixed solution of the intermediate compound 1 204 g and DMF 190 mL was added dropwise under ice-cooling. The obtained mixture was stirred under ice-cooling for one hour and then added to ice-water. The precipitated solid was filtered and washed with water. The obtained solid was dissolved in ethyl acetate, and the solution was washed with saturated brine, dried over sodium sulfate, and concentrated under reduced pressure. The resulting solid was washed with hexane to give the intermediate compound 2 shown below 160 g.

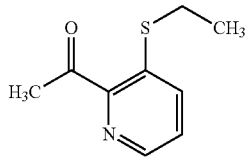

The intermediate compound 2: $^1$H-NMR (CDCl$_3$) δ: 8.40 (1H, dd), 7.69 (1H, dd), 7.37 (1H, dd), 2.92 (2H, q), 2.72 (3H, s), 1.40 (3H, t).

Reference Preparation Example 3

To a mixture of the intermediate compound 2 5.4 g, glyoxylic acid monohydrate 2.8 g, and methanol 90 mL, a mixture of sodium hydroxide 2.4 g and methanol 60 mL was added dropwise under ice-cooling. The mixture was stirred at 60° C. for 2 hours. The mixture was cooled to room temperature, and to the mixture were sequentially added acetic acid 11 mL and hydrazine monohydrate 2.3 g. The mixture was stirred at 100° C. for 19 hours. After the obtained mixture was cooled to room temperature, saturated ammonium chloride solution was added thereto, and the mixture was extracted with chloroform. The resulting organic layer was dried over sodium sulfate and concentrated under reduced pressure. The resulting residue was subjected to a silica gel chromatography to give the intermediate compound 3 shown below 3.8 g.

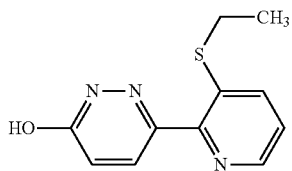 [SMILES: CCSc1cccnc1-c1ccc(O)nn1]

The intermediate compound 3: $^1$H-NMR (CDCl$_3$) δ: 10.60 (1H, br s), 8.43 (1H, dd), 8.13 (1H, d), 7.71 (1H, dd), 7.29 (1H, dd), 7.05 (1H, d), 2.95 (2H, q), 1.35 (3H, t).

Reference Preparation Example 4

To a mixture of the intermediate compound 3 2.0 g and toluene 9 mL, phosphoryl chloride 1.6 mL was added at room temperature. After the mixture was stirred at 100° C. for 2 hours, the mixture was cooled to room temperature and concentrated under reduced pressure. The resulting residue was diluted with chloroform, and then water was added thereto under ice-cooling, and the mixture was extracted with chloroform. The organic layer was washed with water and saturated brine sequentially, dried over sodium sulfate, and concentrated under reduced pressure to give the intermediate compound 4 shown below 2.2 g.

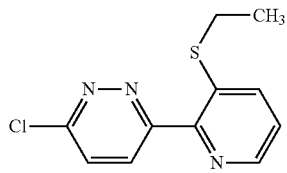 [SMILES: CCSc1cccnc1-c1ccc(Cl)nn1]

The intermediate compound 4: $^1$H-NMR (CDCl$_3$) δ: 8.48 (1H, dd), 8.25 (1H, d), 7.79 (1H, dd), 7.63 (1H, d), 7.34 (1H, dd), 2.95 (2H, q), 1.33 (3H, t).

Reference Preparation Example 5

The compounds prepared according to a similar method to that described in the Reference preparation example 4 and its physical properties are shown as follows.

A compound represented by formula (A-1):

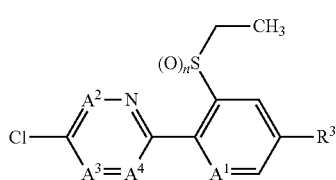

wherein, $A^1$, $A^2$, $A^3$, $A^4$, $R^3$, and n are shown in any of [Table 4].

TABLE 4

| Intermediate compound | $A^1$ | $A^2$ | $A^3$ | $A^4$ | $R^3$ | n |
|---|---|---|---|---|---|---|
| 5 | CH | N | CH | CH | CF$_3$ | 2 |
| 6 | N | CH | N | CH | H | 2 |

The intermediate compound 5: $^1$H-NMR (CDCl$_3$) δ: 8.47 (1H, t), 8.04 (1H, dt), 7.68 (1H, d), 7.63 (1H, d), 7.62 (1H, d), 3.45 (2H, q), 1.31 (3H, t).

The intermediate compound 6: $^1$H-NMR (CDCl$_3$) δ: 8.94 (1H, dd), 8.90 (1H, dd), 8.59 (1H, d), 8.52 (1H, d), 7.65 (1H, dd), 3.81 (2H, q), 1.39 (3H, t).

Reference Preparation Example 6

A mixture of 3-chloro-6-methoxypyridazine 17 g, 2-fluoro-4-(trifluoromethyl)phenylboronic acid pinacol ester 12 g, tetrakis(triphenylphosphine)palladium(0) 2.3 g, 2M sodium carbonate solution 50 mL, and DME 80 mL was stirred at 80° C. for 5 hours. After the mixture was cooled to room temperature, water was added thereto, and then the mixture was extracted with ethyl acetate. The organic layer was dried over anhydrous sodium sulfate and concentrated under reduced pressure. The resulting residue was subjected to a silica gel chromatography to give the intermediate compound 7 shown below 4.8 g.

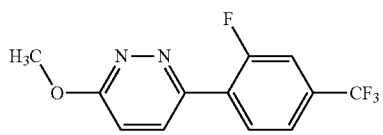 [SMILES: COc1ccc(-c2ccc(C(F)(F)F)cc2F)nn1]

The intermediate compound 7: $^1$H-NMR (CDCl$_3$) δ: 8.28 (1H, dd), 7.90 (1H, dd), 7.58 (1H, d), 7.47 (1H, d), 7.09 (1H, d), 4.21 (3H, s).

Reference Preparation Example 7

The following intermediate compound 8 was prepared according to a similar method to that described in the Reference preparation example 2 using the intermediate compound 7 instead of the intermediate compound 1.

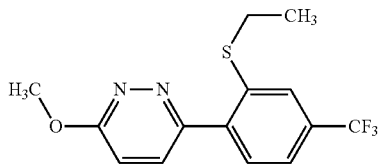 [SMILES: CCSc1cc(C(F)(F)F)ccc1-c1ccc(OC)nn1]

The intermediate compound 8: $^1$H-NMR (CDCl$_3$) δ: 7.72 (1H, d), 7.68-7.63 (2H, m), 7.55 (1H, d), 7.05 (1H, d), 4.21 (3H, s), 2.89 (2H, q), 1.25 (3H, t).

Reference Preparation Example 8

To a mixture of the intermediate compound 4 2.2 g and chloroform 43 mL, mCPBA (75%) 4.2 g was added under ice-cooling. The mixture was stirred at room temperature for 24 hours. To the mixture were added sodium sulfite 11 g and saturated sodium hydrogen carbonate solution, and the mixture was extracted with chloroform. The organic layer was dried over sodium sulfate and concentrated under reduced pressure. The resulting residue was subjected to a silica gel chromatography to give the intermediate compound 9 shown below 2.2 g.

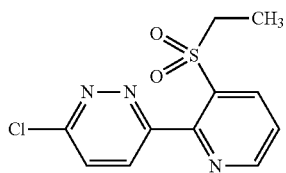 [SMILES: CCS(=O)(=O)c1cccnc1-c1ccc(Cl)nn1]

The intermediate compound 9: $^1$H-NMR (CDCl$_3$) δ: 8.93 (1H, dd), 8.54 (1H, dd), 7.95 (1H, d), 7.71 (1H, d), 7.66 (1H, dd), 3.89 (2H, q), 1.41 (3H, t).

Reference Preparation Example 9

The compound prepared according to a similar method to that described in the Reference preparation example 8 and its physical properties are shown as follows.

A compound represented by formula (A-2):

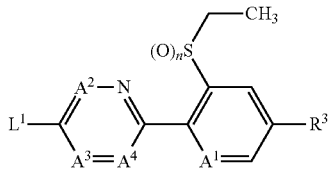

(A-2)

wherein, L$^1$, A$^1$, A$^2$, A$^3$, A$^4$, R$^3$, and n are shown in [Table 5].

TABLE 5

| Intermediate compound | L$^1$ | A$^1$ | A$^2$ | A$^3$ | A$^4$ | R$^3$ | n |
|---|---|---|---|---|---|---|---|
| 10 | OCH$_3$ | CH | N | CH | CH | CF$_3$ | 2 |

The intermediate compound 10: $^1$H-NMR (CDCl$_3$) δ: 8.45 (1H, s), 8.00 (1H, d), 7.60 (1H, d), 7.53 (1H, d), 7.12 (1H, d), 4.21 (3H, s), 3.46 (2H, q), 1.29 (3H, t).

Reference Preparation Example 10

A mixture of the intermediate compound 10 3.3 g and concentrated hydrochloric acid 25 mL was stirred while heating under reflux for one hour. After the mixture was cooled to room temperature, water was added thereto, and the precipitated solid was collected by filtration. The obtained solid was washed with water and concentrated under reduced pressure to give the intermediate compound 11 shown below 2.9 g.

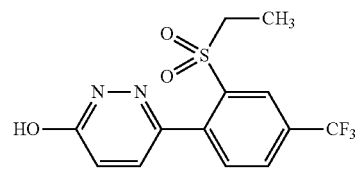 [SMILES: CCS(=O)(=O)c1cc(C(F)(F)F)ccc1-c1ccc(O)nn1]

The intermediate compound 11: $^1$H-NMR (CDCl$_3$) δ: 11.74 (1H, s), 8.41 (1H, s), 8.01 (1H, d), 7.62 (1H, d), 7.42 (1H, d), 7.06 (1H, d), 3.30 (2H, q), 1.30 (3H, t).

Reference Preparation Example 11

To a mixture of 1.6 M n-butyllithium-hexane solution 100 mL and THF 160 mL, a mixture of ethyl methyl sulfone 23 g and THF 20 mL was added dropwise at −78° C. After the mixture was gradually warmed to 0° C., the mixture was again cooled to −78° C. To the mixture, a mixture of 5-fluoro-2-cyanopyridine 20 g and THF 20 mL was added dropwise at −78° C. After the mixture was gradually warmed to room temperature, to the reaction mixture was added 2N hydrochloric acid, and the reaction mixture was stirred for 30 minutes. The obtained mixture was extracted with ethyl acetate, and the resulting organic layer was washed with saturated brine. The resulting organic layer was dried over anhydrous sodium sulfate and then concentrated under reduced pressure to give the intermediate compound 12 shown below 40 g.

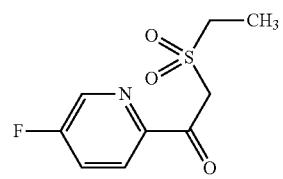

The intermediate compound 12: $^1$H-NMR (CDCl$_3$) δ: 8.57 (1H, d), 8.19 (1H, dd), 7.62-7.55 (1H, m), 4.97 (2H, s), 3.30 (2H, q), 1.47 (3H, t).

Reference Preparation Example 12

A mixture of methyl 5-chloro-2-pyrazinecarboxylate 10 g, sodium methoxide (28% methanol solution) 28 mL, and THF 100 mL was stirred under ice-cooling for 3 hours. To the mixture, ethyl methyl sulfone 18 mL was added under ice-cooling. The mixture was warmed to 80° C. and then stirred for 24 hours. After the mixture was cooled to room temperature, 2N hydrochloric acid was added thereto, and then the mixture was extracted with ethyl acetate. The organic layer was dried over anhydrous sodium sulfate and concentrated under reduced pressure. The resulting residue was subjected to a silica gel chromatography to give the intermediate compound 13 shown below 11 g.

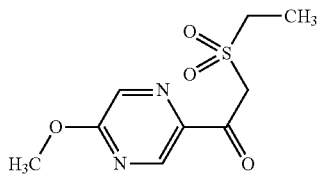 [SMILES: CCS(=O)(=O)CC(=O)c1cnc(OC)cn1]

The intermediate compound 13: $^1$H-NMR (CDCl$_3$) δ: 8.91 (1H, d), 8.25 (1H, d), 4.87 (2H, s), 4.08 (3H, s), 3.29 (2H, q), 1.47 (3H, t).

Reference Preparation Example 13

To a mixture of oxalyl chloride 11 mL and chloroform 86 mL, DMF 10 mL was added dropwise under ice-cooling, and the mixture was stirred for 30 minutes. To the mixture, butyl vinyl ether 33 mL was added dropwise, and the mixture was stirred at room temperature for 2 hours. To the mixture, a mixture of the intermediate compound 12 10 g, triethylamine 42 mL, and chloroform 30 mL was added dropwise under ice-cooling. After the mixture was warmed to room temperature, the mixture was stirred for one hour. To the mixture was added saturated ammonium chloride solution, and the mixture was extracted with chloroform. The organic layer was washed with water and saturated brine sequentially, dried over anhydrous sodium sulfate, and concentrated under reduced pressure. The resulting residue was dissolved in ethanol 30 mL, and 28% ammonium solution 10 mL was added thereto. The mixture was stirred at 60° C. for 2.5 hours. After the mixture was cooled to room temperature, to the mixture was added saturated sodium hydrogen carbonate solution, and the mixture was extracted with ethyl acetate. The organic layer was dried over anhydrous sodium sulfate and concentrated under reduced pressure. The resulting residue was subjected to a silica gel chromatography to give the intermediate compound 14 shown below 9.4 g.

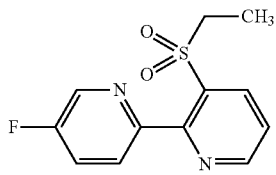 [SMILES: CCS(=O)(=O)c1cccnc1-c1ccc(F)cn1]

The intermediate compound 14: $^1$H-NMR (CDCl$_3$) δ: 8.88 (1H, dd), 8.52-8.46 (2H, m), 7.87 (1H, dd), 7.62-7.54 (2H, m), 3.86 (2H, q), 1.38 (3H, t).

Reference Preparation Example 14

The intermediate compound 15 was prepared according to a similar method to that described in the Reference preparation example 13 using the intermediate compound 13 instead of the intermediate compound 12. Its physical properties are shown as follows.

A compound represented by formula (A-3):

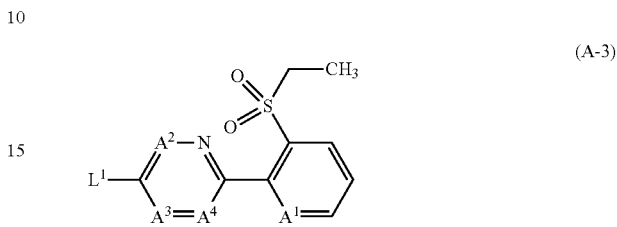

wherein, L$^1$, A$^1$, A$^2$, A$^3$, and A$^4$ are shown in [Table 6].

TABLE 6

| Intermediate compound | L$^1$ | A$^1$ | A$^2$ | A$^3$ | A$^4$ |
|---|---|---|---|---|---|
| 15 | OCH$_3$ | N | CH | N | CH |

The intermediate compound 15: $^1$H-NMR (CDCl$_3$) δ: 8.74 (1H, dd), 8.66 (1H, dd), 8.49 (1H, d), 8.20 (1H, d), 7.55 (1H, dd), 4.05 (3H, s), 3.85 (2H, q), 1.38 (3H, t).

Reference Preparation Example 15

A mixture of the intermediate compound 15 4.5 g and concentrated hydrochloric acid 20 mL was stirred at 100° C. for one hour. After the mixture was cooled to room temperature, 100 mL of ice-water was added thereto. The mixture was made to alkali by adding saturated sodium hydrogen carbonate solution, and the mixture was extracted with ethyl acetate. The organic layer was dried over anhydrous sodium sulfate and concentrated under reduced pressure. The resulting residue was subjected to a silica gel chromatography to give the intermediate compound 16 shown below 4.3 g.

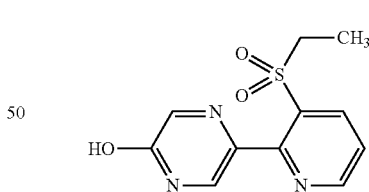

The intermediate compound 16: $^1$H-NMR (CDCl$_3$) δ: 12.4 (1H, bs), 8.80 (1H, dd), 8.46 (1H, dd), 8.20 (1H, d), 7.99 (1H, s), 7.50 (1H, dd), 3.83 (2H, q), 1.38 (3H, t).

Preparation Example 1

To a mixture of the intermediate compound 5 0.12 g and NMP 3.5 mL, cesium carbonate 290 mg and 3-(trifluoromethyl)pyrazole 57 mg were added at room temperature. The mixture was stirred at room temperature for 2 hours and then stirred at 80° C. for 10 minutes. After the mixture was cooled to room temperature, the mixture was concentrated under reduced pressure. To the resulting residue was added water, and the mixture was extracted with MTBE. The organic layer was washed with saturated brine, dried over anhydrous sodium sulfate, and concentrated under reduced pressure. The resulting residue was subjected to a silica gel chromatography to give the present compound 1 shown below 0.90 g.

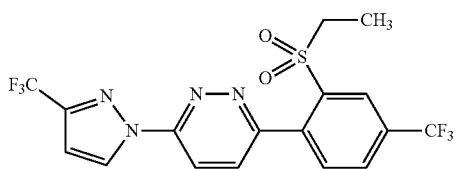 [SMILES: CCS(=O)(=O)c1cc(C(F)(F)F)ccc1-c1ccc(-n2ccc(C(F)(F)F)n2)nn1]

The present compound 1: $^1$H-NMR (CDCl$_3$) δ: 8.89 (1H, d), 8.49 (1H, s), 8.42 (1H, d), 8.06 (1H, d), 7.84 (1H, d), 7.68 (1H, d), 6.84 (1H, d), 3.49 (2H, q), 1.33 (3H, t).

Preparation Example 2

The compounds prepared according to a similar method to that described in the Preparation example 1 and its physical properties are shown as follows.

A compound represented by formula (I-A):

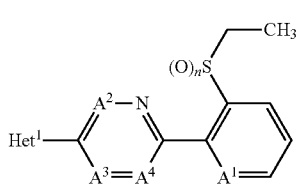

wherein Het$^1$, A$^1$, A$^2$, A$^3$, A$^4$, and n are shown in any of [Table 7].

TABLE 7

| Present compound | Het$^1$ | A$^1$ | A$^2$ | A$^3$ | A$^4$ | n |
|---|---|---|---|---|---|---|
| 2 | F$_3$C-pyrazole | N | N | CH | CH | 2 |
| 3 | Cl-triazole | N | N | CH | CH | 2 |
| 4 | F$_3$C-triazole | N | N | CH | CH | 2 |
| 5 | Br-triazole | N | N | CH | CH | 2 |
| 6 | NC-triazole | N | N | CH | CH | 2 |
| 7 | F$_3$C-imidazole | N | N | CH | CH | 2 |
| 8 | Br-pyrazole | N | N | CH | CH | 2 |
| 9 | F$_3$C-pyrazole | N | N | CH | CH | 2 |
| 10 | F$_3$C-pyrazole | N | CH | N | CH | 2 |
| 11 | F$_3$C-triazole | N | CH | N | CH | 2 |
| 12 | F$_3$C-imidazole | N | CH | N | CH | 2 |
| 13 | F$_3$C-pyrazole | N | CH | N | CH | 2 |

The present compound 2: $^1$H-NMR (CDCl$_3$) δ: 8.97 (1H, dd), 8.90-8.89 (1H, m), 8.56 (1H, dd), 8.44 (1H, d), 8.16 (1H, d), 7.68 (1H, dd), 6.83 (1H, d), 3.92 (2H, q), 1.43 (3H, t).

The present compound 3: $^1$H-NMR (CDCl$_3$) δ: 9.35 (1H, s), 8.97 (1H, dd), 8.57 (1H, dd), 8.22 (2H, q), 7.69 (1H, dd), 3.90 (2H, q), 1.44 (3H, t).

The present compound 4: $^1$H-NMR (CDCl$_3$) δ: 9.53 (1H, s), 8.98 (1H, dd), 8.57 (1H, dd), 8.35 (1H, d), 8.24 (1H, d), 7.71 (1H, dd), 3.90 (2H, q), 1.45 (3H, t).

The present compound 5: $^1$H-NMR (CDCl$_3$) δ: 9.33 (1H, s), 8.97 (1H, dd), 8.56 (1H, dd), 8.26 (1H, d), 8.20 (1H, d), 7.69 (1H, dd), 3.90 (2H, q), 1.44 (3H, t).

The present compound 6: $^1$H-NMR (CDCl$_3$) δ: 9.53 (1H, s), 8.98 (1H, dd), 8.57 (1H, dd), 8.31 (1H, d), 8.25 (1H, d), 7.71 (1H, dd), 3.88 (2H, q), 1.44 (3H, t).

The present compound 7: $^1$H-NMR (CDCl$_3$) δ: 8.97 (1H, dd), 8.57 (1H, dd), 8.53 (1H, s), 8.22-8.20 (1H, m), 8.19 (1H, d), 7.81 (1H, d), 7.70 (1H, dd), 3.90 (2H, q), 1.45 (3H, t).

The present compound 8: $^1$H-NMR (CDCl$_3$) δ: 8.95 (1H, dd), 8.86 (1H, s), 8.56 (1H, dd), 8.35 (1H, d), 8.12 (1H, d), 7.80 (1H, s), 7.66 (1H, dd), 3.92 (2H, q), 1.44 (3H, t).

The present compound 9: $^1$H-NMR (CDCl$_3$) δ: 9.15 (1H, s), 8.96 (1H, dd), 8.56 (1H, dd), 8.41 (1H, d), 8.16 (1H, d), 8.02 (1H, s), 7.67 (1H, dd), 3.91 (2H, q), 1.41 (3H, t).

The present compound 10: $^1$H-NMR (CDCl$_3$) δ: 9.38 (1H, d), 8.96-8.93 (2H, m), 8.66 (1H, dd), 8.55-8.52 (1H, m), 7.64 (1H, ddd), 6.80 (1H, d), 3.87 (2H, q), 1.42 (3H, t).

The present compound 11: $^1$H-NMR (CDCl$_3$) δ: 9.30 (2H, d), 8.98 (2H, td), 8.54 (1H, dd), 7.68 (1H, dd), 3.84 (2H, q), 1.43 (3H, t).

The present compound 12: $^1$H-NMR (CDCl$_3$) δ: 9.03 (1H, s), 8.97 (1H, t), 8.83 (1H, d), 8.54 (1H, t), 8.48 (1H, s), 8.12 (1H, s), 7.68 (1H, dd), 3.84 (2H, q), 1.42 (3H, t).

The present compound 13: $^1$H-NMR (CDCl$_3$) δ: 9.34 (1H, d), 8.95 (1H, dd), 8.93 (1H, d), 8.90 (1H, s), 8.54 (1H, dd), 8.00 (1H, s), 7.65 (1H, dd), 3.87 (2H, q), 1.42 (3H, t).

Preparation Example 3

To a mixture of the intermediate compound 14 0.15 g and DMF 3.5 mL, sodium hydride 81 mg and 3-(trifluoromethyl) pyrazole 0.28 g were added at room temperature. The mixture was stirred at 80° C. for 2 hours. After the mixture was cooled to room temperature, the mixture was concentrated under reduced pressure. To the resulting residue was added water and the mixture was extracted with MTBE. The organic layer was washed with saturated brine, dried over anhydrous sodium sulfate, and concentrated under reduced pressure. The resulting residue was subjected to a silica gel chromatography to give the present compound 14 shown below 0.29 g.

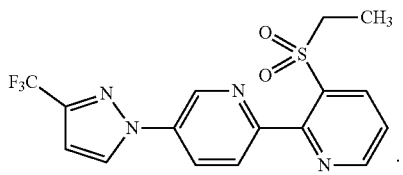

The present compound 14: $^1$H-NMR (CDCl$_3$) δ: 9.06 (1H, d), 8.89 (1H, dd), 8.50 (1H, dd), 8.20 (1H, dd), 8.06 (1H, s), 7.99 (1H, d), 7.57 (1H, dd), 6.80 (1H, d), 3.90 (2H, q), 1.39 (3H, t).

Preparation Example 4

The compound prepared according to a similar method to that described in the Preparation example 3 and its physical properties are shown as follows.

A compound represented by formula (I-A):

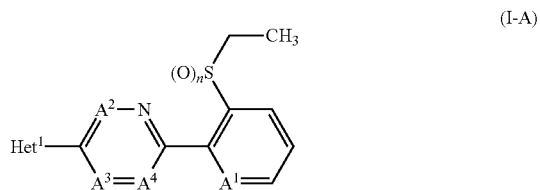

wherein Het$^1$, A$^1$, A$^2$, A$^3$, A$^4$, and n are shown in [Table 8].

TABLE 8

| Present compound | Het$^1$ | A$^1$ | A$^2$ | A$^3$ | A$^4$ | n |
|---|---|---|---|---|---|---|
| 15 | ![pyrazole with F3C] | N | CH | CH | CH | 2 |

The present compound 11: $^1$H-NMR (CDCl$_3$) δ: 9.05 (1H, dd), 8.91 (1H, dd), 8.52 (1H, dd), 8.32 (1H, t), 8.21 (1H, dd), 8.02 (1H, dd), 8.00 (1H, s), 7.60 (1H, dd), 3.92 (2H, q), 1.41 (3H, t).

Next, the formulation examples of the present compound are shown below. The "parts" represents "part by weight".

Formulation Example 1

Into a mixture of 10 parts of any one of the present compounds 1 to 15, 35 parts of xylene, and 35 parts of DMF, and then 14 parts of polyoxyethylene styryl phenyl ether and 6 parts of calcium dodecylbenzene sulfonate are added, followed by mixing them to obtain each formulation.

Formulation Example 2

Four (4) parts of sodium lauryl sulfate, 2 parts of calcium lignin sulfonate, 20 parts of synthetic hydrous silicon oxide fine powder, and 54 parts of diatomaceous earth are mixed, and further 20 parts of any one of the present compounds 1 to 15 is added thereto, followed by mixing them to obtain each wettable powder.

Formulation Example 3

To 2 parts of any one of the present compounds 1 to 15, 1 part of synthetic hydrous silicon oxide fine powder, 2 parts of calcium lignin sulfonate, 30 parts of bentonite, and 65 parts of kaolin clay are added, followed by mixing them. To the mixtures is then added an appropriate amount of water, and the mixtures are further stirred, granulated with a granulator, and forced-air dried to obtain each granular formulation.

Formulation Example 4

Into an appropriate amount of acetone, 1 part of any one of the present compounds 1 to 15 is mixed, and then 5 parts of synthetic hydrous silicon oxide fine powder, 0.3 parts of isopropyl acid phosphate, and 93.7 parts of kaolin clay are added, following by mixing them with stirring thoroughly and removal of acetone from the mixture by evaporation to obtain each powder formulation.

Formulation Example 5

A mixture of 35 parts of polyoxyethylene alkyl ether sulfate ammonium salt and white carbon (weight ratio of 1:1), 10 parts of any one of the present compounds 1 to 15, and 55 parts of water are mixed, followed by finely grounding them by a wet grinding method to obtain each flowable formulation.

Formulation Example 6

Into a mixture of 5 parts of xylene and 5 parts of trichloroethane, 0.1 parts of any one of the present compounds 1 to 15 are mixed, and the resulting mixture is then mixed with 89.9 parts of kerosene to obtain each oil solution.

Formulation Example 7

Into 0.5 ml of acetone, 10 mg of any one of the present compounds 1 to 15 is mixed, and the solution is added dropwise to 5 g of a solid feed powder for an animal (solid feed powder for rearing and breeding CE-2, manufactured by CLEA Japan, Inc.), followed by mixing the resulting mixtures uniformly, and then by drying them by evaporation of acetone to obtain each poison bait.

Formulation Example 8

Into an aerosol can, 0.1 parts of any one of the present compounds 1 to 15 and 49.9 parts of Neothiozole (manufactured by Chuo Kesei Co., Ltd.) are placed. After mounting an aerosol valve, 25 parts of dimethyl ether and 25 parts of LPG are filled, followed by shaking and further mounting an actuator to obtain each oily aerosol.

Formulation Example 9

A mixture of 0.6 parts of any one of the present compounds 1 to 15, 0.01 parts of BHT (2,6-di-tert-butyl-4-methylphenol), 5 parts of xylene, 3.39 parts of kerosene, and 1 part of an emulsifier {Rheodol MO-60 (manufactured by Kao Corporation)}, and 50 parts of distilled water are filled into an aerosol container, and a valve part of the container is attached. Then, 40 parts of a propellant (LPG) is filled therein through the valve under pressure to obtain each aqueous aerosol.

Formulation Example 10

Zero point one (0.1) parts of any one of the present compounds 1 to 15 is mixed into 2 ml of propylene glycol, and the resulting solution is impregnated into a ceramic plate having a size of 4.0 cm×4.0 cm and a thickness of 1.2 cm to obtain each thermal fumigant.

Formulation Example 11

Five (5) parts of any one of the present compounds 1 to 15, and 95 parts of ethylene-methyl methacrylate copolymer (the ratio of the methyl methacrylate in the copolymer: 10 weight %, Acryft (registered by trademark) WD 301, manufactured by Sumitomo Chemical Co. Ltd.) are melted and kneaded with a closed type pressure kneader (manufactured by Moriyama Manufacturing Co., Ltd.), and the resulting kneaded product is extruded from an extrusion molding machine through a molding die to obtain each rod-shaped molded product having a length of 15 cm and a diameter of 3 mm.

Formulation Example 12

Five (5) parts of any one of the present compounds 1 to 15, and 95 parts of plasticized polyvinyl chloride resin are melted and kneaded with a closed type pressure kneader (manufactured by Moriyama Manufacturing Co., Ltd.), and the resulting kneaded product is extruded from an extrusion molding machine through a molding die to obtain each rod-shaped molded product having a length of 15 cm and a diameter of 3 mm.

Formulation Example 13

One-hundred (100) mg of any one of the present compounds 1 to 15, 68.75 mg of lactose, 237.5 mg of corn starch, 43.75 mg of microcrystalline cellulose, 18.75 mg of polyvinylpyrrolidone, 28.75 mg of sodium carboxymethyl starch, and 2.5 mg of magnesium stearate are mixed, and the resulting mixtures are compressed to an appropriate size to obtain each tablet.

Formulation Example 14

Twenty-five (25) mg of any one of the present compounds 1 to 15, 60 mg of lactose, 25 mg of corn starch, 6 mg of carmellose calcium, and an appropriate amount of 5% aqueous hydroxypropyl methylcellulose solution are mixed, and the resulting mixtures are filled into a hard shell gelatin capsule or a hydroxypropyl methylcellulose capsule to obtain each capsule.

Formulation Example 15

To 100 mg of any one of the present compounds 1 to 15, 500 mg of fumaric acid, 2000 mg of sodium chloride, 150 mg of methyl paraben, 50 mg of propyl paraben, 25,000 mg of granulated sugar, 13,000 mg of sorbitol (70% solution), 100 mg of Veegum K (manufactured by Vanderbilt Co.), 35 mg of a perfume, and 500 mg of a coloring agent, distilled water is added so that a final volume is set to be 100 mL, followed by mixing the mixtures to obtain each suspension for oral administration.

Formulation Example 16

Into a mixture of 5% by weight of an emulsifier, 3% by weight of benzyl alcohol and 30% by weight of propylene glycol, 5% by weight of any one of the present compounds 1 to 15 is mixed, and phosphate buffer is added thereto so that a pH of the solution is set to be 6.0 to 6.5, and water is added as the rest parts to obtain each solution for oral administration.

Formulation Example 17

To a mixture of 57% by weight of fractional distillated palm oil and 3% by weight of polysorbate 85, 5% by weight of aluminium distearate is added, and heated to disperse it. The resulting mixture is cooled to room temperature, and 25% by weight of saccharin is dispersed in an oil vehicle. Ten (10)% by weight of any one of the present compounds 1 to 15 is divided thereto to obtain each paste for oral administration.

Formulation Example 18

Five (5)% by weight of any one of the present compounds 1 to 15 is mixed with 95% by weight of limestone filler, followed by a wet-granulation of the resulting mixture to obtain each granule for oral administration.

Formulation Example 19

Into 80 parts of diethylene glycol monoethyl ether, 5 parts of any one of the present compounds 1 to 15 is mixed, and 15 parts of propylene carbonate is added thereto, and the resulting mixture is mixed to obtain each spot-on solution.

Formulation Example 20

Into 70 parts of diethylene glycol monoethyl ether, 10 parts of any one of the present compounds 1 to 15 is mixed, and 20 parts of 2-octyldodecanol is added thereto, and the resulting mixture is mixed to obtain each pour-on solution.

Formulation Example 21

To 0.5 parts of any one of the present compounds 1 to 15, 60 parts of Nikkol (registered by trademark) TEALS-42 (manufactured by Nikko Chemical Co. Ltd.: 42% of aqueous solution of lauryl sulfuric acid triethanol amine) and 20 parts of propylene glycol are added, and the resulting mixture is mixed with stirring thoroughly until the mixture becomes homogeneous, and 19.5 parts of water is then added thereto and the resulting mixture is further mixed with stirring thoroughly to obtain a homogeneous solution of each shampoo formulation.

Formulation Example 22

Zero point fifteen (0.15)% by weight of any one of the present compounds 1 to 15, 95% by weight of animal feed, as well as 4.85% by weight of a mixture of dibasic calcium phosphate, diatomaceous earth, Aerosil, and carbonate (or chalk) are mixed with stirring thoroughly to obtain each premix for animal feed.

Formulation Example 23

Seven point two (7.2) g of any one of the present compounds 1 to 15, and 92.8 g of Hosco (registered trademark) S-55 (manufactured by Maruishi Pharmaceuticals) are melted and mixed at 100° C., and the resulting mixtures are poured into a suppository mold, followed by performing a cooling solidification to obtain each suppository.

Next, Test examples are used to show an efficacy of the present compound on controlling harmful arthropods. The following Test examples were conducted at 25° C. while preventing insects from getting away.

Test Example 1

Test compounds are made to a formulation according to a similar method to that described in the Formulation example 5, and thereto is added water containing 0.03 v/v % of a spreader to prepare a diluted solution containing a prescribed concentration of the test compound.

Cucumber (*cucumber sativus*) seedling (on the developmental stage of the second true leaf) is planted in a cup, and approximately 30 cotton aphids (*Aphis gossypii*) (all stages of life) are released onto the seedling. After one day, the diluted solutions are sprayed into the seedling at a ratio of 10 mL/seedling. After 5 days, the number of the surviving insects is examined and the controlling value is calculated by the following equation.

Controlling value (%)=$\{1-(Cb \times Tai)/(Cai \times Tb)\} \times 100$ wherein the symbols in the equation represent the following descriptions.

Cb: Number of the test insects in untreated group;
Cai: Number of the surviving insects at the time of the examination in untreated group;
Tb: Number of the test insects in treated group;
Tai: Number of the surviving insects at the time of the examination in treated group;

Here the "untreated group" represents a group where a similar treatment procedure to that of treated group except not using the test compound is done.

The test was conducted according to a similar method to that described in the Test example 1 by making the prescribed concentration 500 ppm and using the below-mentioned present compounds as a test compound, and, as the result of the test, the test compounds showed 90% or more as the controlling value.

Present compound Nos: 2, 3, 4, 5, 7, 8, 9, 10, 11, 12, 13, and 14.

The test was conducted according to a similar method to that described in the Test example 1 by making the prescribed concentration 200 ppm and using the below-mentioned present compounds as a test compound, and, as the result of the test, the test compounds showed 90% or more as the controlling value.

Present compound Nos: 2, 4, 7, 8, 9, and 11.

Test Example 2

Test compounds are made to a formulation according to a similar method to that described in the Formulation example 5, and thereto is added water to prepare a diluted solution containing a prescribed concentration of the test compound.

Cucumber (*cucumber sativus*) seedling (on the developmental stage of the second true leaf) is planted in a cup, and the diluted solutions are drenched to the foot of the seedling at a ratio of 5 mL/seedling. After 7 days, approximately 30 cotton aphids (*Aphis gossypii*) (all stages of life) are released onto the leaf of the seedling. After 6 days, the number of the surviving insects is examined and the controlling value is calculated by the following equation.

Controlling value (%)=$\{1-(Cb \times Tai)/(Cai \times Tb)\} \times 100$ wherein the symbols in the equation represent the following descriptions.

Cb: Number of the test insects in untreated group;
Cai: Number of the surviving insects at the time of the examination in untreated group;
Tb: Number of the test insects in treated group;
Tai: Number of the surviving insects at the time of the examination in treated group;

Here the "untreated group" represents a group where a similar treatment procedure to that of treated group except not using the test compound is done.

The test was conducted according to a similar method to that described in the Test example 2 by making the prescribed concentration 1000 ppm and using the below-mentioned present compounds as a test compound, and, as the result of the test, the test compounds showed 90% or more as the controlling value.

Present compound Nos: 4, 9, and 11.

Test Example 3

Test compounds are made to a formulation according to a similar method to that described in the Formulation example 5, and thereto is added water containing 0.03 v/v % of a spreader to prepare a diluted solution containing a prescribed concentration of the test compound.

Rice (*Oryza sativa*) seedling (on the developmental stage of the second true leaf) is planted in a cup, and the diluted solutions are sprayed into the seedling at a ratio of 10 mL/seedling. Thereafter, 20 brown planthoppers (*Nilaparvata lugens*) at the third instar larval stage are released onto the seedling. After 6 days, the number of the surviving insects is examined, and the mortality is calculated by the following equation.

Mortality (%)=$\{1-\text{Number of surviving insects}/20\} \times 100$

The test was conducted according to a similar method to that described in the Test example 3 by making the prescribed concentration 500 ppm and using the below-mentioned present compounds as a test compound, and, as the result of the test, the test compounds showed 90% or more as the mortality of insects.

Present compound Nos: 9, and 10.

Test Example 4

Test compounds are made to a formulation according to a similar method to that described in the Formulation example 5, and thereto is added water to prepare a diluted solution containing a prescribed concentration of the test compound.

The diluted solution 5 mL is added to one cup, and Rice (*Oryza sativa*) seedling (on the developmental stage of the second true leaf) is planted in the other cup with a hole on the bottom and the other cup is placed on the cup. After 7 days, 20 brown planthoppers (*Nilaparvata lugens*) at the third instar larval stage are released onto the seedling. After 6 days, the number of the surviving insects is examined, and the mortality is calculated by the following equation.

Mortality (%)={1−Number of surviving insects/20}× 100

The test was conducted according to a similar method to that described in the Test example 4 by making the prescribed concentration 1000 ppm and using the below-mentioned present compounds as a test compound, and, as the result of the test, the test compounds showed 90% or more as the mortality of insects.

Present compound No: 9.

Test Example 5

Test compounds are made to a formulation according to a similar method to that described in the Formulation example 5, and thereto is added water to prepare a diluted solution containing a prescribed concentration of the test compound.

Seven point seven (7.7) g of artificial feed (Insecta LF, manufactured by Nosan Corporation) is placed in a cup, and 2 mL of the diluted solution is drenched to the cup. Five (5) tobacco cutworms (*Spodoptera litura*) at the fourth instar larval stage are released on the artificial feed. After 5 days, the number of the surviving insects is examined, and the mortality is calculated by the following equation.

Mortality (%)={1−Number of surviving insects/5}× 100

The test was conducted according to a similar method to that described in the Test example 5 by making the prescribed concentration 500 ppm and using the below-mentioned present compounds as a test compound, and, as the result of the test, the test compounds showed 80% or more as the mortality of insects.

Present compound Nos: 1, 12, and 13.

Test Example 6

Test compounds are made to a formulation according to a similar method to that described in the Formulation example 5, and thereto is added water containing 0.03 v/v % of a spreader to prepare a diluted solution containing a prescribed concentration of the test compound.

Cabbage (*Brassicae oleracea*) seedling (on the developmental stage of the second to third true leaf) is planted in a cup, and the diluted solutions are sprayed into the seedling at a ratio of 20 mL/seedling. Thereafter, the stem and leaf thereof is cut out and then is installed into a cup that is covered with filter paper on the bed of the cup. Five (5) cabbage moths (*Plutella xylostella*) at the second instar larval stage are released into the cup. After 5 days, the number of the surviving insects is counted, and the mortality of insects is calculated by the following equation.

Mortality (%)=(1−Number of surviving insects/5)× 100

The test was conducted according to a similar method to that described in the Test example 6 by making the prescribed concentration 500 ppm and using the below-mentioned present compounds as a test compound, and, as the result of the test, the test compounds showed 80% or more as the mortality of insects.

Present compound Nos: 1, 2, 4, 5, 8, 9, 10, 11, 12, 13, 14, and 15.

Test Example 7

Test compounds are made to a formulation according to a similar method to that described in the Formulation example 5, and thereto is added water containing 0.03 v/v % of a spreader to prepare a diluted solution containing a prescribed concentration of the test compound.

Cabbage (*Brassicae oleracea*) seedling (on the developmental stage of the third to fourth true leaf) is planted in a cup, and the diluted solutions are sprayed into the seedling at a ratio of 20 mL/seedling. Thereafter, 10 cabbage moths (*Plutella xylostella*) at the third instar larval stage are released into the cup. After 5 days, the number of the surviving insects is counted, and the mortality of insects is calculated by the following equation.

Mortality (%)=(1−Number of surviving insects/10)× 100

The test was conducted according to a similar method to that described in the Test example 7 by making the prescribed concentration 200 ppm and using the below-mentioned present compounds as a test compound, and, as the result of the test, the test compounds showed 90% or more as the mortality of insects.

Present compound Nos: 1, 2, 3, 4, 5, 7, 8, 9, 10, 11, 12, and 15.

Test Example 8

Each 1 mg of the test compounds is dissolved into 50 μL of a mixed solution of polyoxyethylene sorbitan mono-cocoate and acetone (polyoxyethylene sorbitan mono-cocoate:acetone=5:95 (v/v ratio)). Thereto is added water containing 0.03% by volume of a spreader to prepare a diluted solution containing a prescribed concentration of the test compound.

Corns (*Zea mays*) are sown on a tray overlaid with damped KimWipes. After the corns are grown for 5 days, the entire seedling of the corns is immersed into the diluted solution for 30 seconds. Thereafter, each two grains of the seedlings are installed in a plastic petri dish (90 mm radius), and 10 Western corn rootworms (*Diabrotica virgifera virgifera*) at the second instar larval stage are released into the dish. After 5 days, the number of the died insects is counted, and the mortality of insects is calculated by the following equation.

Mortality (%)={Number of died insects/10}×100

The test was conducted according to a similar method to that described in the Test example 8 by making the prescribed concentration 500 ppm and using the below-mentioned present compounds as a test compound, and, as the result of the test, the test compounds showed 80% or more as the mortality of insects.

Present compound Nos: 2, 9, 10, 11, 12, 13, and 15.

Test Example 9

Each 1 mg of the test compounds is dissolved into 10 μL of a mixed solution of xylene, DMF, and a surfactant (xylene:DMF:surfactant=4:4:1 (v/v ratio)). Thereto is added water containing 0.03% by volume of a spreader to prepare a diluted solution containing a prescribed concentration of the test compound.

Cucumber (*cucumber sativus*) seedling (on the developmental stage of the second to third true leaf) is planted in a cup, and the diluted solutions are sprayed into the seedling at a ratio of 10 mL/seedling. Thereafter, the second leaf thereof is cut out and installed into the cup, and then 10 Cucurbit leaf beetles (*Aulacophora femoralis*) at the second instar larval stage are released into the cup. After 5 days, the number of the died insects is counted, and the mortality of insects is calculated by the following equation.

Mortality (%)={Number of died insects/10}×100

The test was conducted according to a similar method to that described in the Test example 9 by making the prescribed concentration 50 ppm and using the below-mentioned present compounds as a test compound, and, as the result of the test, the test compounds showed 80% or more as the mortality of insects.

Present compound Nos: 1, 3, 4, 7, 8, and 9.

Test Example 10

Test compounds are made to a formulation according to a similar method to that described in the Formulation example 5, and thereto is added water to prepare a diluted solution containing a prescribed concentration of the test compound.

A filter paper having a diameter of 5.5 cm in diameter is spread on the bottom of the cup, and 30 mg of sucrose is placed on the filter paper, and then 0.7 ml of the diluted solutions are added dropwise to the filter paper. Ten (10) houseflies (*Musca domestica*) female adult are released into the cup. After 24 hours, the number of the died insects is counted, and the mortality of insects is calculated by the following equation.

Mortality (%)=(Number of died insects/test insects)×100

The test was conducted according to a similar method to that described in the Test example 10 by making the prescribed concentration 500 ppm and using the below-mentioned present compounds as a test compound, and, as the result of the test, the test compounds showed 100% as the mortality of insects.

Present compound Nos: 2, 4, 7, and 9.

INDUSTRIAL APPLICABILITY

The present compound shows an excellent control effect against a harmful arthropod.

The invention claimed is:
1. A compound represented by formula (I):

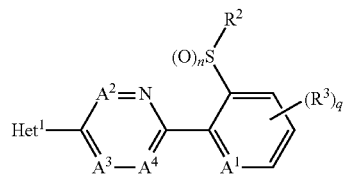

wherein,
Het$^1$ represents Het$^1$-1, Het$^1$-2, Het$^1$-3, or Het$^1$-4:

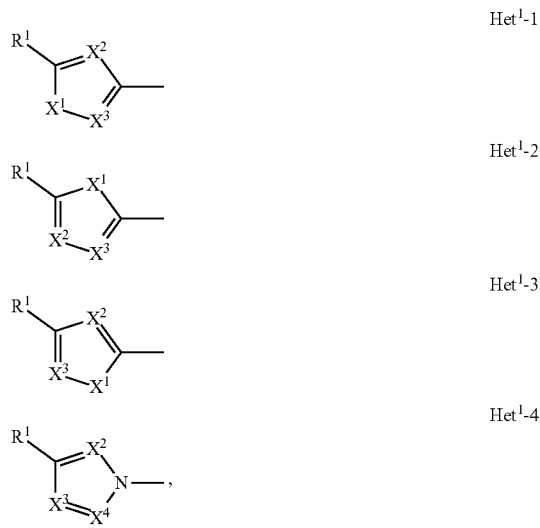

$R^1$ represents $OR^4$, $OS(O)_2R^4$, $S(O)_mR^4$, $NR^5S(O)_2R^4$, a cyano group, a C1-C4 chain hydrocarbon group having one or more halogen atoms, or a halogen atom, $R^4$ represents a C1-C4 chain hydrocarbon group having one or more halogen atoms, $R^5$ represents a hydrogen atom, or a C1-C6 chain hydrocarbon group optionally having one or more halogen atoms, $X^1$ represents $NR^{30}$, an oxygen atom, or a sulfur atom, $X^2$ represents a nitrogen atom or $CR^{31}$, $X^3$ represents a nitrogen atom or $CR^{32}$, $X^4$ represents a nitrogen atom or $CR^{33}$, $R^{30}$, $R^{31}$, $R^{32}$, and $R^{33}$ each independently represents a hydrogen atom, a C1-C6 chain hydrocarbon group optionally having one or more halogen atoms, a C3-C6 alicyclic hydrocarbon group optionally having one or more halogen atoms, or a halogen atom, $A^1$ represents a nitrogen atom or $CR^9$, A combination of $A^2$, $A^3$, and $A^4$ represents
a combination in which $A^2$ is $CR^6$, $A^3$ is $CR^7$, and $A^4$ is $CR^8$,
a combination in which $A^2$ is a nitrogen atom, $A^3$ is $CR^7$, and $A^4$ is $CR^8$,
a combination in which $A^2$ is $CR^6$, $A^3$ is a nitrogen atom, and $A^4$ is $CR^8$, or
a combination in which $A^2$ is $CR^6$, $A^3$ is $CR^7$, and $A^4$ is a nitrogen atom, $R^9$ represents a hydrogen atom or a halogen atom, $R^6$, $R^7$, and $R^8$ each independently represents a hydrogen atom, a C1-C6 chain hydrocarbon group optionally having one or more halogen atoms, a nitro group, $OR^{18}$, $NR^{18}R^{19}$, a cyano group, or a halogen atom, n represents 0, 1, or 2, $R^2$ represents a cyclopropyl group, a cyclopropylmethyl group, or a C1-C6 alkyl group optionally having one or more halogen atoms, q represents 0, 1, 2, or 3, $R^3$ represents a C1-C6 chain hydrocarbon group optionally having one or more substituents selected from Group B; a phenyl group optionally having one or more substituents selected from Group D; a 5 or 6 membered aromatic heterocyclic group optionally having one or more substituents selected from Group D; a nitro group; $OR^{12}$; $NR^{11}R^{12}$; $NR^{11a}R^{12a}$; $NR^{24}NR^{11}R^{12}$; $NR^{24}OR^{11}$; $NR^{11}C(O)R^{13}$; $NR^{24}NR^{11}C(O)R^{13}$; $NR^{11}C(O)OR^{14}$; $NR^{24}NR^{11}C(O)OR^{14}$; $NR^{11}C(O)NR^{15}R^{16}$; $NRR^{24}NR^{11}C(O)NR^{15}R^{16}$; $N=CHNR^{15}R^{16}$; $N=S(O)_xR^{15}R^{16}$; $S(O)_yR^{15}$; $C(O)OR^{17}$; $C(O)NR^{11}R^{12}$; a cyano group; or a halogen atom, and when q is 2 or 3, two or more $R^3$ may be identical to or different from each other, $R^{11}$, $R^{17}$, $R^{18}$, $R^{19}$, and $R^{24}$ each independently represents a hydrogen atom, or a C1-C6 chain hydrocarbon group optionally having one or more halogen atoms, $R^{12}$ represents a hydrogen atom, $S(O)_2R^{23}$, a C1-C6 chain hydrocarbon group optionally having one or more halogen atoms, or a C1-C6 alkyl group having one substituent selected from Group F, $R^{23}$ represents a C1-C6 chain hydrocarbon group optionally having one or more halogen atoms, or a phenyl group optionally having one or more substituents selected from Group D, $R^{11a}$ and $R^{12a}$ are taken together with the nitrogen atom to which they are attached to form a 3-7 membered nonaromatic heterocyclic group optionally having one or more substituents selected from Group E, wherein the 3-7 membered nonaromatic heterocycle represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiadinane ring, a thiomorpholine ring, or a 1,4-thiazepane ring, $R^{13}$ represents a hydrogen atom, a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, a phenyl group optionally having one or more substituents selected from Group D, or a 5 or 6 membered aromatic heterocyclic group optionally having one or more substituents selected from Group D, $R^{14}$ represents a C1-C6 chain hydrocarbon group optionally having one or more halogen atoms, a C3-C7 cycloalkyl group optionally having one or more halogen atoms, a (C3-C6 cycloalkyl)C1-C3 alkyl group optionally having one or more halogen atoms, or a phenyl C1-C3 alkyl group wherein the phenyl moiety in the phenyl C1-C3 alkyl group may optionally have one or more substituents selected from Group D, $R^{15}$ and $R^{16}$ each independently represents a C1-C6 alkyl group optionally having one or more halogen atoms, m represents 0, 1, or 2,
x represents 0 or 1,
y represents 0, 1, or 2, wherein Group B consists of a C1-C6 alkoxy group optionally having one or more halogen atoms, a C3-C6 alkenyloxy group optionally having one or more halogen atoms, a C3-C6 alkynyloxy group optionally having one or more halogen atoms, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, a C3-C6 cycloalkyl group optionally having one or more halogen atoms, a cyano group, a hydroxy group, and a halogen atom, wherein Group C consists of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, and a halogen atom, wherein Group D consists of a C1-C6 chain hydrocarbon group optionally having one or more halogen atoms, a hydroxy group, a C1-C6 alkoxy group optionally having one or more halogen atoms, a C3-C6 alkenyloxy group optionally having one or more halogen atoms, a C3-C6 alkynyloxy group optionally having one or more halogen atoms, a sulfanyl group, a C1-C6 alkylsulfanyl group optionally having one or more halogen atoms, a C1-C6 alkylsulfinyl group optionally having one or more halogen atoms, a C1-C6 alkylsulfonyl group optionally having one or more halogen atoms, an amino group, $NHR^{21}$, $NR^{21}R^{22}$, $C(O)R^{21}$, $OC(O)R^{21}$, $C(O)OR^{21}$, a cyano group, a nitro group, and a halogen atom, wherein $R^{21}$ and $R^{22}$ each independently represents a C1-C6 alkyl group optionally having one or more halogen atoms, wherein Group E consists of a C1-C6 chain hydrocarbon group optionally having one or more halogen atoms, a C1-C6 alkoxy group optionally having one or more halogen atoms, a C3-C6 alkenyloxy group optionally having one or more halogen atoms, a C3-C6 alkynyloxy group optionally having one or more halogen atoms, a halogen atom, an oxo group, a hydroxy group, a cyano group, and a nitro group, and wherein Group F consists of a C1-C6 alkoxy group optionally having one or more halogen atoms, an amino group, $NHR^{21}$, $NR^{21}R^{22}$, a cyano group, a phenyl group optionally having one or more substituents selected from Group D, a 5 or 6 membered aromatic heterocyclic group optionally having one or more substituents selected from Group D, a C3-C7 cycloalkyl group optionally having one or more halogen atoms, and a 3-7 membered nonaromatic heterocyclic group optionally having one or more substituents selected from Group C wherein the 3-7 membered nonaromatic heterocycle represents an aziridine ring, an azetidine ring, a pyrrolidine ring, an imidazoline ring, an imidazolidine ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiadinane ring, a thiomorpholine ring, or a 1,4-thiazepane ring, or its N-oxide compound.

2. The compound according to claim 1, wherein the combination of $A^2$, $A^3$, and $A^4$ represents a combination in which $A^2$ is $CR^6$, $A^3$ is $CR^7$, and $A^4$ is $CR^8$, a combination in which $A^2$ is a nitrogen atom, $A^3$ is $CR^7$, and $A^4$ is $CR^8$, or a combination in which $A^2$ is $CR^6$, $A^3$ is a nitrogen atom, and $A^4$ is $CR^8$.

3. The compound according to claim 1, wherein the combination of $A^2$, $A^3$, and $A^4$ represents a combination in which $A^2$ is $CR^6$, $A^3$ is $CR^7$, and $A^4$ is $CR^8$.

4. The compound according to claim 1, wherein the combination of $A^2$, $A^3$, and $A^4$ represents a combination in which $A^2$ is a nitrogen atom, $A^3$ is $CR^7$, and $A^4$ is $CR^8$.

5. The compound according to claim 1, wherein the combination of $A^2$, $A^3$, and $A^4$ represents a combination in which $A^2$ is $CR^6$, $A^3$ is a nitrogen atom, and $A^4$ is $CR^8$.

6. The compound according to claim 1, wherein $Het^1$ represents $Het^1$-1, $Het^1$-2, $Het^1$-3, or $Het^1$-4.

7. The compound according to claim 1, wherein $Het^1$ represents $Het^1$-2 or $Het^1$-4.

8. The compound according to claim 1, wherein $Het^1$ represents $Het^1$-4.

9. The compound according to claim 1, wherein $R^3$ represents a C1-C6 alkyl group optionally having one or more halogen atoms, a phenyl group optionally having one or more substituents selected from Group G, a 5 membered aromatic heterocyclic group having one to four nitrogen atoms, a 6 membered aromatic heterocyclic group having one or two nitrogen atoms, $NR^{11}R^{12}$, $NR^{24}NR^{11}R^{12}$, or a halogen atom, Group G: the group consisting of a halogen atom and a C1-C6 haloalkyl group.

10. The compound according to claim 1, wherein $R^3$ represents a C1-C6 alkyl group optionally having one or more halogen atoms, or a halogen atom.

11. The compound according to claim 1, wherein $R^2$ represents an ethyl group.

12. The compound according to claim 1, wherein $A^1$ represents a nitrogen atom or CH, the combination of $A^2$, $A^3$, and $A^4$ represents a combination in which $A^2$ is $CR^6$, $A^3$ is $CR^7$, and $A^4$ is $CR^8$, a combination in which $A^2$ is a nitrogen atom, $A^3$ is $CR^7$, and $A^4$ is $CR^8$, or a combination in which $A^2$ is $CR^6$, $A^3$ is a nitrogen atom, and $A^4$ is $CR^8$, $R^1$ represents a C1-C4 chain hydrocarbon group having one or more halogen atoms, or a halogen atom, $R^2$ represents a methyl group or an ethyl group, $R^3$ represents a C1-C6 alkyl group optionally having one or more halogen atoms; a phenyl group optionally having one or more substituents selected from Group G; a 5 membered aromatic heterocyclic group having one to four nitrogen atoms wherein the 5 membered aromatic heterocyclic group may optionally have one or more substituents selected from Group G; a 6 membered aromatic heterocyclic group having one or two nitrogen atoms wherein the 6 membered aromatic heterocyclic group may optionally have one or more substituents selected from Group G; $NR^{11}R^{12}$; $NR^{24}NR^{11}R^{12}$; or a halogen atom, $R^{11}$, $R^{12}$, and $R^{24}$ each independently represents a hydrogen atom, or a C1-C3 alkyl group optionally having one or more halogen atoms, $R^6$, $R^7$, and $R^8$ each independently represents a hydrogen atom, a C1-C6 alkyl group optionally having one or more halogen atoms, or a halogen atom, $Het^1$ represents $Het^1$-2 or $Het^1$-4, and q represents 0 or 1, wherein Group G consists of a halogen atom and a C1-C6 haloalkyl group.

13. The compound according to claim 1, wherein $A^1$ represents a nitrogen atom or CH, the combination of $A^2$, $A^3$, and $A^4$ represents a combination in which $A^2$ is $CR^6$, $A^3$ is $CR^7$, and $A^4$ is $CR^8$, a combination in which $A^2$ is a nitrogen atom, $A^3$ is $CR^7$, and $A^4$ is $CR^8$, or a combination in which $A^2$ is $CR^6$, $A^3$ is a nitrogen atom, and $A^4$ is $CR^8$, $R^1$ represents a C1-C4 chain hydrocarbon group having one or more halogen atoms, or a halogen atom, $R^2$ represents a methyl group or an ethyl group, $R^3$ represents a C1-C6 alkyl group optionally having one or more halogen atoms; a phenyl group optionally having one or more substituents selected from Group G; a 5 membered aromatic heterocyclic group having one to four nitrogen atoms wherein the 5 membered aromatic heterocyclic group may optionally have one or more substituents selected from Group G; a 6 membered aromatic heterocyclic group having one or two nitrogen atoms wherein the 6 membered aromatic heterocyclic group may optionally have one or more substituents selected from Group G; $NR^{11}R^{12}$; $NR^{24}NR^{11}R^{12}$; or a halogen atom, $R^{11}$, $R^{12}$, and $R^{24}$ each independently represents a hydrogen atom, or a C1-C3 alkyl group optionally having one or more halogen atoms, $R^6$, $R^7$, and $R^8$ each independently represents a hydrogen atom, a C1-C6 alkyl group optionally having one or more halogen atoms, or a halogen atom, $Het^1$ represents $Het^1$-2 or $Het^1$-4, and q represents 0 or 1.

14. The compound according to claim 1, wherein $A^1$ represents a nitrogen atom or CH, the combination of $A^2$, $A^3$, and $A^4$ represents a combination in which $A^2$ is CH, $A^3$ is CH, and $A^4$ is CH, a combination in which $A^2$ is a nitrogen atom, $A^3$ is CH, and $A^4$ is CH, or a combination in which $A^2$ is CH, $A^3$ is a nitrogen atom, and $A^4$ is CH, $R^1$ represents a C1-C4 chain hydrocarbon group having one or more halogen atoms, or a halogen atom, $R^2$ represents an ethyl group, q represents 0 or 1, $R^3$ represents a C1-C6 alkyl group optionally having one or more halogen atoms, or a halogen atom, and $Het^1$ represents $Het^1$-4.

15. A composition for controlling a harmful arthropod, comprising the compound according to claim 1, and an inert carrier.

16. A method for controlling a harmful arthropod, which comprises applying an effective amount of the compound according to claim 1 to a harmful arthropod or a habitat where the harmful arthropod lives.

17. A composition, comprising the compound according to claim 1, and one or more ingredients selected from the group consisting of Group (a), Group (b), Group (c), and Group (d), Group (a): the group consisting of an insecticidal ingredient, a miticidal ingredient, and a nematicidal ingredient, Group (b): a fungicidal ingredient, Group (c): a plant growth modulating ingredient, Group (d): a phytotoxicity-reducing ingredient.

* * * * *